US011918655B2

(12) United States Patent
Lowenthal et al.

(10) Patent No.: US 11,918,655 B2
(45) Date of Patent: *Mar. 5, 2024

(54) INTRANASAL EPINEPHRINE FORMULATIONS AND METHODS FOR THE TREATMENT OF DISEASE

(71) Applicant: Aegis Therapeutics, LLC, San Diego, CA (US)

(72) Inventors: Richard Lowenthal, San Diego, CA (US); Edward T. Maggio, San Diego, CA (US); Robert G. Bell, San Diego, CA (US); Pratik Shah, San Diego, CA (US)

(73) Assignee: AEGIS THERAPEUTICS, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,881

(22) Filed: Jun. 7, 2023

(65) Prior Publication Data

US 2024/0024485 A1  Jan. 25, 2024

Related U.S. Application Data

(63) Continuation of application No. 18/327,621, filed on Jun. 1, 2023, which is a continuation of application No. 18/049,936, filed on Oct. 26, 2022, now Pat. No. 11,717,571, which is a continuation of application No. 17/396,044, filed on Aug. 6, 2021, now Pat. No. 11,744,895, which is a continuation of application No. 16/869,461, filed on May 7, 2020, now Pat. No. 11,191,838, which is a continuation of application No. 16/420,044, filed on May 22, 2019, now Pat. No. 10,682,414, which is a continuation of application No. PCT/US2019/016918, filed on Feb. 6, 2019.

(60) Provisional application No. 62/784,057, filed on Dec. 21, 2018.

(51) Int. Cl.
*A61K 47/26* (2006.01)
*A61K 9/00* (2006.01)
*A61K 31/485* (2006.01)
*A61K 31/7016* (2006.01)

(52) U.S. Cl.
CPC ............ *A61K 47/26* (2013.01); *A61K 31/485* (2013.01); *A61K 31/7016* (2013.01); *A61K 9/0043* (2013.01); *A61K 9/0048* (2013.01); *A61K 9/0056* (2013.01); *A61K 9/006* (2013.01)

(58) Field of Classification Search
CPC .. A61K 47/26; A61K 31/485; A61K 31/7016; A61K 9/0043; A61K 9/0048; A61K 9/0056; A61K 9/006
USPC ...................................................... 514/282
See application file for complete search history.

(56) References Cited

U.S. PATENT DOCUMENTS

| 3,547,828 A | 12/1970 | Mansfield et al. |
|---|---|---|
| 5,192,528 A | 3/1993 | Radhakrishnan et al. |
| 5,369,095 A | 11/1994 | Kee et al. |
| 5,639,733 A | 6/1997 | Koike et al. |
| 5,661,130 A | 8/1997 | Meezan et al. |
| 5,789,375 A | 8/1998 | Mukae et al. |
| 5,795,896 A | 8/1998 | Lofroth et al. |
| 6,004,574 A | 12/1999 | Backstrom et al. |
| 6,254,854 B1 | 7/2001 | Edwards et al. |
| 6,524,557 B1 | 2/2003 | Backstrom et al. |
| 6,551,578 B2 | 4/2003 | Adjei et al. |
| 6,608,073 B1 | 8/2003 | Hussain et al. |
| 6,855,332 B2 | 2/2005 | Gizurarson et al. |
| 6,932,962 B1 | 8/2005 | Backstrom et al. |
| 8,268,791 B2 | 9/2012 | Maggio |
| 8,642,564 B2 | 2/2014 | Maggio |
| 9,561,177 B2 | 2/2017 | Keegan et al. |
| 9,629,965 B2 | 4/2017 | Crystal et al. |
| 9,642,913 B2 | 5/2017 | Maggio |
| 9,789,071 B2 | 10/2017 | Fleming |
| 9,895,444 B2 | 2/2018 | Maggio |
| 10,039,710 B2 | 8/2018 | Potta et al. |
| 10,265,402 B2 | 4/2019 | Maggio |
| 10,576,156 B2 | 3/2020 | Maggio |
| 10,682,414 B2 | 6/2020 | Lowenthal et al. |
| 11,173,209 B2 | 11/2021 | Maggio |
| 11,191,838 B2 | 12/2021 | Lowenthal et al. |
| 11,571,384 B2 | 2/2023 | Potta et al. |
| 11,717,571 B2 * | 8/2023 | Lowenthal ........... A61K 31/485 514/282 |
| 2002/0141971 A1 | 10/2002 | Frey, II |
| 2003/0158206 A1 | 8/2003 | Billotte et al. |

(Continued)

FOREIGN PATENT DOCUMENTS

| AT | 386414 B | 8/1988 |
|---|---|---|
| JP | H01151528 A | 6/1989 |

(Continued)

OTHER PUBLICATIONS

Aegis News Release, Aegis Therapeutics Celebrates 10th Anniversary (Oct. 28, 2013), https://www.globenewswire.com/fr/news-release/2013/10/28/1007033/0/en/Aegis-Therapeutics-Celebrates-10th-Anniversary.html (last visited Jul. 29, 2021).

Aegis Therapeutics, Aegis Announces Breakthrough in Non-Invasive, Rapid Onset, Acute Pain Control (Oct. 10, 2017), https://www.globenewswire.com/en/news-release/2017/10/10/1143680/0/en/Aegis-Announces-Breakthrough-in-Non-Invasive-Rapid-Onset-Acute-Pain-Control.html (last visited Jul. 29, 2021).

Ahsan et al. Sucrose cocoate, a component of cosmetic preparations, enhances nasal and ocular peptide absorption. Int. J. Pharm. 251(1-2):195-203 (2003).

(Continued)

*Primary Examiner* — Yih-Horng Shiao
(74) *Attorney, Agent, or Firm* — WILSON SONSINI GOODRICH & ROSATI

(57) ABSTRACT

Drug products adapted for nasal delivery comprising formulations with epinephrine and devices comprising such formulations are provided. Methods of treating anaphylaxis with epinephrine products are also provided.

44 Claims, 9 Drawing Sheets

(56) References Cited

U.S. PATENT DOCUMENTS

| | | |
|---|---|---|
| 2004/0248846 A1 | 12/2004 | Quay et al. |
| 2005/0234101 A1 | 10/2005 | Stenkamp et al. |
| 2006/0045868 A1 | 3/2006 | Meezan et al. |
| 2006/0045869 A1 | 3/2006 | Meezan et al. |
| 2006/0046962 A1 | 3/2006 | Meezan et al. |
| 2006/0046969 A1 | 3/2006 | Maggio |
| 2006/0147386 A1 | 7/2006 | Wermeling |
| 2007/0059254 A1 | 3/2007 | Singh |
| 2007/0293582 A1 | 12/2007 | Hill |
| 2007/0298010 A1 | 12/2007 | Maggio |
| 2008/0194461 A1 | 8/2008 | Maggio |
| 2008/0268032 A1 | 10/2008 | Maggio |
| 2008/0299079 A1 | 12/2008 | Meezan et al. |
| 2009/0004281 A1 | 1/2009 | Nghiem et al. |
| 2009/0047347 A1 | 2/2009 | Maggio |
| 2009/0156478 A1 | 6/2009 | Lau et al. |
| 2009/0258865 A1 | 10/2009 | Cartt et al. |
| 2009/0326193 A1 | 12/2009 | Maggio et al. |
| 2010/0068209 A1 | 3/2010 | Maggio |
| 2010/0112050 A1 | 5/2010 | Ryoo et al. |
| 2010/0160378 A1 | 6/2010 | Maggio |
| 2010/0203014 A1 | 8/2010 | Maggio |
| 2010/0203119 A1 | 8/2010 | Leane et al. |
| 2010/0209357 A1 | 8/2010 | Levitt |
| 2010/0209485 A1 | 8/2010 | Maggio |
| 2012/0021980 A1 | 1/2012 | Maggio |
| 2013/0224300 A1 | 8/2013 | Maggio |
| 2013/0253009 A1 | 9/2013 | Maggio |
| 2014/0107145 A1 | 4/2014 | Maggio |
| 2014/0162965 A1 | 6/2014 | Maggio |
| 2015/0005356 A1 | 1/2015 | Fleming |
| 2015/0374832 A1 | 12/2015 | Surakitbanharn |
| 2016/0051494 A1 | 2/2016 | Gulfo |
| 2017/0079907 A1 | 3/2017 | Potta et al. |
| 2017/0216199 A1 | 8/2017 | Potta et al. |
| 2018/0104344 A1 | 4/2018 | Maggio |
| 2018/0169247 A1 | 6/2018 | Maggio |
| 2018/0289617 A1 | 10/2018 | Potta et al. |
| 2018/0289639 A1 | 10/2018 | Potta et al. |
| 2018/0318215 A1 | 11/2018 | Potta et al. |
| 2019/0269780 A1 | 9/2019 | Lowenthal et al. |
| 2019/0269782 A1 | 9/2019 | Lowenthal et al. |
| 2021/0361770 A1 | 11/2021 | Lowenthal et al. |
| 2023/0085636 A1 | 3/2023 | Lowenthal et al. |

FOREIGN PATENT DOCUMENTS

| | | |
|---|---|---|
| JP | 2013505924 A | 2/2013 |
| JP | 2016531140 A | 10/2016 |
| WO | WO-9119481 A1 | 12/1991 |
| WO | WO-9405262 A1 | 3/1994 |
| WO | WO-9500151 A1 | 1/1995 |
| WO | WO-0076506 A1 | 12/2000 |
| WO | WO-0112155 A1 | 2/2001 |
| WO | WO-2005018565 A2 | 3/2005 |
| WO | WO-2006025882 A2 | 3/2006 |
| WO | WO-2011139838 A2 | 11/2011 |
| WO | WO-2014127020 A1 | 8/2014 |
| WO | WO-2015095389 A1 | 6/2015 |
| WO | WO-2018093666 A1 | 5/2018 |
| WO | WO-2018195029 A1 | 10/2018 |
| WO | WO-2019157099 A1 | 8/2019 |

OTHER PUBLICATIONS

Arfi et al. Acute Myocardial Ischemia Following Accidental Intravenous Administration of Epinephrine in High Concentration. Indian Heart J. 57:261 (2005).

Arizona State University library record for C. Srisawat et al., A Preliminary Study of Intranasal Epinephrine Administration as a Potential Route for Anaphylaxis Treatment. Asian Pac. J. Allergy. Immunol. 34:38 (2016).

Arnold et al. Correlation of tetradecylmaltoside induced increases in nasal peptide drug delivery with morphological changes in nasal eithelial cells. J. Pharm. Sci. 93.9:2205-2213 (2004).

Arthur. Epinephrine: A Short History. The Lancet Resp. Med. 3(5):350 (2015).

Aungst. Absorption enhancers: applications and advances. AAPS J. 14(1):10-8 (2012).

Auvi-Q Prescribing Information (Revised Nov. 2017) (24 pg).

Berge et al. Pharmaceutical Salts. Journal of Pharmaceutical Sciences 66(1):1-19 (Jan. 1977).

Bhairi. A guide to the properties and uses of detergents in biological systems. Calloiochem, pp. 1-42 (2001).

Breuer et al. Pharmacokinetics and Pharmacodynamics of Moist Inhalation Epinephrine using a Mobile Inhaler. Eur. J. Clin. Pharmacol. 69:1303-1310 (2013).

Brustugun et al. Photostability of epinephrine—the influence of bisulfite and degradation products. Pharmazie 59:457-463 (2004).

Budhwani et al. Severe Reversible Left Ventricular Systolic and Diastolic Dysfunction Due to Accidental Iatrogenic Epinephrine Overdose. Rev. Cardiovasc. Med. 5(2):130-133 (2004).

Campbell et al., Epinephrine in Anaphylaxis: Higher Risk of Cardiovascular Complications and Overdose after Administration of Intravenous Bolus Epinephrine Compared with Intramuscular Epinephrine. J. Allergy Clin. Immunol. Pract. 3:76 (2015).

Castro et al. Ecologically safe alkyl glycoside-based gemini surfactants. ARKIVOC Ixii:253-267 (2005).

Cayman Chemical Product Information Sheet, n-Dodecyl-β-D-maltoside (Sep. 18, 2014) (1 pg.).

Cunningham et al. Non-Invasive Nasal Hydromorphone with High Bioavailability for Rapid Onset and Non-Dissociative Acute Pain Control: A Feasibility Study. J. Bioequiv. Bioavailability 10:14 (2018).

Davis et al. Absorption enhancers for nasal drug delivery. Olin. Pharmacokine 42(13):1107-28 (2003).

Declaration of Karen Whitney (Aug. 12, 2021) (7 pgs.).

Djupesland. Nasal drug delivery devices: characteristics and performance in a clinical perspective—a review. Drug Deliv and Transl. Res. 3:42-62 (2013).

Duquesnoy et al. Comparative clinical pharmacokinetics of single doses of sumatriptan following subcutaneous, oral, rectal and intranasal administration. Eur. J. Pharm. Sci. 6(2):99-104 (1998).

Eley et al. In vitro assessment of alkylglycosides as permeability enhancers. AAPS PharmsciTech. 2(3): article 19, pp. 1-7 (2001).

Expert Declaration of Hugh D. C. Smyth, Ph.D. In Support of Petition For Inter Partes Review of U.S. Pat. No. 10,682,414 (dated Aug. 12, 2021).

Expert Declaration of Steven F. Weinstein, M.D. In Support of Petition For Inter Partes Review of U.S. Pat. No. 10,682,414 (dated Aug. 12, 2021).

Frew. What are the 'Ideal' Features of an Adrenaline (Epinephrine) Auto-Injector in the Treatment of Anaphylaxis? Allergy 68:15 (2011).

Handbook of Pharmaceutical Excipients (Raymond C. Rowe et al. eds., 6th ed. 2009) (excerpts) (24 pgs).

Hathcox et al. Inhibitory effects of sucrose fatty acid esters, alone and in combination with ethyienediaminetetraacetic acid and other organic acids, on viability of AR Escherichia co/10157:H7. Food Microbiology 13(3):213-225 (1996).

Illum et al. Nasal drug delivery—Recent developments and future prospects. J. Controlled AH Release 161(2):254-263 (2012).

Internet Archive, Web archive of Archive Issues—Asian Pacific Journal of Allergy and Immunology from Jul. 29, 2017, https://web.archive.org/web/20170729232720/ http://apjai-journal.org/archive-issues-2 (last visited Aug. 10, 2021).

Internet Archive, Web archive of Associate Professor Chatchawan Srisawat's online bio from Apr. 18, 2018, https://web.archive.org/web/20180418063549/ http:/www.si.mahidol.ac.th80/department/Biochemistry/home/CONTENT/Chat chawan_eng.htm.

Jayamali et al. Myocardial Infarction During Anaphylaxis in a Young Healthy Male with Normal Coronary Arteries-Is Epinephrine the Culprit? BMC Cardiovascular Disorders 17:237 (2017).

Junior et al. Topical Use of Adrenaline in Different Concentrations for Endoscopic Sinus Surgery. Braz. J. Otorhinolaryngol. 75(2):280-289 (2009).

(56) References Cited

OTHER PUBLICATIONS

Kanwar et al. Confusion About Epinephrine Dosing Leading to Iatrogenic Overdose: A Life-Threatening Problem with a Potential Solution. Ann. Emerg. Med. 55:341 (2010).

Kemp et al. Epinephrine: The Drug of Choice for Anaphylaxis—A Statement of the World Allergy Organization WAO J. 1:S18-S26 (2008).

Khoueiry et al. Reverse Takotsubo Cardiomyopathy in the Setting of Anaphylaxis Treated with High-Dose Intravenous Epinephrine. J. Emerg. Med. 44:96-99 (2013).

Kulkarni, et al. Formulation and characterization of nasal sprays. An examination of nasal sprat formulation parameters and excipients and their influence on key in vitro tests. Inhalation. Jun. 2012; 10-15.

Liew et al. Adrenaline Overdose in Pediatric Anaphylaxis: A Case Report, 11 J. Med. Case Reports 11:129 (2017).

Liu et al. Interaction between chitosan and alkyl P-D-glucopyranoside and its effect on their antimicrobial activity. Carbohydrate Polymers 56:243-250 (2004).

Maggio. Absorption Enhancing Excipients in Systemic Nasal Drug Delivery. Excipients and Food Chem. 5(2):100-12 (2014).

Maggio et al. High efficiency intranasal drug delivery using Intravail alkylsaccharide absorption enhancers. Drug Del Trans Res 3(1):16-25 (2012).

Maggio et al. Highly Bioavailable Nasal Calcitonin—Potential for Expanded use in Analgesia. Drug Delivery Tech 10:58-63 (2010).

Maggio. Intravail: highly effective intranasal delivery of peptide and protein drugs. Expert Opinion On Drug Delivery 3(4):529-539 (2006).

Maggio. Novel Formulations for Non-Invasive Delivery & Stabilization of Peptides. Drug Development & Delivery 13:68 (2013).

Matsumura et al., Surface activities, biodegradability and antimicrobial properties of n-alkyl glucosides, mannosides and galactosides. Journal of the America Oil Chemists Society 67:996-1001 (1990).

Munjal et al. A Multicenter, Open-Label, Long-Term Safety and Tolerability Study of DFN-02, an Intranasal Spray of Sumatriptan 10 mg plus Permeation Enhancer DDM, for the Acute Treatment of Episodic Migraine. J. Headache Pain 18(1):31 (2017).

Munjal et al., A Randomized Trial Comparing the Pharmacokinetics, Safety, and Tolerability of DFN-02, an Intranasal Sumatriptan Spray Containing a Permeation Enhancer, with Intranasal and Subcutaneous Sumatriptan in Healthy Adults. Headache 56:1455 (2016).

Munjal et al. A Randomized Trial Comparing the Pharmacokinetics, Safety, and Tolerability of DFN-02, an Intranasal Sumatriptan Spray Containing a Permeation Enhancer, with Intranasal and Subcutaneous Sumatriptan in Healthy Adults. headache 56:1455 (2016), https://headachejournal.onlinelibrary.wiley.com/doi/10.1111/head.12905 (last visited Aug. 10, 2021).

Murakami et al. Assessment of Enhancing Ability of Medium-Chain Alkyl Saccharides as New Absorption Enhancers in Rat Rectum. International Journal of Pharmaceutics 79(1-3):159-169 (1992).

Nakponetong et al. Pharmacokinetics Of Epinephrine Absorption via Intranasal Administration: A Preliminary Report. J Allergy Olin Immunol 125(2):Abstract 859 (2010).

National Library of Medicine MARC Record for the Asian Pacific Journal Of Allergy And Immunology (2 pgs.) (Retrieved from internet Aug. 12, 2021).

News Release, Opiant Pharmaceuticals, Inc. Licenses Aegis Therapeutics' Intravail® Drug Delivery Technology (Jun. 28, 2017), https://ir.opiant.com/news-releases/news-release-details/opiant-pharmaceuticals-inc-licenses-aegis-therapeutics (last visited Jul. 29, 2021).

Ozsoy et al. Nasal delivery of high molecular weight drugs. Molecules 14(9):3754-79 (2009).

PAR Pharmaceuticals. Product named "Adrenalin Chloride Nasal Solution (epinephrine nasal solution, USP)" May 1, 2015.

Parish et al. A systematic review of epinephrine degradation with exposure to excessive heat or cold. Ann Allergy Asthma Immunol 117:79-87 (2016).

PCT/US2019/016918 International Search Report and Written Opinion dated Apr. 22, 2019.

Pillion et al. Synthetic long-chain alkyl maltosides and alkyl sucrose esters as enhancers of nasal insulin absorption. J. Pharm. Sci. 91:1456-1462 (2002).

Pires et al. Intranasal Drug Delivery: How, Why and What for? J. Pharm. Pharmaceut. Sci. 12:288-311 (2009).

Pu et al. A Comparison of the Deposition Patterns of Different Nasal Spray Formulations Using a Nasal Cast. Aerosol Science and Technology 48(9):930-938 (2014).

Pumphrey. Lessons for Management of Anaphylaxis from a Study of Fatal Reactions. Clin. & Exper. Allergy 30:1144-1150 (2000).

Rawas-Qalaji et al. Sublingual Epinephrine Tablets Versus Intramuscular Injection of Epinephrine: Dose Equivalence for Potential Treatment of Anaphylaxis, J. Allergy Clin. Immunol. 117:398 (2006).

Rawas-Qalaji. Treatment of Anaphylaxis: Where is the Future? J Develop Drugs 2:1 (2013).

Reber et al. The Pathophysiology of Anaphylaxis. J. Allergy Clin. Immunol. 140:335 (2017).

Riedl et al. Adverse Drug Reactions: Types and Treatment Options. Am. Fam. Physician 68:1781 (2003).

Ring et al. Adrenaline in the Acute Treatment of Anaphylaxis. Dtsch Arztebl Int 115:528 (2018).

Shaver et al. Acute Myocardial Infarction After Administration of Low-Dose Intravenous Epinephrine for Anaphylaxis. Can. J. Emerg. Med. 8(4):289-294 (2006).

Simons. Anaphylaxis, Killer Allergy: Long-Term Management in the Community. J. Allergy Clin. Immunol. 117:367 (2006).

Simons et al. Can Epinephrine Inhalations be Substituted for Epinephrine Injection in Children at Risk for Systemic Anaphylaxis? Pediatrics 106:1040 (2000).

Simons et al. Epinephrine absorption in adults: Intramuscular versus subcutaneous injection. J Allergy Clin Immunol 108:871-3 (2001).

Simons et al. Epinephrine Absorption in Children with a History of Anaphylaxis. J. Allergy Clin. Immunol. 101:33 (1998).

Simons et al. World Allergy Organization Guidelines for the Assessment and Management of Anaphylaxis. World Allergy Organ J 4:13-37 (2011).

Sinnott et al. On the Mechanism by Which Epinephrine Potentiates Lidocaine's Peripheral Nerve Block. Anesthesiology 98:181-188 (2003).

Srisawat et al. A preliminary study of intranasal epinephrine administration as a potential route for anaphylaxis treatment. Asian Pac J Allergy Immunol 34(1):38-43 (2016).

Steed et al. Reduction of Nasal *Staphylococcus aureus* Carriage in Health Care Professionals by Treatment with a Nonantibiotic, Alcohol-Based Nasal Antiseptic. Am. J. Infection Control 42:841-846 (2014).

Türker et al. Nasal route and drug delivery systems. Pharm. World Sci. 26(3):137-42 (2004).

UAB News Release, Aegis Therapeutics Inc. of San Diego Enters Exclusive License Agreement with UAB Research Foundation (Apr. 12, 2004), https://www.uab.edu/newsarchive/42960-aegis-therapeutics-inc-of-san-diego-enters-exclusive-license-agreement-with-uab-research-foundation (last visited Jul. 29, 2021).

University of Chicago Library Catalogue MARC Record for the journal HEADACHE (3 pgs. (no date available), Last access: Apr. 6, 2021.

U.S. Department of Health and Human Services Food and Drug Administration, Center for Drug Evaluation and Research; Guidance for Industry; Nasal Spray and Inhalation Solution, Suspension, and Spray Drug Products—Chemistry, Manufacturing, and Controls Documentation; Jul. 2002, 49 pages; http://www.fda.gov/cder/guidance/index.htm.

U.S. Pat. No. 10,682,414 prosecution history (excerpts) (50 pgs). (Year 2019 to 2020).

U.S. Appl. No. 16/007,999, filed Sep. 27, 2019, Inventors: Roland Schüle & Eric Metzger.

U.S. Pat. No. 10,682,414 Decision Granting Inter Partes Review dated Feb. 14, 2022 (Case No. IPR2021-01324).

U.S. Pat. No. 10,682,414 Judgement. Final Written Decision dated Feb. 9, 2023 (Paper No. 43) (Case No. IPR2021-01324).

(56) References Cited

OTHER PUBLICATIONS

U.S. Pat. No. 10,682,414 Patent Owner's Preliminary Response Pursuant to 37 C.F.R. § 42.107(a) dated Nov. 18, 2021 (Case No. IPR2021-01324).
U.S. Pat. No. 10,682,414 Patent Owner's Response Pursuant to 37 C.F.R. § 42.120(a) dated May 18, 2022 (Case No. IPR2021-01324).
U.S. Pat. No. 10,682,414 Patent Owner's Sur-Reply dated Oct. 10, 2022 (Case No. IPR2021-01324).
U.S. Pat. No. 10,682,414 Patent Owner's Sur-Reply To Petitioner's Reply dated Dec. 23, 2021 (Case No. IPR2021-01324).
U.S. Pat. No. 10,682,414 Petition For Inter Partes Review filed Aug. 12, 2021 (Case No. IPR2021-01324) (83 pgs).
U.S. Pat. No. 10,682,414 Petitioner's Authorized Reply to Patent Owner's Preliminary Response dated Dec. 16, 2021 (Case No. IPR2021-01324).
U.S. Pat. No. 10,682,414 Petitioner's Reply to Patent Owner's Response dated Aug. 24, 2022 (Case No. IPR2021-01324).
Van der Lubben et al. Chitosan and its derivatives in mucosal drug and vaccine delivery. Eur. J. Pharm. Sci. 14(3):201-207 (2001).
Vidgren et al. Nasal delivery systems and their effect on deposition and absorption. Adv. Drug Deliv. Rev. 29:157-77 (1998).
Watanabe et al. Antibacterial Carbohydrate Monoesters Suppressing Cell Growth of Streptoccus mutans in the Presence of Sucrose. Current Microbiology 41(3):210-213 (2000).
Weber. Metabolism of orally administered alkyl beta-glycosides in the mouse. J. Nutr. 114:247-254 (1984).
Williams. Nasal and sublingual spray delivery devices: market opportunities and unmet medical needs. Inhalation Jun. 2016 (pp. 11-15).
Zhao et al., Clinical Pharmacology Considerations in Biologics Development. Acta Pharmacologica Sinica 33:1339-1347 (2012).
Alpha Chemika Product specification for their Adrenaline Bitartrate AR product (downloaded 2023).
EP19751807.9 Communication of a Notice of Opposition dated Jul. 28, 2023.
"Epinephrine hydrochloride" monograph from the Handbook on Injectable Drugs, 19th ed., (pp. 467-473) (2017).
U.S. Appl. No. 62/685,049, filed Jun. 14, 2018; Inventors: Richard Lowenthal & Pratick Shah.
U.S. Appl. No. 15/890,131, filed Feb. 6, 2018; Inventor Edward T. Maggio, published as US-20180169247.
U.S. Appl. No. 15/890,131 Response to Final Action dated Sep. 26, 2019.

* cited by examiner

Figure 1. AUC vs. Time for Intransal Epinephrine as Disclosed in Srisawat *et al.*
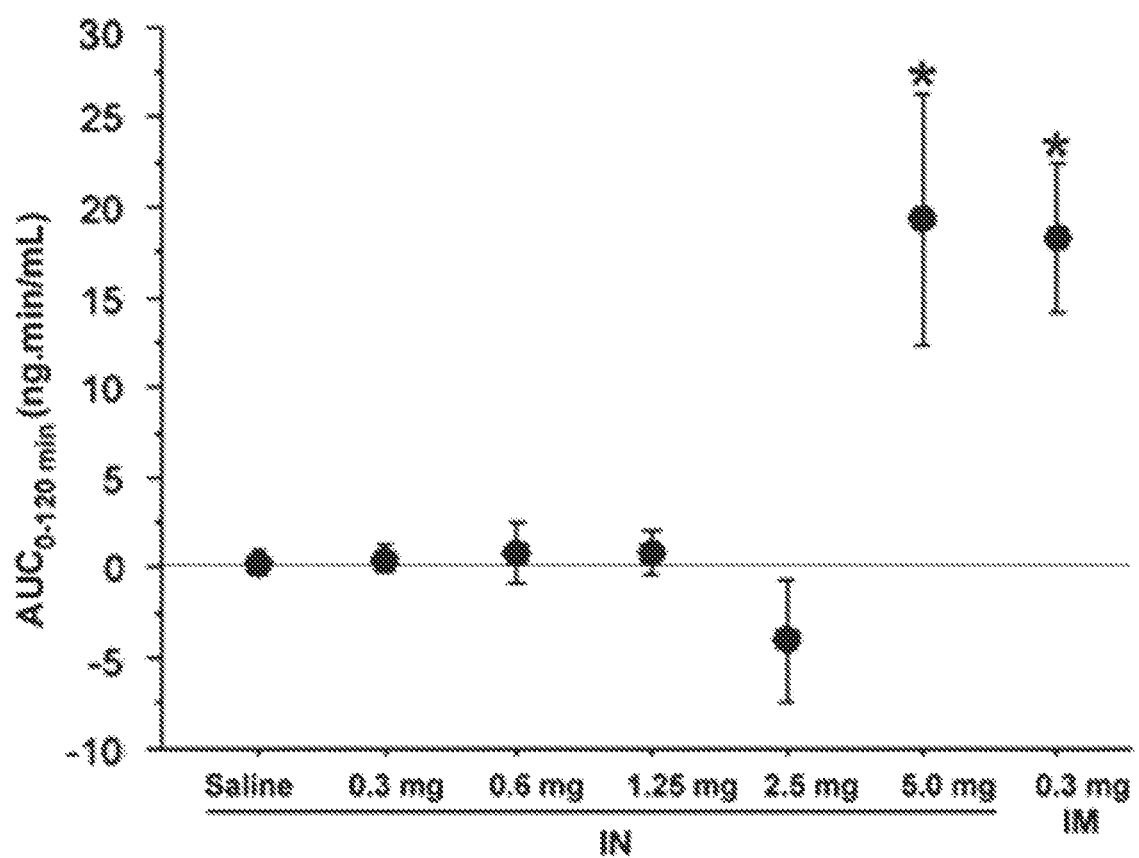

Figure 2. Plasma Epinephrine Concentrations as Disclosed in Srisawat *et al.*
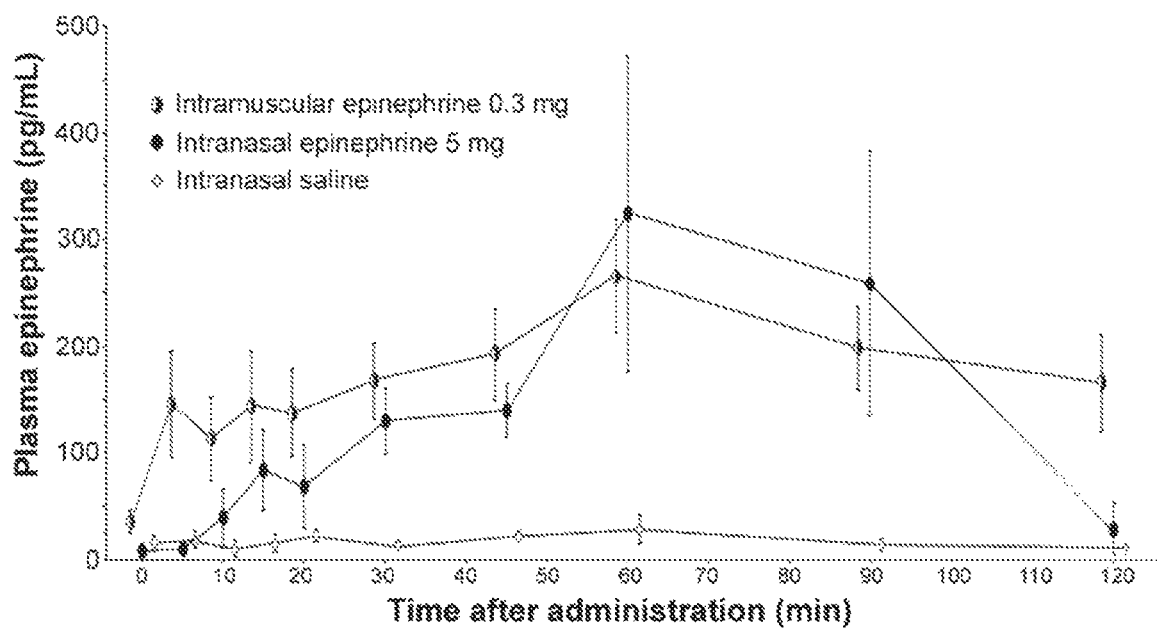

Figure 3. Mean Plasma Epinephrine Concentrations with Intransal Epinephrine Described in Example 2A.
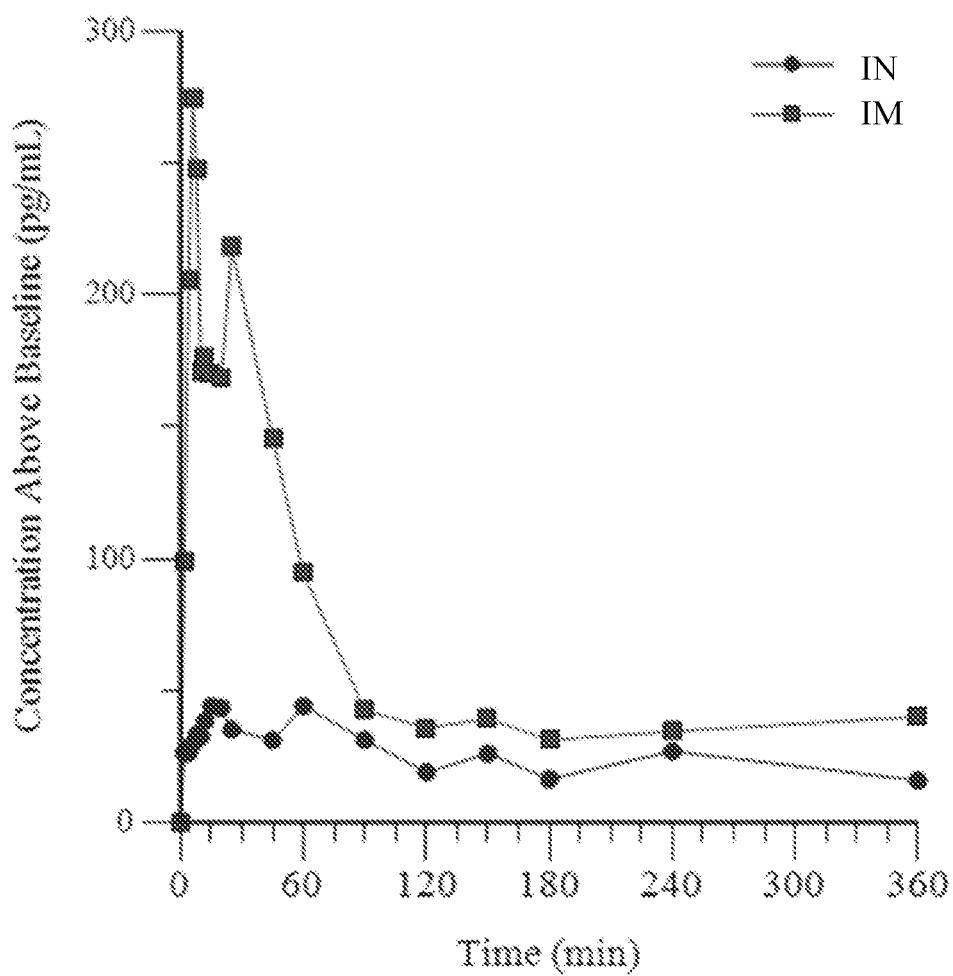

Figure 4. Mean Plasma Epinephrine Concentrations with Intransal Epinephrine Described in Example 2B.
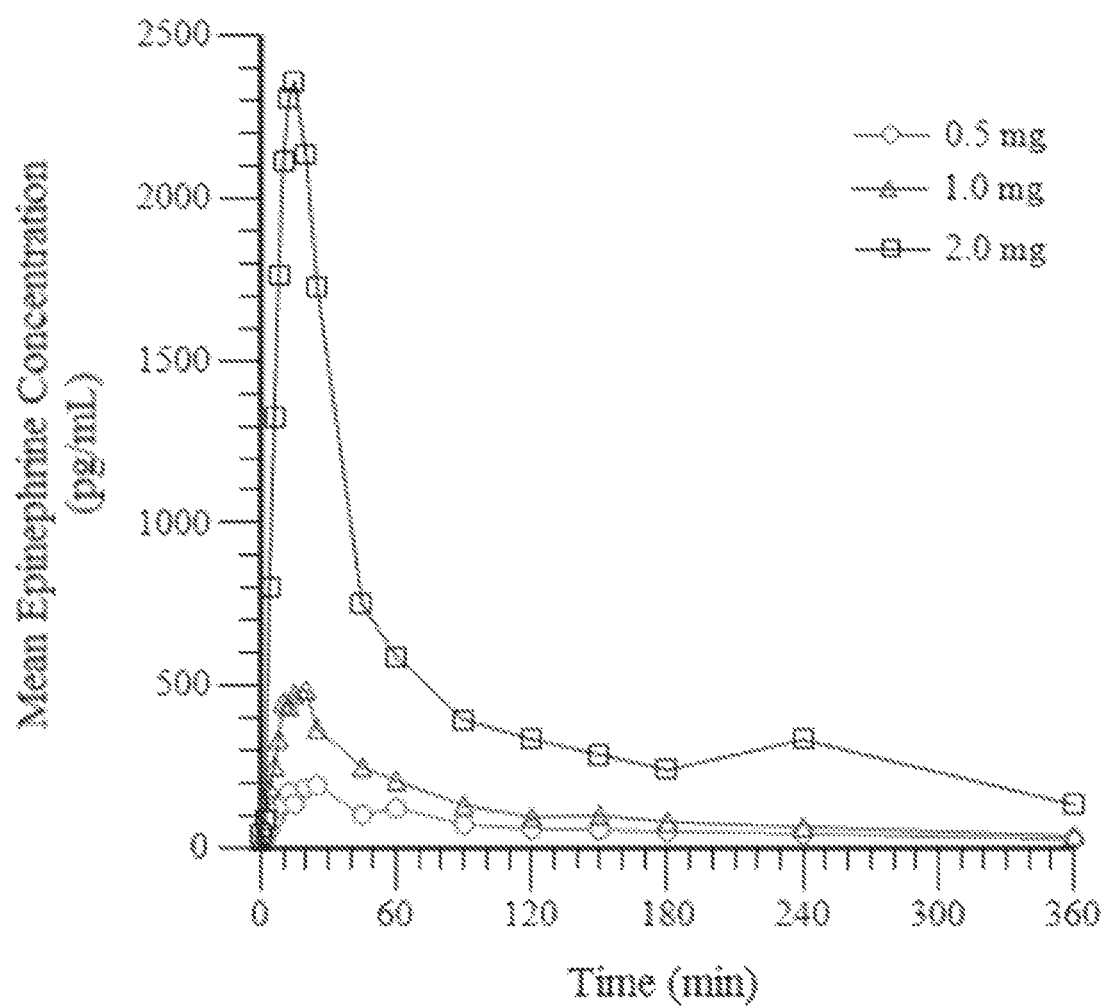

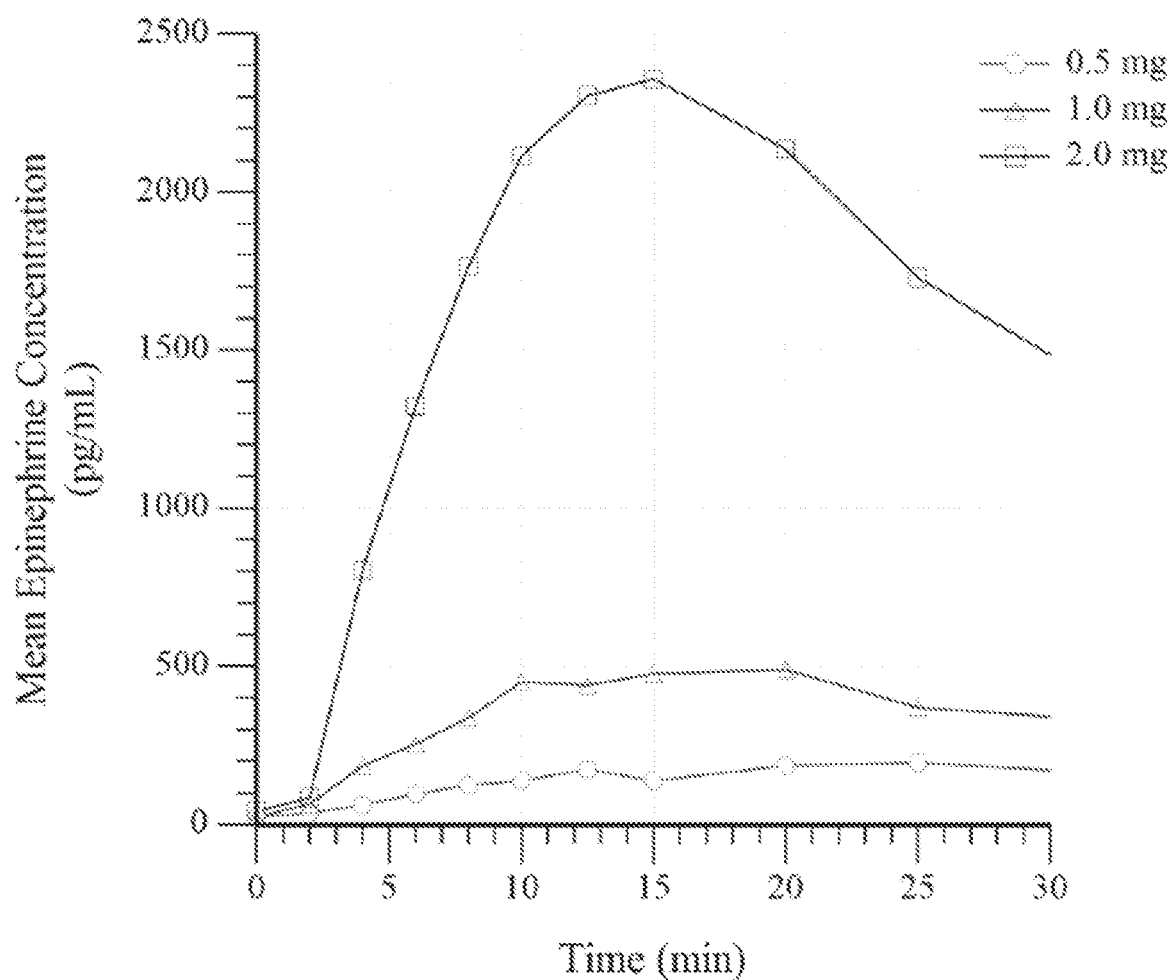
Figure 5. Mean Plasma Epinephrine Concentrations with Intransal Epinephrine Described in Example 2B.

Figure 6. Mean Plasma Epinephrine Concentrations with Intransal Epinephrine Described in Example 2B.
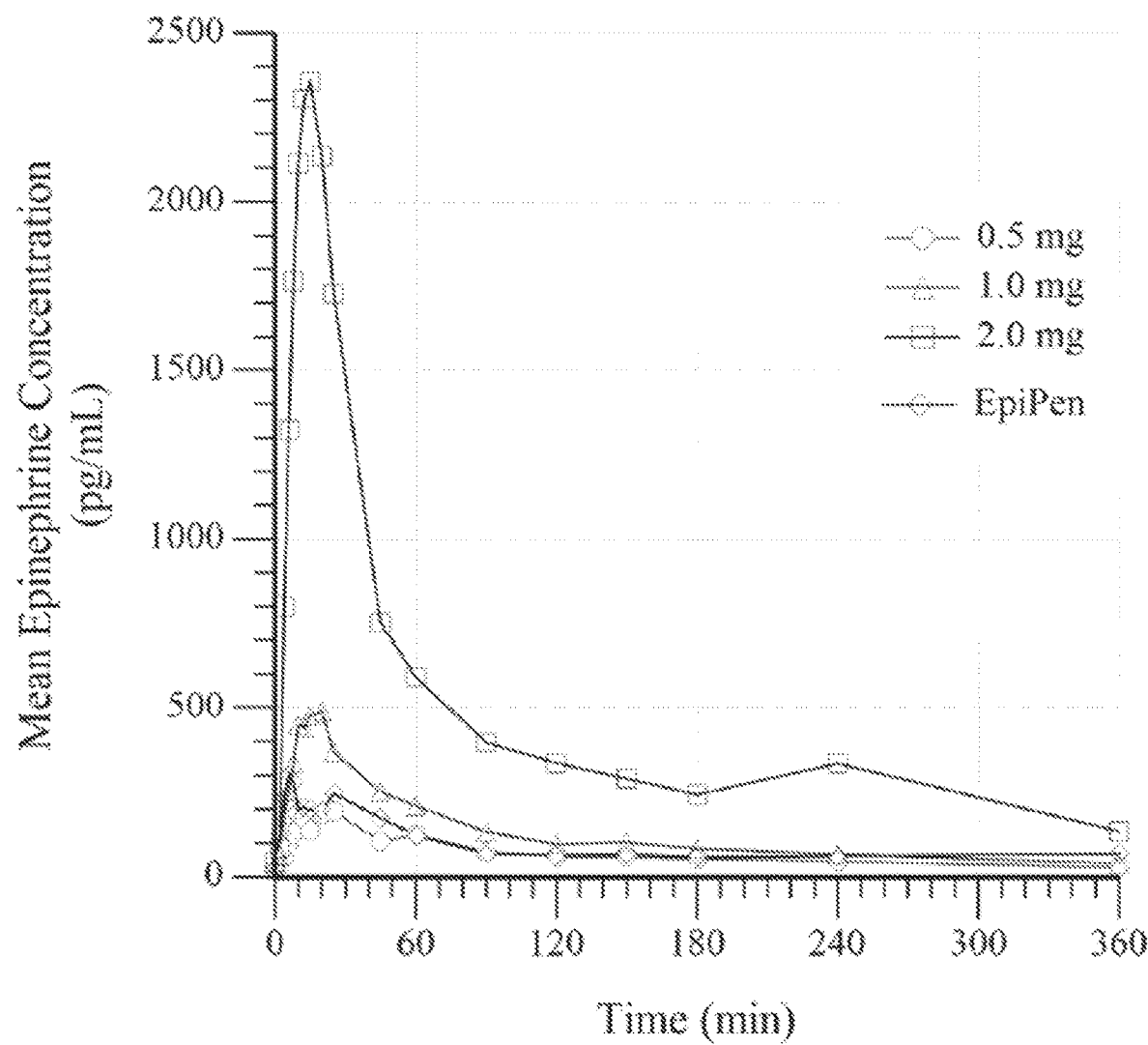

Figure 7. Comparison of Mean Plasma Epinephrine Obtained with Intransal 1.0 mg Epinephrine (Example 2B) and Intramuscular 0.3mg Epinephrine.
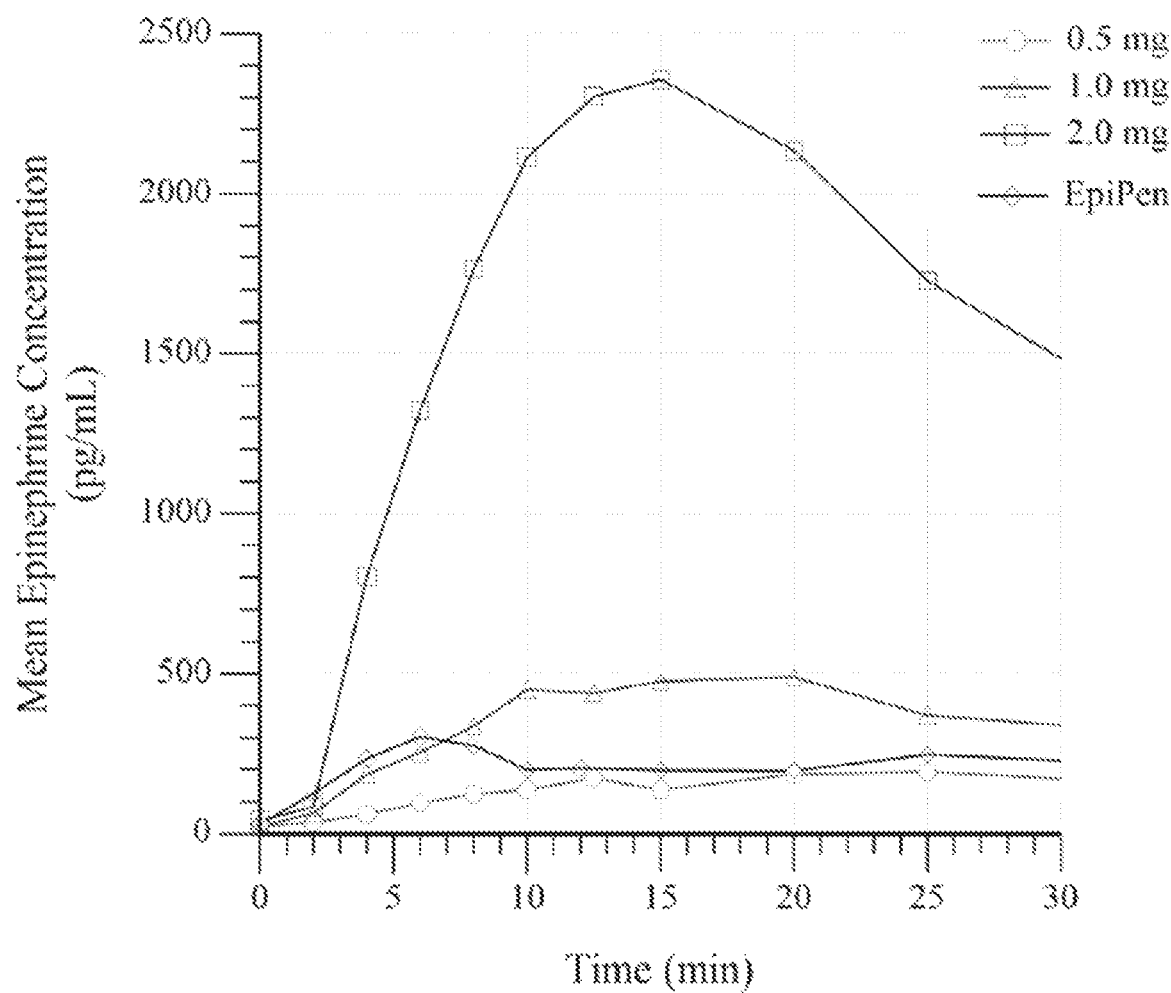

Figure 8. Comparison of Mean Plasma Epinephrine Obtained with Intranasal 1.0 mg Epinephrine (Example 2B) and Intramuscular 0.3mg Epinephrine.
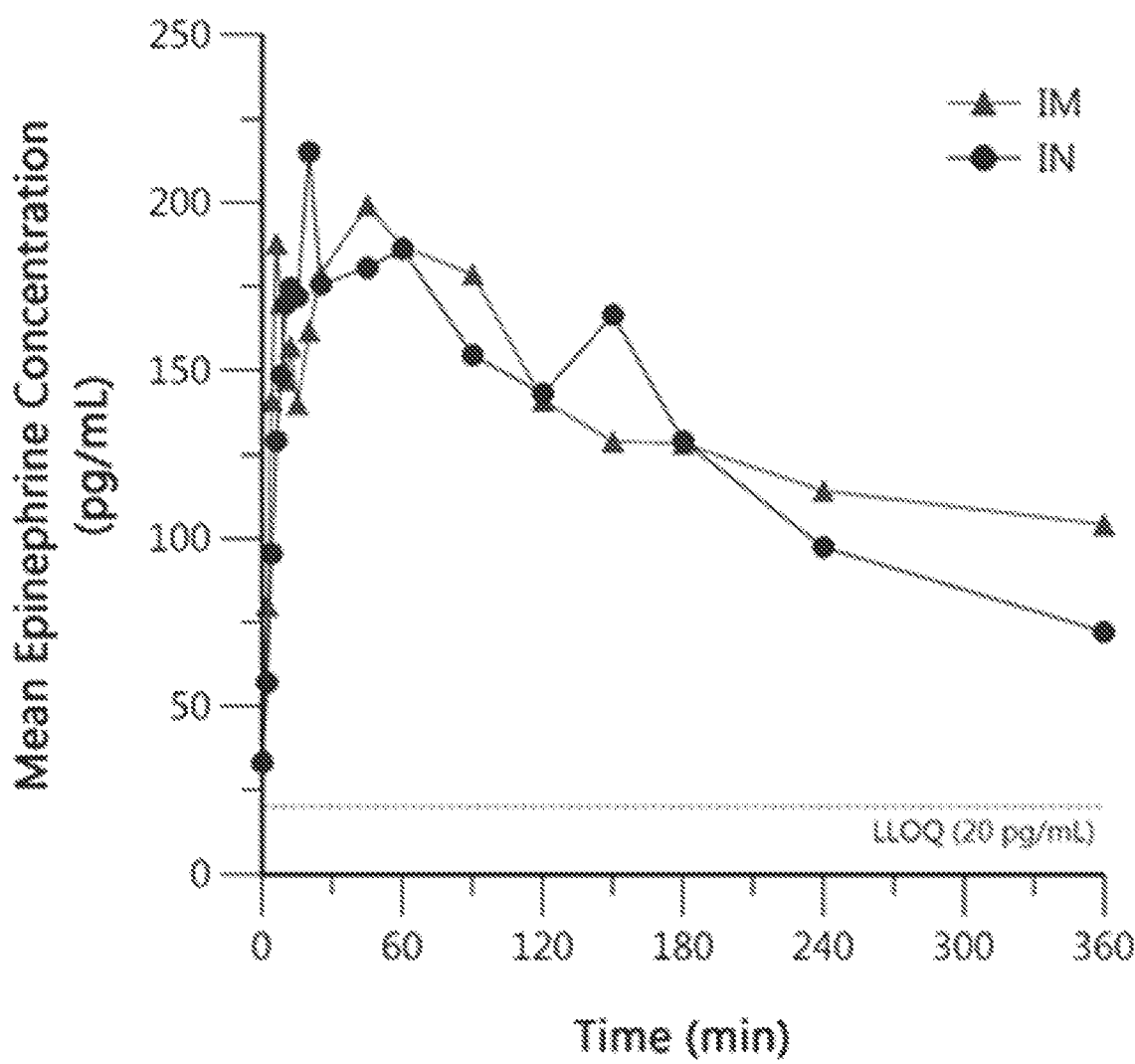

Figure 9. Comparison of Mean Plasma Epinephrine Obtained with Intranasal 1.0 mg Epinephrine (Example 2B) and Intramuscular 0.3 mg Epinephrine.
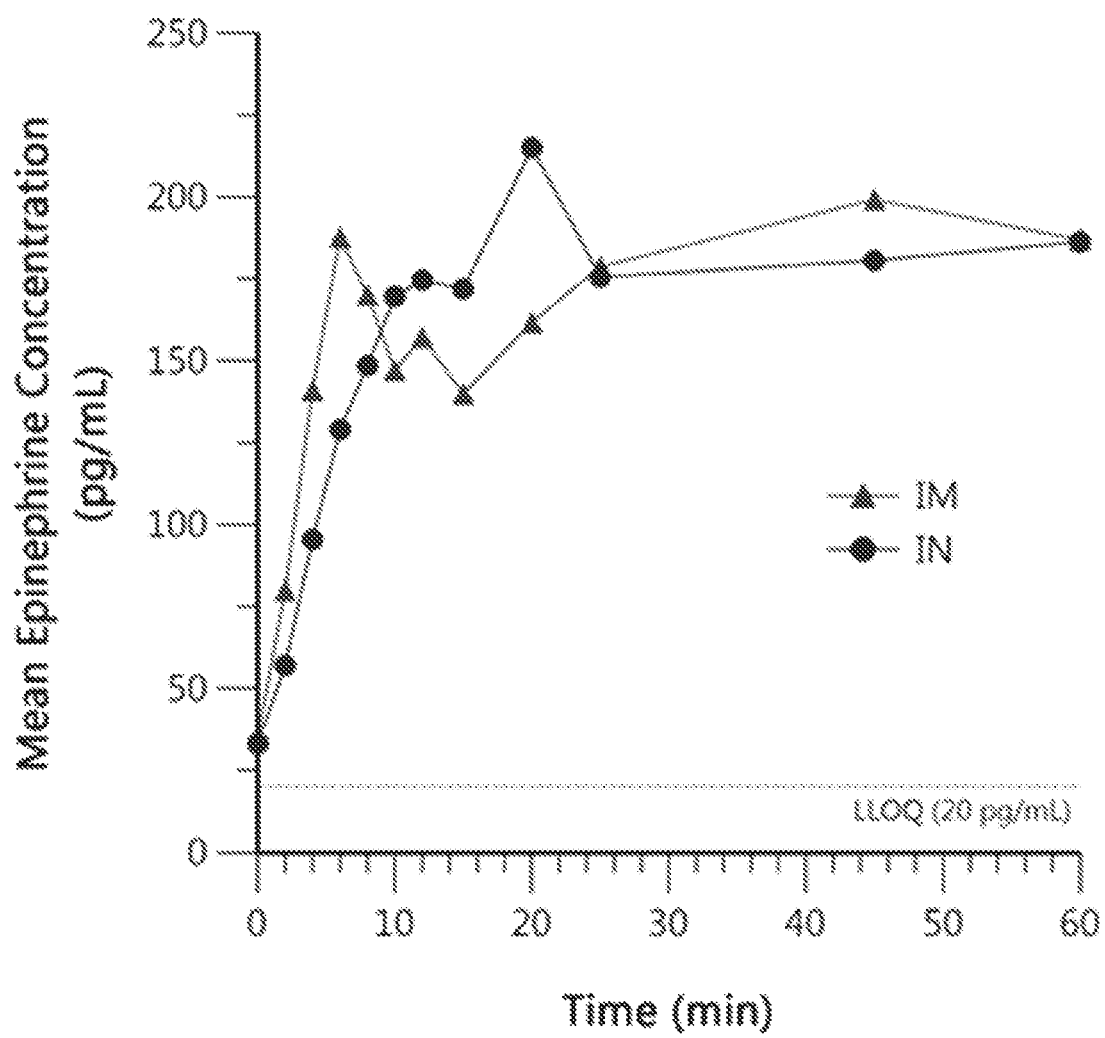

INTRANASAL EPINEPHRINE FORMULATIONS AND METHODS FOR THE TREATMENT OF DISEASE

CROSS REFERENCE

This application is a continuation of U.S. patent application Ser. No. 18/327,621, filed on Jun. 1, 2023, which is a continuation of U.S. patent application Ser. No. 18/049,936, filed on Oct. 26, 2022, now U.S. Pat. No. 11,717,571, issued on Aug. 8, 2023, which is a continuation of U.S. patent application Ser. No. 17/396,044, filed on Aug. 6, 2021, now U.S. Pat. No. 11,744,895, issued on Sep. 5, 2023, which is a continuation of U.S. patent application Ser. No. 16/869,461 filed on May 7, 2020, now U.S. Pat. No. 11,191,838, issued on Dec. 7, 2021, which is a continuation of U.S. patent application Ser. No. 16/420,044 filed on May 22, 2019, now U.S. Pat. No. 10,682,414 issued on Jun. 16, 2020, which is a continuation of International Application No. PCT/US2019/016918 filed on Feb. 6, 2019, which claims the benefit of U.S. Provisional Patent Application No. 62/784,057 filed on Dec. 21, 2018; each of which is incorporated herein by reference in its entirety.

FIELD OF THE INVENTION

Described herein are intranasal (IN) epinephrine formulations and methods of using such formulations in the treatment of conditions or diseases.

BACKGROUND OF THE INVENTION

Anaphylaxis is a medical emergency that may require resuscitation measures such as airway management, supplemental oxygen, large volumes of intravenous fluids, and close monitoring. Administration of epinephrine is the treatment of choice. A need exists for needle-free and non-invasive methods of dosing epinephrine. Provided herein are methods, formulations, and devices for the treatment of anaphylaxis and other conditions.

SUMMARY OF THE INVENTION

Disclosed herein are methods, pharmaceutical formulations of epinephrine and methods of use thereof in the treatment of conditions such as type-1 hypersensitivity reactions (systemic allergic reaction), asthma, and cardiac arrest.

Anaphylaxis is a severe, potentially life-threatening type-1 hypersensitivity reaction (systemic allergic reaction) that affects many body systems, with rapid onset typically averaging between about 5 to 30 minutes after intravenous exposure to an antigen and about 2 hours after oral exposure. Anaphylaxis results from the release of inflammatory mediators and cytokines from mast cells and basophils, typically due to an immunologic reaction, but sometimes due to non-immunologic mechanisms. The most common areas of the body affected include: skin (80-90%), respiratory (70%), gastrointestinal (30-45%), heart and vasculature (10-45%), and central nervous system (10-15%) with usually two or more being involved in a single episode.

Anaphylaxis is a medical emergency that may require resuscitation measures such as airway management, supplemental oxygen, large volumes of intravenous fluids, and close monitoring. Administration of epinephrine is the treatment of choice with antihistamines and steroids (for example, dexamethasone) often used as adjuncts. Due to concerns of biphasic anaphylaxis, a period of in-hospital observation for between 2 and 24 hours is often required for people once they have returned to normal.

Epinephrine (adrenaline, (R)-4-(1-Hydroxy-2-(methylamino)ethyl)benzene-1,2-diol) is the primary treatment for anaphylaxis with no absolute contraindication to its use. Currently epinephrine is administered as a solution given by injection, preferably into the mid anterolateral thigh as soon as anaphylaxis is suspected. The injection may be repeated every 5 to 15 minutes if there is insufficient response. A second dose is needed in 16-35% of episodes, but more than two doses are rarely required. The intramuscular route is preferred over subcutaneous administration because the latter may have delayed epinephrine absorption. However, while only minor adverse effects from epinephrine are reported (tremors, anxiety, headaches, and palpitations) there have been numerous reports of the highly variable exposures from injection products depending on the location of the injection (intramuscular or subcutaneous), and other factors such as body mass index (BMI).

There is a significant need in the medical community to develop products that will help improve the clinical management of anaphylaxis in an out-of-hospital setting. While epinephrine is effective when delivered by intramuscular injection, there is published evidence that the pharmacokinetics are highly variable depending on the site of the injection, whether intramuscular or subcutaneous. There have also been significant product quality problems with approved auto-injectors that utilize complex technologies, resulting in many recalls for these products by the FDA in the United States. Epinephrine auto-injectors, such as EpiPen®, are also cumbersome to carry, and require training and time to properly administer in a potentially life-threatening situation.

The need for alternative, needle-free and non-invasive methods for dosing epinephrine are well-documented, as many patients have a fear of injection and, as a result, are reluctant to use an auto-injector of any kind. Further, the auto-injectors are large and burdensome, so many patients in need do not have an epinephrine injector in their presence at all times. There is also a well-documented reluctance to self-administer a dose in public settings.

Thus, there is a need for improved or alternative methods of dosing epinephrine in an emergency situation, as well as improved or alternative formulations and devices. Desirable improvements include: individually and in combinations, convenience (intranasal versus intramuscular), more rapid administration, more reliable, more consistent dosing, needleless, more discrete to dose in public, and administrable by an untrained individual or non-professional.

Accordingly, provided herein are methods, formulations, and devices for the treatment of anaphylaxis and other conditions comprising administering an intranasal formulation of epinephrine using a small compact unit dose sprayer device.

In one aspect, described herein is a nasal spray pharmaceutical formulation comprising between about 0.40 mg and about 2.4 mg of epinephrine, or a salt thereof. In another aspect, described herein is a nasal spray pharmaceutical formulation comprising between about 0.40 mg and about 2.4 mg of epinephrine, or a salt thereof, in a single dose of the nasal spray pharmaceutical formulation. In another aspect, described herein is a nasal spray pharmaceutical formulation comprising between about 0.40 mg and about 2.4 mg of epinephrine, or a salt thereof, in a single dose nasal spray pharmaceutical formulation. In some embodiments, the nasal spray pharmaceutical formulation comprises between about 0.40 mg and about 2.0 mg of epinephrine, or a salt thereof. In some embodiments, the nasal spray pharmaceutical formulation comprises between about 0.40 mg and about 1.8 mg of epinephrine, or a salt thereof. In some embodiments, a single dose of the nasal spray pharmaceutical formulation comprises between about 0.5 mg and about 2.0 mg of epinephrine, or a salt thereof. In some embodiments, a single dose of the nasal spray pharmaceutical formulation comprises between about 0.5 mg and about 1.5 mg of epinephrine, or a salt thereof. In some embodiments, a single dose of the nasal spray pharmaceutical formulation comprises between about about 0.5 mg and about 0.7 mg of epinephrine, or a salt thereof. In some embodiments, a single dose of the nasal spray pharmaceutical formulation comprises about 1.0 mg of epinephrine, or a salt thereof. In some embodiments, a single dose of the nasal spray pharmaceutical formulation comprises between about 1.3 mg and about 1.5 mg of epinephrine, or a salt thereof. In some embodiments, intranasal administration of a single dose of the nasal spray pharmaceutical formulation to a subject provides a plasma epinephrine concentration that are efficacious for the treatment of an acute hypersensitivity reaction. In some embodiments, the nasal spray pharmaceutical formulation is an aqueous solution, aqueous suspension, aqueous emulsion, non-aqueous solution, non-aqueous suspensions, non-aqueous emulsion, or dry powder.

In one aspect, described herein is a nasal spray formulation comprising between about 0.40 mg and about 2.4 mg per dose of epinephrine, or a salt thereof, dispensed from the device. In some embodiments, described herein is a nasal spray formulation comprising between about 0.5 mg and about 2.0 mg of epinephrine, or a salt thereof, per dose dispensed from the device; between about 0.5 mg and about 1.5 mg of epinephrine, or a salt thereof, per dose dispensed from the device; between about 0.5 mg and about 0.7 mg of epinephrine, or a salt thereof, per dose dispensed from the device; about 1.0 mg of epinephrine, or a salt thereof, per dose dispensed from the device; or between about 1.3 mg and about 1.5 mg of epinephrine, or a salt thereof, per dose dispensed from the device. In some embodiments, a single dose of the the nasal spray formulation when administered intranasally provides plasma epinephrine concentrations that are efficacious for the treatment of an acute hypersensitivity reaction. In some embodiments, the epinephrine or salt thereof is present in the pharmaceutical formulation in an amount efficacious for the treatment of an acute hypersensitivity reaction. In some embodiments, the nasal spray formulation is an aqueous solution, aqueous suspension, aqueous emulsion, non-aqueous solution, non-aqueous suspension or non-aqueous emulsion.

In some embodiments, the nasal spray formulation comprises between about 1 mg/mL and about 40 mg/mL of epinephrine, or a salt thereof, per dose. In some embodiments, the nasal spray formulation comprises between about 5 mg/mL and about 40 mg/mL of epinephrine, or a salt thereof, per dose. In some embodiments, the nasal spray formulation comprises between about 1 mg/mL and about 20 mg/mL of epinephrine, or a salt thereof, per dose. In some embodiments, the nasal spray formulation comprises between about 3 mg/mL and about 20 mg/mL of epinephrine, or a salt thereof, per dose. In some embodiments, the nasal spray formulation comprises between about 3 mg/mL and about 15 mg/mL of epinephrine, or a salt thereof, per dose. In some embodiments, the nasal spray formulation comprises about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine, or a salt thereof, per dose. In some embodiments, a dose of the nasal spray formulation comprises about 100 µL of the nasal spray epinephrine formulation described herein.

In some embodiments, a nasal spray formulation described herein comprises about 1 mg/mL to about 40 mg/mL of epinephrine, or a salt thereof. In some embodiments, a nasal spray formulation described herein comprises about 1 mg/mL to about 20 mg/mL of epinephrine, or a salt thereof. In some embodiments, a nasal spray formulation described herein comprises about 1 mg/mL to about 18 mg/mL of epinephrine, or a salt thereof. In some embodiments, a nasal spray formulation described herein comprises about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine, or a salt thereof. In some embodiments, a nasal spray formulation described herein comprises about about 3 mg/mL, about 5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, or about 15 mg/mL of epinephrine, or a salt thereof. In some embodiments, a nasal spray formulation described herein comprises about about 10 mg/mL of epinephrine, or a salt thereof. In some embodiments, a nasal spray formulation described herein comprises about 6 mg/mL to about 8 mg/mL of epinephrine, or a salt thereof. In some embodiments, a nasal spray formulation described herein comprises about 13 mg/mL to about 15 mg/mL of epinephrine, or a salt thereof. In some embodiments, a dose of the nasal spray formulation comprises about 100 µL of the nasal spray epinephrine formulation described herein.

In some embodiments, a dose of about 100 µL of the nasal spray formulation described herein comprises 1 mg/mL to about 40 mg/mL of epinephrine, or a salt thereof. In some embodiments, a dose of about 100 µL of the nasal spray formulation described herein comprises 1 mg/mL to 20 mg/mL of epinephrine, or a salt thereof. In some embodiments, a dose of about 100 µL of the nasal spray formulation described herein comprises 3 mg/mL, 3.5 mg/mL, 4 mg/mL, 4.5 mg/mL, 5 mg/mL, 6 mg/mL, 6.5 mg/mL, 7 mg/mL, 7.5 mg/mL, 8 mg/mL, 8.5 mg/mL, 9 mg/mL, 9.5 mg/mL, 10 mg/mL, 10.5 mg/mL, 11 mg/mL, 11.5 mg/mL, 12 mg/mL, 12.5 mg/mL, 13 mg/mL, 13.5 mg/mL, 14 mg/mL, 14.5 mg/mL, or 15 mg/mL of epinephrine, or a salt thereof.

In some embodiments, the nasal spray formulation comprises one or more absorption enhancers.

In some embodiments, the nasal spray formulation provides intramuscular (IM)-injection-like pharmacokinetics when IM-injection is dosed in the lateral thigh, or subcutaneous (SC)-like absorption or in between.

In some embodiments, the nasal spray formulation provides intramuscular (IM)-injection-like absorption.

In some embodiments, the nasal spray formulation provides subcutaneous (SC)-like absorption and the SC pharmacokinetic profile has a $C_{max}$ of at least 100 pg/mL and $AUC_{0-240\ min}$ of 150 h*pg/mL.

In some embodiments, intranasal administration of a single dose of the nasal spray pharmaceutical formulation to a subject provides intramuscular (IM)-injection-like absorption.

In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields; a mean $C_{max}$ that is at least 80% of the $C_{max}$ and no more than 150% of the $C_{max}$ that a 0.3 mg intramuscular injection yields; a mean $t_{max}$ of less than 45 minutes; or IM-injection like absorption under optimal dosing conditions in the thigh. In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields; a mean $C_{max}$ that is at least 80% of the $C_{max}$ and no more than 150% of the $C_{max}$ that a 0.3 mg intramuscular injection yields; a mean $t_{max}$ of less than 45 minutes; and IM-injection like absorption under optimal dosing conditions in the thigh.

In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.15 mg intramuscular injection yields; a mean $C_{max}$ that is at least 80% of the $C_{max}$ and no more than 150% of the $C_{max}$ that a 0.15 mg intramuscular injection yields; a mean $t_{max}$ of less than 45 minutes; or IM-injection like absorption under optimal dosing conditions in the thigh. In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.15 mg intramuscular injection yields; a mean $C_{max}$ that is at least 80% of the $C_{max}$ and no more than 150% of the $C_{max}$ that a 0.15 mg intramuscular injection yields; a mean $t_{max}$ of less than 45 minutes; and IM-injection like absorption under optimal dosing conditions in the thigh.

In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.5 mg intramuscular injection yields; a mean $C_{max}$ that is at least 80% of the $C_{max}$ and no more than 150% of the $C_{max}$ that a 0.5 mg intramuscular injection yields; a mean $t_{max}$ of less than 45 minutes; or IM-injection like absorption under optimal dosing conditions in the thigh. In some embodiments, the nasal spray formulation when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.5 mg intramuscular injection yields; a mean $C_{max}$ that is at least 80% of the $C_{max}$ and no more than 150% of the $C_{max}$ that a 0.5 mg intramuscular injection yields; a mean $t_{max}$ of less than 45 minutes; and IM-injection like absorption under optimal dosing conditions in the thigh.

In some embodiments, the nasal spray formulation comprises between about 0.5 and about 1.1 molar equivalents of acid to each mole of epinephrine. In some embodiments, the acid is adipic acid, ammonium chloride, citric acid, acetic acid, hydrochloric acid, lactic acid, phosphoric acid, propionic acid, sulfuric acid or tartaric acid. In some embodiments, the acid is hydrochloric acid. In some embodiments, no base is added to the nasal spray formulation during its preparation. In some embodiments, the nasal spray formulation has a pH between about 2.0 and about 6.0. In some embodiments, the nasal spray formulation has a pH of about 4.0.

In some embodiments, the nasal spray formulation comprises between about 5 mg/mL and about 40 mg/mL per dose epinephrine, or a salt thereof. In some embodiments, the nasal spray formulation comprises between about 0.9 mg and about 2.40 mg per dose dispensed from the device of epinephrine, or a salt thereof. In some embodiments, the nasal spray formulation comprises between about 0.5 mg and about 2.0 mg per dose dispensed from the device of epinephrine, or a salt thereof. In some embodiments, the nasal spray formulation comprises between about 0.9 mg and about 1.5 mg per dose dispensed from the device of epinephrine, or a salt thereof. In some embodiments, the nasal spray formulation comprises between about 0.75 mg and about 1.5 mg per dose dispensed from the device of epinephrine, or a salt thereof. In some embodiments, the nasal spray formulation comprises between about 0.45 mg and about 1.15 mg per dose dispensed from the device of epinephrine, or a salt thereof. In some embodiments, the nasal spray formulation comprises between about 1.0 mg and about 2.0 mg per dose dispensed from the device of epinephrine, or a salt thereof. In some embodiments, the nasal spray formulation comprises between about 0.5 mg and about 2.0 mg of epinephrine, or a salt thereof, per dose dispensed from the device. In some embodiments, the nasal spray formulation comprises between about 0.5 mg and about 1.5 mg of epinephrine, or a salt thereof, per dose dispensed from the device. In some embodiments, the nasal spray formulation comprises between about 0.5 mg and about 0.7 mg of epinephrine, or a salt thereof, per dose dispensed from the device. In some embodiments, the nasal spray formulation comprises about 1.0 mg of epinephrine, or a salt thereof, per dose dispensed from the device. In some embodiments, the nasal spray formulation comprises between about 1.3 mg and about 1.5 mg of epinephrine, or a salt thereof, per dose dispensed from the device.

In some embodiments, the nasal spray pharmaceutical formulation comprises one or more absorption enhancement agents; and optionally one or more agents selected from isotonicity agents; stabilizing agents; preservatives; taste-masking agents; viscosity modifiers; antioxidants; buffers and pH adjustment agents; wherein the pH of the nasal spray pharmaceutical formulation is between about 2.0 and about 6.0.

In some embodiments, the nasal spray pharmaceutical formulation has a pH between about 3.0 and about 5.0. In some embodiments, the nasal spray pharmaceutical formulation has a pH of about 4.0. In some embodiments, the nasal spray pharmaceutical formulation comprises pH adjustment agents. In some embodiments, the pH adjustment agent is an acid, a base, a buffer, or a combination thereof. In some embodiments, the acid is adipic acid, ammonium chloride, citric acid, acetic acid, hydrochloric acid, lactic acid, phosphoric acid, propionic acid, sulfuric acid or tartaric acid; the base is sodium hydroxide, sodium citrate, sodium bicarbonate, sodium carbonate; and the buffer is a phosphate buffer, acetate buffer, or citrate buffer. In some embodiments, the nasal spray pharmaceutical formulation comprises between about 0.5 and about 1.1 molar equivalents of acid to each mole of epinephrine. In some embodiments, the acid is hydrochloric acid.

In some embodiments, the nasal spray formulation comprises one or more absorption enhancers selected from dodecyl maltoside, benzalkonium chloride, oleic acid, or salt thereof, polysorbate 20, polysorbate 80, and sodium lauryl sulfate.

In some embodiments, the formulation comprises one or more absorption enhancers selected from alcohol, aprotinin, benzalkonium chloride, benzyl alcohol, capric acid, ceramides, cetylpyridinium chloride, chitosan, cyclodextrins, deoxycholic acid, decanoyl, dimethyl sulfoxide, glyceryl monooleate, glycofurol, glycofurol, glycosylated sphingosines, glycyrrhetinic acids, 2-hydroxypropyl-β-cyclodextrin, laureth-9, lauric acid, lauroyl carnitine, lysophosphatidylcholine, menthol, poloxamer 407 or F68, poly-L-arginine, polyoxyethylene-9-lauryl ether, isopropyl myristate, isopropyl palmitate, lanolin, light mineral oil, linoleic acid, menthol, myristic acid, myristyl alcohol, oleic acid, or salt thereof, oleyl alcohol, palmitic acid, polysorbate 20, polysorbate 80, propylene glycol, polyoxyethylene alkyl ethers, polyoxylglycerides, pyrrolidone, quillaia saponin, salicylic acid, sodium salt, β-sitosterol β-D-glucoside, sodium lauryl sulfate, sucrose cocoate, taurocholic acid, taurodeoxycholic acid, taurodihydrofusidic acid, thymol, tricaprylin, triolein, and alkylsaccharides.

In some embodiments, the formulation comprises one or more absorption enhancers selected from dodecyl maltoside, benzalkonium chloride, oleic acid, or salt thereof, polysorbate 20, polysorbate 80, and sodium lauryl sulfate.

In some embodiments, the one or more absorption enhancers are: about 0.005% (w/v) to about 2.5% (w/v) dodecyl maltoside; or about 0.001 (w/v) to about 1% (w/v) benzalkonium chloride; or about 0.001 (w/v) to about 1% (w/v) oleic acid, or salt thereof; or a combination of about about 0.005% (w/v) to about 2.5% (w/v) dodecyl maltoside and about 0.001 (w/v) to about 1% (w/v) benzalkonium chloride; or a combination of about about 0.005% (w/v) to about 2.5% (w/v) dodecyl maltoside and about 0.001 (w/v) to about 1% (w/v) oleic acid, or salt thereof; or a combination of about 0.001 (w/v) to about 1% (w/v) benzalkonium chloride and about 0.001 (w/v) to about 1% (w/v) oleic acid, or salt thereof.

In some embodiments, the one or more absorption enhancers are: about 0.005% (w/v) to about 0.08% (w/v) benzalkonium chloride; or about 0.01% (w/v) to about 0.06% (w/v) benzalkonium chloride; or about 0.01% (w/v) to about 0.04% (w/v) benzalkonium chloride; wherein the benzalkonium chloride is the sole absorption enhancement agent in the formulation or is in present in the formulation with one or more additional absorption enhancement agents.

In some embodiments, the formulation comprises a preservative. In some embodiments, the preservative is benzalkonium chloride.

In some embodiments, the nasal spray pharmaceutical formulation comprises an isotonicity agent. In some embodiments, the isotonicity agent is dextrose, glycerin, mannitol, potassium chloride, or sodium chloride. In some embodiments, the isotonicity agent is sodium chloride.

In some embodiments, the nasal spray formulation additionally comprises a stabilizing agent. In some embodiments, the stabilizing agent is ethylenediaminetetraacetic acid (EDTA) or a salt thereof. In some embodiments, the EDTA is disodium EDTA. In some embodiments, the nasal spray formulation comprises from about 0.001% (w/v) to about 1% (w/v) of disodium EDTA.

In some embodiments, the nasal spray formulation additionally comprises a preservative. In some embodiments, the preservative is benzalkonium chloride.

In some embodiments, the nasal spray formulation comprises one or more absorption enhancers selected from alkylglycosides, benzalkonium chloride, oleic acid, or salt thereof, polysorbate 20, polysorbate 80, sodium lauryl sulfate, cyclodextrins, medium and long chain fatty acids, or salts thereof, saturated and unsaturated fatty acids, or salts thereof, alcohol, glycerin, propylene glycol, PEG 300/400, and benzyl alcohol.

In some embodiments, the nasal spray formulation further comprises an antioxidant. In some embodiments, the nasal spray formulation further comprises an antioxidant selected from alpha tocopherol, arachidonic acid, ascorbic acid, ascorbyl palmitate, benzethonium chloride, benzethonium bromide, benzalkonium chloride, butylated hydroxyanisole (BHA), butylated hydroxytoluene (BHT), capric acid, caproic acid, carbon dioxide, cetylpyridium chloride, chelating agents, chitosan derivatives, citric acid monohydrate, dodecyl dimethyl aminopropionate, enanthic acid, erythorbic acid, ethyl oleate, fumaric acid, glycerol oleate, glyceryl monostearate, lauric acid, limonene, linolenic acid, lysine, malic acid, menthol, methionine, monothioglycerol, myristic acid, oleic acid, palmitic acid, pelargonic acid, peppermint oil, phosphoric acid, polysorbates, potassium metabisulfite, propionic acid, propyl gallate, sodium ascorbate, sodium bisulfite, sodium caprate, sodium desoxycholate, sodium deoxyglycolate, sodium formaldehyde sulfoxylate, sodium glycocholate, sodium hydroxybenzoyal amino caprylate, sodium lauryl sulfate, sodium metabisulfite, sodium sulfite, sodium taurocholate, sodium thiosulfate, stearic acid, sulfur dioxide and a combination thereof.

In some embodiments, the nasal spray formulation further comprises synergists with the antioxidants selected from citric acid monohydrate, tartaric acid, thymol, tocopherol (alpha tocopherol), tocopherasol, vitamin E and vitamin E polyethylene glycol succinate and a combination thereof.

In some embodiments, the nasal spray formulation further comprises permeation enhancers selected from alcohol, arachidonic acid, benzethonium chloride, benzethonium bromide, benzalkonium chloride, capric acid, caproic acid, carvone, cetylpyridium chloride, chitosans, citric acid, 6-cyclohexyl-1-hexyl-β-D-maltopyranoside, n-decyl-β-D-maltopyranoside, dimethyl sulfoxide, dodecyl dimethyl aminopropionate, 1-O-n-Dodecyl-β-D-maltopyranoside, dodecylpolyethyleneglycolether, edetate disodium dihydrate, enanthic acid, glyceryl monooleate, glyceryl monostearate, glycofurol, isopropyl myristate, isopropyl palmitate, pelargonic acid, lanolin, lauric acid, light mineral oil, limonene, linoleic acid, lysine, menthol, myristic acid, myristyl alcohol, oleic acid, oleyl alcohol, palmitic acid, peppermint oil, polyoxyethylene alkyl ethers, polyoxylglycerides, polysorbates, pyrrolidone, sodium caprate, sodium desoxycholate, sodium deoxyglycolate, sodium glycocholate, sodium hydroxybenzoyal amino caprylate, sodium lauryl sulfate, sodium taurocholate, stearic acid, thymol, tricaprylin, triolein, undecylenic acid, and a combination thereof.

In some embodiments, the nasal spray formulation comprises: about 0.005% (w/v) to about 2.5% (w/v) dodecyl maltoside; about 0.001 (w/v) to about 1% (w/v) benzalkonium chloride; about 0.001 (w/v) to about 1% (w/v) oleic acid, or salt thereof, a combination of about about 0.005% (w/v) to about 2.5% (w/v) dodecyl maltoside and about 0.001 (w/v) to about 1% (w/v) benzalkonium chloride; a combination of about about 0.005% (w/v) to about 2.5% (w/v) dodecyl maltoside and about 0.001 (w/v) to about 1% (w/v) oleic acid, or salt thereof, or a combination of about 0.001 (w/v) to about 1% (w/v) benzalkonium chloride and about 0.001 (w/v) to about 1% (w/v) oleic acid, or salt thereof: or a combination of about 0.001 (w/v) to about 1% (w/v) benzalkonium chloride and about 0.001 (w/v) to about 1% (w/v) oleic acid, or salt thereof and 0.001% to 1% sodium metabisulfite; or a combination of about 0.001 (w/v) to about 1% (w/v) benzalkonium chloride and about 0.001 (w/v) to about 1% (w/v) oleic acid, or salt thereof and about 0.001% to 10% polysorbate 80 and 0.001% to 1% sodium metabisulfite; or a combination of about 0.001 (w/v) to about 1% (w/v) benzalkonium chloride and about 0.001 (w/v) to about 1% (w/v) oleic acid, or salt thereof and about 0.001% to 10% polysorbate 80 and 0.001% to 1% sodium metabisulfite and 0.001% to 1% citric acid.

In some embodiments, the nasal spray formulation comprises: about 0.005% (w/v) to about 0.08% (w/v) benzalkonium chloride; about 0.01% (w/v) to about 0.06% (w/v) benzalkonium chloride; or about 0.01% (w/v) to about 0.04% (w/v) benzalkonium chloride; wherein the benzalkonium chloride is the sole absorption enhancement agent in the nasal spray formulation or is in present in the formulation with one or more additional absorption enhancement agents.

In some embodiments, the nasal spray formulation comprises: about 0.001% to 1% of any one of the antioxidants described herein, or a combination of any one of the antioxidants described herein.

In some embodiments, the nasal spray formulation comprises a buffering agent. Buffering agents include, but are not limited to, adipic acid, boric acid, calcium carbonate, calcium hydroxide, calcium lactate, calcium phosphate, tribasic, citric acid monohydrate, dibasic sodium phosphate, diethanolamine, glycine, maleic acid, malic acid, methionine, monobasic sodium phosphate, monoethanolamine, monosodium glutamate, phosphoric acid, potassium citrate, sodium acetate, sodium bicarbonate, sodium borate, sodium carbonate, sodium citrate dihydrate, sodium hydroxide, sodium lactate, and triethanolamine.

In one aspect, provided herein is a method of treatment of a condition mediated by adrenergic receptors comprising the intranasal administration of any one of the formulations as described herein. In some embodiments, the condition is chosen from a type-1 hypersensitivity reaction (systemic allergic reaction), an acute asthmatic attack, cardiac arrest, and Stokes-Adams Syndrome. In some embodiments, the condition is a type-1 hypersensitivity reaction (systemic allergic reaction). In some embodiments, the type 1 hypersensitivity reaction is chosen from allergic asthma, allergic conjunctivitis, allergic rhinitis, anaphylaxis, angioedema, urticaria, eosinophilia, drug allergy and food allergy. In some embodiments, the drug allergy is an antibiotic allergy.

In one aspect, described herein is a nasal spray formulation comprising epinephrine or a salt thereof, which when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields; a mean $C_{max}$ that is at least 80% of the $C_{max}$ and no more than 150% of the $C_{max}$ that a 0.3 mg intramuscular injection yields; a mean $t_{max}$ of less than 45 minutes; or IM-injection like absorption under optimal dosing conditions in the thigh. In another aspect, described herein is a nasal spray formulation comprising epinephrine or a salt thereof, which when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields; a mean $C_{max}$ that is at least 80% of the $C_{max}$ and no more than 150% of the $C_{max}$ that a 0.3 mg intramuscular injection yields; a mean $t_{max}$ of less than 45 minutes; and IM-injection like absorption under optimal dosing conditions in the thigh.

In another aspect, described herein is a nasal spray formulation comprising epinephrine or a salt thereof, which when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.15 mg intramuscular injection yields; a mean $C_{max}$ that is at least 80% of the $C_{max}$ and no more than 150% of the $C_{max}$ that a 0.15 mg intramuscular injection yields; a mean $t_{max}$ of less than 45 minutes; or IM-injection like absorption under optimal dosing conditions in the thigh. In another aspect, described herein is a nasal spray formulation comprising epinephrine or a salt thereof, which when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.15 mg intramuscular injection yields; a mean $C_{max}$ that is at least 80% of the $C_{max}$ and no more than 150% of the $C_{max}$ that a 0.15 mg intramuscular injection yields; a mean $t_{max}$ of less than 45 minutes; and IM-injection like absorption under optimal dosing conditions in the thigh.

In yet another aspect, described herein is a nasal spray formulation comprising epinephrine or a salt thereof, which when administered to a subject yields one or more of the following pharmacokinetic features: both the mean $AUC_{0\text{-}20\ min}$ and $AUC_{0\text{-}t}$ are at least 80% of the $AUC_{0\text{-}20\ min}$ and $AUC_{0\text{-}t}$ that a 0.5 mg intramuscular injection yields; a mean $C_{max}$ that is at least 80% of the $C_{max}$ and no more than 150% of the $C_{max}$ that a 0.5 mg intramuscular injection yields; a mean $t_{max}$ of less than 45 minutes; or IM-injection like absorption under optimal dosing conditions in the thigh.

In some embodiments, the nasal spray formulation is a pharmaceutical formulation.

In some embodiments, the epinephrine or salt thereof is present in the nasal spray formulation in an amount efficacious for the treatment of an acute hypersensitivity reaction.

In some embodiments, intranasal administration of a single dose of the nasal spray pharmaceutical formulation to a subject provides a plasma epinephrine concentration that is efficacious for the treatment of an acute hypersensitivity reaction. In some embodiments, a single dose of the nasal spray pharmaceutical formulation comprises between about 0.5 mg and about 2.0 mg of epinephrine, or a salt thereof. In some embodiments, a single dose of the nasal spray pharmaceutical formulation comprises between about 0.5 mg and about 1.5 mg of epinephrine, or a salt thereof. In some embodiments, a single dose of the nasal spray pharmaceutical formulation comprises between about about 0.5 mg and about 0.7 mg of epinephrine, or a salt thereof. In some embodiments, a single dose of the nasal spray pharmaceutical formulation comprises about 1.0 mg of epinephrine, or a salt thereof. In some embodiments, a single dose of the nasal spray pharmaceutical formulation comprises between about 1.3 mg and about 1.5 mg of epinephrine, or a salt thereof. In some embodiments, the formulation is an aqueous solution, aqueous suspension, aqueous emulsion, non-aqueous solution, non-aqueous suspension, non-aqueous emulsion, pressurized metered-dose inhalers or dry powder.

In some embodiments, the nasal spray formulation is an aqueous solution, aqueous suspensions, aqueous emulsion, non-aqueous solution, non-aqueous suspension or non-aqueous emulsion.

In some embodiments, the nasal spray formulation has intramuscular (IM)-injection-like pharmacokinetics when IM-injection is dosed in the lateral thigh, or subcutaneous (SC)-like absorption or in between.

In some embodiments, the nasal spray formulation has subcutaneous (SC)-like absorption and the SC pharmacokinetic profile has a $C_{max}$ of at least 100 pg/mL and AUC0-240 min of 150 h*pg/mL.

In some embodiments, the nasal spray formulation has intramuscular (IM)-injection-like absorption.

In some embodiments, the nasal spray formulation comprises an absorption enhancer.

In some embodiments, the nasal spray pharmaceutical formulation comprises one or more absorption enhancement agents; and optionally one or more agents selected from isotonicity agents; stabilizing agents; preservatives; taste-masking agents; viscosity modifiers; antioxidants; buffers and pH adjustment agents; wherein the pH of the nasal spray pharmaceutical formulation is between about 2.0 and about 6.0. In some embodiments, the nasal spray pharmaceutical formulation has a pH between about 3.0 and about 5.0. In some embodiments, the nasal spray pharmaceutical formulation has a pH of about 4.0.

In some embodiments, the nasal spray pharmaceutical formulation comprises pH adjustment agents. In some embodiments, the pH adjustment agent is an acid, a base, a buffer, or a combination thereof. In some embodiments, the acid is adipic acid, ammonium chloride, citric acid, acetic acid, hydrochloric acid, lactic acid, phosphoric acid, propionic acid, sulfuric acid or tartaric acid; the base is sodium hydroxide, sodium citrate, sodium bicarbonate, sodium carbonate; and the buffer is a phosphate buffer, acetate buffer, or citrate buffer.

In some embodiments, the nasal spray formulation comprises between about 0.5 and about 1.1 molar equivalents of acid to each mole of epinephrine. In some embodiments, the acid is is adipic acid, ammonium chloride, citric acid, acetic acid, hydrochloric acid, lactic acid, phosphoric acid, propionic acid, sulfuric acid or tartaric acid. In some embodiments, the acid is hydrochloric acid. In some embodiments, no base is added to the formulation during its preparation. In some embodiments, the nasal spray formulation has a pH between about 2.0 and about 6.0. In some embodiments, the nasal spray formulation has a pH of about 4.0.

In some embodiments, the nasal spray formulation comprises between about 5 mg/mL and about 40 mg/mL per dose epinephrine, or a salt thereof. In some embodiments, the nasal spray formulation comprises between about 0.40 mg and about 2.40 mg per dose dispensed from the device of epinephrine, or a salt thereof. In some embodiments, the nasal spray formulation comprises between about 0.9 mg and about 2.40 mg per dose dispensed from the device of epinephrine, or a salt thereof. In some embodiments, the nasal spray formulation comprises between about 0.5 mg and about 2.0 mg per dose dispensed from the device of epinephrine, or a salt thereof. In some embodiments, the nasal spray formulation comprises between about 0.9 mg and about 1.5 mg per dose dispensed from the device of epinephrine, or a salt thereof. In some embodiments, the nasal spray formulation comprises between about 0.75 mg and about 1.5 mg per dose dispensed from the device of epinephrine, or a salt thereof. In some embodiments, the nasal spray formulation comprises between about 0.45 mg and about 1.15 mg per dose dispensed from the device of epinephrine, or a salt thereof. In some embodiments, the nasal spray formulation comprises between about 1.0 mg and about 2.0 mg per dose dispensed from the device of epinephrine, or a salt thereof.

In some embodiments, the nasal spray formulation comprises one or more absorption enhancers selected from alcohol, aprotinin, benzalkonium chloride, benzyl alcohol, capric acid, ceramides, cetylpyridinium chloride, chitosan, cyclodextrins, deoxycholic acid, decanoyl, dimethyl sulfoxide, glyceryl monooleate, glycofurol, glycofurol, glycosylated sphingosines, glycyrrhetinic acids, 2-hydroxypropyl-β-cyclodextrin, laureth-9, lauric acid, lauroyl carnitine, lysophosphatidylcholine, menthol, poloxamer 407 or F68, poly-L-arginine, polyoxyethylene-9-lauryl ether, isopropyl myristate, isopropyl palmitate, lanolin, light mineral oil, linoleic acid, menthol, myristic acid, myristyl alcohol, oleic acid, oleyl alcohol, palmitic acid, polysorbate 20, polysorbate 80, propylene glycol, polyoxyethylene alkyl ethers, polyoxylglycerides, pyrrolidone, quillaia saponin, salicylic acid, sodium salt, β-sitosterol β-D-glucoside, sodium lauryl sulfate, sucrose cocoate, taurocholic acid, taurodeoxycholic acid, taurodihydrofusidic acid, thymol, tricaprylin, triolein, and alkylsaccharides.

In some embodiments, the nasal spray formulation comprises one or more absorption enhancers selected from dodecyl maltoside, benzalkonium chloride, oleic acid, or salt thereof, polysorbate 20, polysorbate 80, and sodium lauryl sulfate.

In some embodiments, the nasal spray formulation comprises: about 0.005% (w/v) to about 2.5% (w/v) dodecyl maltoside; about 0.001 (w/v) to about 1% (w/v) benzalkonium chloride; about 0.001 (w/v) to about 1% (w/v) oleic acid, or salt thereof, a combination of about about 0.005% (w/v) to about 2.5% (w/v) dodecyl maltoside and about 0.001 (w/v) to about 1% (w/v) benzalkonium chloride; a combination of about about 0.005% (w/v) to about 2.5% (w/v) dodecyl maltoside and about 0.001 (w/v) to about 1% (w/v) oleic acid, or salt thereof, or a combination of about 0.001 (w/v) to about 1% (w/v) benzalkonium chloride and about 0.001 (w/v) to about 1% (w/v) oleic acid, or salt thereof and about 0.001 to 1% of an antioxidant (e.g. sodium metabisulfite). In some embodiments, the nasal spray formulation comprises: about 0.005% (w/v) to about 2.5% (w/v) dodecyl maltoside; about 0.001 (w/v) to about 1% (w/v) benzalkonium chloride; about 0.001 (w/v) to about 1% (w/v) oleic acid, or salt thereof, a combination of about about 0.005% (w/v) to about 2.5% (w/v) dodecyl maltoside and about 0.001 (w/v) to about 1% (w/v) benzalkonium chloride; a combination of about about 0.005% (w/v) to about 2.5% (w/v) dodecyl maltoside and about 0.001 (w/v) to about 1% (w/v) oleic acid, or salt thereof, or a combination of about 0.001 (w/v) to about 1% (w/v) benzalkonium chloride and about 0.001 (w/v) to about 1% (w/v) oleic acid, or salt thereof. In some embodiments, the nasal spray formulation comprises: about 0.005% (w/v) to about 0.08% (w/v) benzalkonium chloride; about 0.01% (w/v) to about 0.06% (w/v) benzalkonium chloride; or about 0.01% (w/v) to about 0.04% (w/v) benzalkonium chloride; wherein the benzalkonium chloride is the sole absorption enhancement agent in the nasal spray formulation or is in present in the formulation with one or more additional absorption enhancement agents.

In some embodiments, the nasal spray formulation additionally comprises a stabilizing agent. In some embodiments, the stabilizing agent is ethylenediaminetetraacetic acid (EDTA) or a salt thereof. In some embodiments, the EDTA is disodium EDTA. In some embodiments, the EDTA is present in an amount that is from about 0.001% to about 1%.

In some embodiments, the nasal spray formulation additionally comprises a preservative. In some embodiments, the preservative is benzalkonium chloride.

In one aspect, described herein is a method of treatment of a condition mediated by adrenergic receptors comprising the intranasal administration of any one of the formulation described herein. In some embodiments, the condition is chosen from a type-1 hypersensitivity reaction (systemic allergic reaction), an acute asthmatic attack, cardiac arrest, and Stokes-Adams Syndrome. In some embodiments, the condition is a type-1 hypersensitivity reaction (systemic allergic reaction). In some embodiments, the type 1 hypersensitivity reaction is chosen from allergic asthma, allergic conjunctivitis, allergic rhinitis, anaphylaxis, angioedema, urticaria, eosinophilia, drug allergy and food allergy. In some embodiments, the drug allergy is an antibiotic allergy.

In another aspect, described herein is a method of treatment of anaphylaxis comprising the intranasal administration of an intranasal formulation of epinephrine in an amount less than about 2.0 mg. In some embodiments, the nasal pharmaceutical formulation comprises between about 0.5 mg and about 1.5 mg of epinephrine, or a salt thereof. In some embodiments, the nasal pharmaceutical formulation comprises between about about 0.5 mg and about 0.7 mg of epinephrine, or a salt thereof. In some embodiments, the nasal pharmaceutical formulation comprises about 1.0 mg of epinephrine, or a salt thereof. In some embodiments, the nasal pharmaceutical formulation comprises between about 1.3 mg and about 1.5 mg of epinephrine, or a salt thereof.

In some embodiments of the methods of treatments, the intranasal formulation comprises: one or more absorption enhancement agents; an isotonicity agent; a stabilizing agent; a preservative; an optional antioxidant; and optional pH adjustment agents. In some embodiments of the methods of treatment, the one or more absorption enhancement agents are selected from: dodecyl maltoside; benzalkonium chloride; oleic acid, or salt thereof, sodium laural sulfate; a combination of dodecyl maltoside and benzalkonium chloride; a combination of dodecyl maltoside and oleic acid, or salt thereof, and a combination of benzalkonium chloride and oleic acid, or salt thereof. In some embodiments of the methods of treatment, the one or more absorption enhancement agents are selected from: about 0.005% (w/v) to about 2.5% (w/v) dodecyl maltoside; about 0.001 (w/v) to about 1% (w/v) benzalkonium chloride; about 0.001 (w/v) to about 1% (w/v) oleic acid, or salt thereof, a combination of about about 0.005% (w/v) to about 2.5% (w/v) dodecyl maltoside and about 0.001 (w/v) to about 1% (w/v) benzalkonium chloride; a combination of about about 0.005% (w/v) to about 2.5% (w/v) dodecyl maltoside and about 0.001 (w/v) to about 1% (w/v) oleic acid, or salt thereof, or a combination of about 0.001 (w/v) to about 1% (w/v) benzalkonium chloride and about 0.001 (w/v) to about 1% (w/v) oleic acid, or salt thereof. In some embodiments of the methods of treatment, the formulation comprises: about 0.005% (w/v) to about 0.08% (w/v) benzalkonium chloride; about 0.01% (w/v) to about 0.06% (w/v) benzalkonium chloride; or about 0.01% (w/v) to about 0.04% (w/v) benzalkonium chloride; wherein the benzalkonium chloride is the sole absorption enhancement agent in the formulation or is in present in the formulation with one or more absorption enhancement agents. In some embodiments of the methods of treatment, the isotonicity agent is sodium chloride. In some embodiments of the methods of treatment, the stabilizing agent is EDTA. In some embodiments of the methods of treatment, the stabilizing agent is EDTA in an amount from about 0.001% (w/v) to about 1% (w/v). In some embodiments of the methods of treatment, the preservative is benzalkonium chloride. In some embodiments of the methods of treatment, the preservative is benzalkonium chloride in an amount from about 0.001% (w/v) to about 1% (w/v).

Articles of manufacture, which include packaging material, a nasal spray formulation described herein within the packaging material, and a label that indicates that the nasal spray formulation is used for the treatment of any of the conditions described herein (e.g. anaphylaxis) are provided.

Other objects, features and advantages of the compositions and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

BRIEF DESCRIPTION OF FIGURES

FIG. 1 shows the area under the plasma concentration versus time curve at time 0-120 minutes ($AUC_{0-120\ min}$) of epinephrine absorption at different dosages and routes of administration as disclosed in Srisawat et al., "A preliminary study of intranasal epinephrine administration as a potential route for anaphylaxis treatment," *Asian Pac J Allergy Immunol,* 2016 March; 34(1):38-43, discussed below.

FIG. 2 shows the plasma epinephrine concentration versus time plots after administrations of IN saline, IN epinephrine at 5 mg, and IM epinephrine at 0.3 mg, as disclosed in Srisawat et al.

FIG. 3 shows the mean plasma epinephrine concentrations above baseline (pg/mL) vs. time (min) curves from the first clinical study described in Example 2A comparing 0.3 mg epinephrine IM and IN; the curve with squared represents IM, and the curve with circles, IN.

FIG. 4 shows the mean plasma epinephrine concentrations above baseline (pg/mL) vs. time (min) curves from the second clinical study described in Example 2B comparing 0.5, 1.0, and 2.0 mg epinephrine IN. The curve with circles represents 0.5 mg; the curve with triangles, 1.0 mg, and the curve with squares, 2.0 mg.

FIG. 5 shows the first 30 minutes of the mean plasma epinephrine concentrations above baseline (pg/mL) vs. time (min) curves from the second clinical study described in Example 2B comparing 0.5, 1.0, and 2.0 mg IN epinephrine. The curve with circles represents 0.5 mg; the curve with triangles, 1.0 mg, and the curve with squares, 2.0 mg.

FIG. 6 repeats the data from FIG. 4 and overlays it with the mean plasma concentration vs. time curve for IM epinephrine from the first clinical study described in Example 2A.

FIG. 7 repeats the data from FIG. 5 and overlays it with the first 30 minutes of the mean plasma concentration vs. time curve for IM epinephrine from the first clinical study described in Example 2A.

FIG. 8 shows the mean plasma epinephrine concentrations above baseline (pg/mL) vs. time (min) curves from the comparative bioavailability portion of the second clinical study described in Example 2B, comparing 1.0 mg epinephrine IN (curve w/circles) to 0.3 mg epinephrine IM (epinephrine auto injector, curve w/triangles).

FIG. 9 shows the first 30 minutes of the mean plasma epinephrine concentrations above baseline (pg/mL) vs. time (min) curves from the comparative bioavailability portion of the second clinical study described in Example 2B, comparing 1.0 mg epinephrine IN (curve w/circles) to 0.3 mg epinephrine IM (EpiPen®, curve w/triangles).

DETAILED DESCRIPTION

Disclosed herein are methods and formulations useful for the treatment of anaphylaxis and other conditions, comprising administering an intranasal formulation of epinephrine. Also provided are devices adapted for nasal delivery of a pharmaceutical formulation to a patient, including single, bi- and multidose delivery comprising a therapeutically effective amount of epinephrine and pharmaceutically acceptable salts thereof.

Intranasal epinephrine has a long history of use in low doses as a decongestant and as a vasoconstrictor, often formulated combination with anaesthetic, in sinus and nasal surgery. Historically, epinephrine has been difficult to formulate as an intranasal solution for systemic delivery. See, e.g., Srisawat C et al., "A preliminary study of intranasal epinephrine administration as a potential route for anaphylaxis treatment," Asian Pac J Allergy Immunol, 2016 March; 34(1):38-43. Srisawat showed that significant systemic absorption of epinephrine via the IN route was observed only at 5 mg (see FIG. 1) and the pharmacokinetic parameters of IN epinephrine even at 5 mg were also not significantly different from those of the IM epinephrine group (see Table 1, below).

TABLE 1

Intramuscular and Intranasal Administraton of Epinephrine (from Srisawat (2016).

| Mean ± SD | Intramuscular (IM) Epinephrine 0.3 mg | Intranasal (IN) Epinephrine 5 mg |
|---|---|---|
| $C_{baseline}$ (pg/mL) | 35 ± 23 | 8 ± 6 |
| $C_{max}$ (pg/mL) | 309 ± 88 | 386 ± 152 |
| $T_{max}$ (min) | 67 ± 43 | 70 ± 17 |
| $AUC_{0-120\ min}$ (ng*min/mL) | 18.3 ± 9.3 | 19.4 ± 12.1 |

FIG. 1 is reproduced from Srisawat C et al. and demonstrates that Srisawat et al. observed no blood level of epinephrine at the intranasal dose level of 2.5 mg and below.

Furthermore, FIG. 2 shows that even at a dose of 5 mg, Srisawat was not able to make an intranasal formulation that could achieve a higher plasma concentration than intramuscular epinephrine delivered by auto injector at any time point before about 60 minutes, thus absorption during the critical early time points was delayed when rapid absorption is needed to stop the systemic allergic reaction (anaphylaxis). This is potentially detrimental in serious conditions such as anaphylaxis where immediate treatment, and thus injection-like pharmacokinetics, are desirable. The PK profile of IM injection into the thigh is considered the optimal dosing method by literature given that the higher vascularity of the leg muscle allows for more rapid absorption and distribution of the epinephrine providing a rapid increase in plasma levels to stop the anaphylaxis reaction much sooner than other routes of administration. FIG. 2 also shows that Srisawat's 5 mg formulation, in contrast to intramuscular epinephrine delivered by auto injector, cleared from the plasma almost entirely in about two hours. Finally, epinephrine is known to be associated with dose-related cardiac side effects including myocardial infarction, at doses as low as 0.3 to 0.5 mg intramuscularly; accordingly, doses as high as 5 mg would likely be risky in the general population if nasal conditions existed that may allow excessive absorption. Thus, lower dose preparations that would avoid such risks are preferred as a safer nasal preparation.

Disclosed herein are intranasal formulations of epinephrine, and nasal spray devices comprising the formulations, that solve the problems of past attempts. Various aspects may contribute to the success of the formulations, devices, and methods of use disclosed herein.

For example, in certain embodiments, formulating epinephrine in an aqueous solution with the appropriate addition of molar equivalents of acid to each mole of said epinephrine helps to solubilize and stabilize the epinephrine. This allows the formulation to avoid the use of buffering agents commonly used in aqueous pharmaceutical compositions for injection, including phosphate, acetate, and citrate buffers, which are sometimes avoided in the nasal formulations disclosed herein. Other salts of epinephreine, such as epinephrine acetate, epinephrine hydrochloride, epinephrine tartrate, epinephrine bitartrate, epinephrine hydrogen tartrate and epinephrine borate can also be used to formulate aqueous solutions of epinephrine.

Certain embodiments of the formulations, devices, and methods of use disclosed herein offer advantages over epinephrine formulated in other ways. Epinephrine is considered a narrow therapeutic index drug. As a sympathomimetic catecholamine, epinephrine has a narrow therapeutic index and serious adverse reactions including cardiovascular and cerebrovascular reactions can be associated with its use. Nevertheless, the use epinephrine for this indication is life saving and the benefits of using it outweigh the potential safety risks. Intranasal delivery and formulation are suited for the safe, painless delivery of drugs such as epinephrine by consistent content uniformity, delivery amount and absorption, thereby minimizing serious adverse reactions including cardiovascular and cerebrovascular reactions that can be associated with its use via injection mechanisms. Shot weights have low variability and consistently deliver the labeled dose.

In one aspect, described herein is a pharmaceutical composition comprising: a) epinephrine; and b) an alkylglycoside; wherein the pharmaceutical composition is formulated for administration into the circulatory system of a subject via the intranasal, inhalation, or pulmonary, administration route. In some embodiments, described herein is a pharmaceutical composition comprising: a) epinephrine; and b) an alkylglycoside; wherein the pharmaceutical composition is a liquid formulated for intranasal delivery.

In some embodiments, the alkylglycoside has an alkyl chain including between 8 to 20 carbons. In some embodiments, the alkylglycoside is selected from the group consisting of undecyl maltoside, dodecyl maltoside, tridecyl maltoside, tetradecyl maltoside, sucrose mono-dodecanoate, sucrose mono-tridecanoate, and sucrose mono-tetradecanoate. In some embodiments, the alkylglycoside is dodecyl-beta-D-maltoside. In some embodiments, the alkylglycoside concentration is between about 0.001% and 10.0% (w/v). In some embodiments, the alkylglycoside concentration is between about 0.05% and 0.5% (w/v).

In some embodiments, the composition further comprises a membrane penetration-enhancing agent. In some embodiments, the membrane penetration-enhancing agent is a surfactant, a bile salt, a phospholipid, an alcohol, an enamine, a long-chain amphipathic molecule, a small hydrophobic molecule, sodium or a salicylic acid derivative, a glycerol ester of acetoacetic acid, a cyclodextrin, a medium-chain or long chain fatty acids, a chelating agent, an amino acid or salt thereof, an enzyme or combination thereof. In some embodiments, the membrane penetration-enhancing agent is selected from the group consisting of citric acid, sodium citrate, propylene glycol, glycerin, ascorbic acid, sodium metabisulfite, ethylenediaminetetraacetic acid (EDTA) disodium, benzalkonium chloride, hydroxyquinolone, sodium hydroxide, and combinations thereof. In some embodiments, the membrane penetration-enhancing agent is selected from the group consisting of citric acid, sodium citrate, propylene glycol, glycerin, ascorbic acid, sodium metabisulfite, ethylenediaminetetraacetic acid (EDTA) disodium, benzalkonium chloride, sodium hydroxide, and combinations thereof. In some embodiments, membrane penetration-enhancing agent is benzalkonium chloride, EDTA, or a combination thereof.

In some embodiments, the composition provides a Cmax for the epinephrine in a subject that is about 2 fold or greater as compared to administration without alkylglycoside.

In some embodiments, the composition provides a Tmax for the epinephrine in a subject that is about 2 fold or less as compared to administration without alkylglycoside.

In some embodiments, the composition provides a Tmax for the epinephrine of about 0.3 hours or less in a subject.

In some embodiments, the composition has a pH of about 2.0 to 6.0. In some embodiments, the composition has a pH of about 2.0 to 5.0.

In another aspect, described herein is a method of increasing the bioavailability of epinephrine in a subject comprising administering to a subject a pharmaceutical composition comprising epinephrine and an alkylglycoside, thereby increasing the bioavailability of the epinephrine in the subject; wherein the pharmaceutical composition is formulated for administration into the circulatory system of a subject via the intranasal, inhalation, or pulmonary, administration route. In some embodiments, described herein is a method of increasing the bioavailability of epinephrine in a subject comprising administering to a subject a pharmaceutical composition comprising epinephrine and an alkylglycoside, thereby increasing the bioavailability of the epinephrine in the subject; wherein the pharmaceutical composition is a liquid formulated for intranasal delivery.

In some embodiments, increasing the bioavailabilty of epinephrine permits for lower dose amounts of epeinpehrine to be delivered intrasally and be efficacious for treating anaphylaxis. In some embodiments, exposure to larger doses of epinephrine can result in an epinephrine overdose. There is increased interest and need in developing alternative non-invasive epinephrine dosage forms that provide epinephrine plasma concentrations equivalent to those obtained by epinephrine auto-injectors, available in a range of doses, have a long shelf-life, and be free from needle anxiety, the possibility of administration error, unintentional injection and injury. Epinephrine nasal dosage forms described herein offer the potential of being user-friendly, non-invasive alternatives for the first-aid emergency treatment of anaphylaxis in community settings.

In some embodiments, the alkylglycoside has an alkyl chain including between 8 to 20 carbons. In some embodiments, the alkylglycoside is selected from the group consisting of undecyl maltoside, dodecyl maltoside, tridecyl maltoside, tetradecyl maltoside, sucrose mono-dodecanoate, sucrose mono-tridecanoate, and sucrose mono-tetradecanoate. In some embodiments, the alkylglycoside is dodecyl-beta-D-maltoside. In some embodiments, the alkylglycoside concentration is between about 0.001% and 10.0% (w/v). In some embodiments, the alkylglycoside concentration is between about 0.05% and 0.5% (w/v).

In some embodiments, the composition further comprises a membrane penetration-enhancing agent. In some embodiments, the membrane penetration-enhancing agent is a surfactant, a bile salt, a phospholipid, an alcohol, an enamine, a medium and/or long-chain amphipathic molecules, a small hydrophobic molecule, sodium or a salicylic acid derivative, a glycerol ester of acetoacetic acid, a cyclodextrin, a medium-chain or long chain fatty acids, a chelating agent, an amino acid or salt thereof, an enzyme or combination thereof. In some embodiments, the membrane penetration-enhancing agent is selected from the group consisting of citric acid, sodium citrate, propylene glycol, glycerin, ascorbic acid, sodium metabisulfite, ethylenediaminetetraacetic acid (EDTA) disodium, benzalkonium chloride, sodium hydroxide, and combinations thereof. In some embodiments, the membrane penetration-enhancing agent is benzalkonium chloride, EDTA, or a combination thereof.

In some embodiments, the composition provides a Cmax for the epinephrine in the subject that is about 2 fold or greater as compared to administration without alkylglycoside.

In some embodiments, the composition provides a Tmax for the epinephrine in the subject that is about 2 fold or less as compared to administration without alkylglycoside.

In some embodiments, the composition provides a Tmax for the epinephrine of about 0.3 hours or less in the subject.

In some embodiments, the composition has a pH of about 2.0 to 6.0. In some embodiments, the composition has a pH of about 2.0 to 5.0.

In some embodiments, compositions described here are liquid compositions suitable for intranasal administration.

In one aspect, the invention provides a method of increasing absorption of epinephrine into the circulatory system of a subject by administering, via the nasal, inhalation or pulmonary delivery route a composition comprising: (a) epinephrine; (b) an absorption increasing amount of a suitable nontoxic, nonionic alkylglycoside having a hydrophobic alkyl group joined by a linkage to a hydrophilic saccharide; and (c) a mucosal delivery-enhancing agent.

The term, "mucosal delivery-enhancing agent" includes agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of a compound(s) (e.g., biologically active compound). Enhancement of mucosal delivery can occur by any of a variety of mechanisms, including, for example, by increasing the diffusion, transport, persistence or stability of the compound, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junction physiology, reducing the viscosity of mucus overlying the mucosal epithelium, reducing mucociliary clearance rates, and other mechanisms.

Exemplary mucosal delivery enhancing agents include the following agents and any combinations thereof:
  (a) an aggregation inhibitory agent;
  (b) a charge-modifying agent;
  (c) a pH control agent;
  (d) a degradative enzyme inhibitory agent;
  (e) a mucolytic or mucus clearing agent;
  (f) a ciliostatic agent;
  (g) a membrane penetration-enhancing agent selected from:
    (i) a surfactant;
    (ii) a bile salt;
    (ii) a phospholipid additive, mixed micelle, liposome, or carrier;
    (iii) an alcohol;
    (iv) an enamine;

(v) an NO donor compound;
(vi) a long-chain amphipathic molecule;
(vii) a small hydrophobic penetration enhancer;
(viii) sodium or a salicylic acid derivative;
(ix) a glycerol ester of acetoacetic acid;
(x) a cyclodextrin or beta-cyclodextrin derivative;
(xi) a medium-chain fatty acid;
(xii) a chelating agent;
(xiii) an amino acid or salt thereof;
(xiv) an N-acetylamino acid or salt thereof;
(xv) an enzyme degradative to a selected membrane component;
(ix) an inhibitor of fatty acid synthesis;
(x) an inhibitor of cholesterol synthesis; and
(xi) any combination of the membrane penetration enhancing agents recited in (i)-(x);
(h) a modulatory agent of epithelial junction physiology;
(i) a vasodilator agent;
(j) a selective transport-enhancing agent; and
(k) a stabilizing delivery vehicle, carrier, mucoadhesive, support or complex-forming species with which the compound is effectively combined, associated, contained, encapsulated or bound resulting in stabilization of the compound for enhanced nasal mucosal delivery, wherein the formulation of the compound with the intranasal delivery-enhancing agents provides for increased bioavailability of the compound in a blood plasma of a subject.

Additional mucosal delivery-enhancing agents include, for example, citric acid, sodium citrate, propylene glycol, glycerin, ascorbic acid (e.g., L-ascorbic acid), sodium metabisulfite, ethylenediaminetetraacetic acid (EDTA) disodium, benzalkonium chloride, sodium hydroxide, and mixtures thereof. For example, EDTA or its salts (e.g., sodium or potassium) are employed in amounts ranging from about 0.01% to 2% by weight of the composition containing alkylsaccharide preservative.

In yet another aspect, described herein is a pharmaceutical composition having a suitable nontoxic, nonionic alkylglycoside having a hydrophobic alkyl group joined by a linkage to a hydrophilic saccharide in combination with a mucosal delivery-enhancing agent selected from:
(a) an aggregation inhibitory agent;
(b) a charge-modifying agent;
(c) a pH control agent;
(d) a degradative enzyme inhibitory agent;
(e) a mucolytic or mucus clearing agent;
(f) a ciliostatic agent;
(g) a membrane penetration-enhancing agent selected from:
(i) a surfactant;
(ii) a bile salt;
(ii) a phospholipid additive, mixed micelle, liposome, or carrier;
(iii) an alcohol;
(iv) an enamine;
(v) an NO donor compound;
(vi) a long-chain amphipathic molecule;
(vii) a small hydrophobic penetration enhancer;
(viii) sodium or a salicylic acid derivative;
(ix) a glycerol ester of acetoacetic acid;
(x) a cyclodextrin or beta-cyclodextrin derivative;
(xi) a medium-chain or long chain fatty acid;
(xii) a chelating agent;
(xiii) an amino acid or salt thereof;
(xiv) an N-acetylamino acid or salt thereof;
(xv) an enzyme degradative to a selected membrane component;
(ix) an inhibitor of fatty acid synthesis;
(x) an inhibitor of cholesterol synthesis; and
(xi) any combination of the membrane penetration enhancing agents recited in (i)-(x);
(h) a modulatory agent of epithelial junction physiology;
(i) a vasodilator agent;
(j) a selective transport-enhancing agent; and
(k) a stabilizing delivery vehicle, carrier, mucoadhesive, support or complex-forming species with which the compound is effectively combined, associated, contained, encapsulated or bound resulting in stabilization of the compound for enhanced nasal mucosal delivery, wherein the formulation of the compound with the intranasal delivery-enhancing agents provides for increased bioavailability of the compound in a blood plasma of a subject.

In another embodiment, described herein is a method of administering an alkylglycoside composition by administering a therapeutically effective amount of at least one alkyglycoside having an alkyl chain length from about 12 to about 14 carbon atoms, at least one saccharide with an antibacterial activity, and epinephrine.

In one aspect, provided herein is an antibacterial alkylsaccharide composition, which includes n-dodecyl-4-O-α-D-glucopyranosyl-β-D-glucopyranoside or n-tetradecyl-4-O-α-D-glucopyranosyl-β-D-glucopyranoside.

Accordingly, provided herein is Embodiment 1, a nasal spray formulation comprising between about 0.40 mg and about 2.40 mg per dose dispensed from the device of epinephrine, or a salt thereof. Alternative Embodiment 1, a nasal spray formulation comprising between about 0.40 mg and about 2.0 mg per dose dispensed from the device of epinephrine, or a salt thereof.

Embodiment 2. The nasal spray formulation as recited in Embodiment 1, wherein the formulation is a pharmaceutical formulation.

Embodiment 3. The nasal spray formulation as recited in Embodiment 2, wherein the epinephrine or salt thereof is present in the pharmaceutical formulation in an amount efficacious for the treatment of an acute hypersensitivity reaction.

Embodiment 4. The nasal spray formulation as recited in any of Embodiments 1-3, wherein the formulation is aqueous.

Embodiment 5 The nasal spray formulation as recited in any of Embodiments 1-4, wherein the formulation comprises an absorption enhancer. In alternative Embodiment 5, the nasal spray formulation as recited in any of Embodiments 1-4, wherein the formulation comprises one or more absorption enhancers.

Embodiment 6. The nasal spray formulation as recited in any of Embodiments 1-5, wherein the formulation has intramuscular (IM)-injection-like or subcutaneous (SQ)-like absorption, or in between.

Embodiment 7. The nasal spray formulation as recited in Embodiment 6, wherein has intramuscular (IM)-injection-like absorption.

Embodiment 8. The nasal spray formulation as recited in Embodiment 6, wherein the formulation has subcutaneous (SC)-like absorption.

Embodiment 9. The nasal spray formulation as recited in Embodiment 8 where the SC pharmacokinetic profile has a $C_{max}$ of at least 100 pg/mL and $AUC_{0-240\ min}$ of 150 h*pg/mL.

Embodiment 10. The nasal spray formulation as recited in any of Embodiments 1-9, wherein the formulation, when administered to a subject, yields one or more of the following pharmacokinetic features:
both the mean $AUC_{0-20\ min}$ and $AUC_{0-t}$ are at least 80% of the $AUC_{0-20\ min}$ and $AUC_{0-t}$ that a 0.3 mg intramuscular injection yields;
a mean $C_{max}$ that is at least 80% of the $C_{max}$ and no more than 150% of the $C_{max}$ that a 0.3 mg intramuscular injection yields;
a mean $t_{max}$ of less than 45 minutes; and
IM-injection like absorption under optimal dosing conditions in the thigh.

Embodiment 11. The nasal spray formulation as recited in any of Embodiments 1-9, wherein the formulation, when administered to a subject, yields one or more of the following pharmacokinetic features:
both the mean $AUC_{0-20\ min}$ and $AUC_{0-t}$ are at least 80% of the $AUC_{0-20\ min}$ and $AUC_{0-t}$ that a 0.15 mg intramuscular injection yields;
a mean $C_{max}$ that is at least 80% of the Cmax and no more than 150% of the Cmax that a 0.15 mg intramuscular injection yields;
a mean tmax of less than 45 minutes; and
IM-injection like absorption under optimal dosing conditions in the thigh.

Embodiment 12. The nasal spray formulation as recited in any of Embodiments 1-9, wherein the formulation, when administered to a subject, yields one or more of the following pharmacokinetic features:
both the mean $AUC_{0-20\ min}$ and $AUC_{0-t}$ are at least 80% of the $AUC_{0-20\ min}$ and $AUC_{0-t}$ that a 0.5 mg intramuscular injection yields;
a mean $C_{max}$ that is at least 80% of the Cmax and no more than 150% of the Cmax that a 0.5 mg intramuscular injection yields;
a mean tmax of less than 45 minutes; and
IM-injection like absorption under optimal dosing conditions in the thigh.

Embodiment 13. The nasal spray formulation as recited in Embodiment 1-12, wherein the formulation, when administered to a subject, yields a $t_{max}$ of less than 40 minutes, a $t_{max}$ of less than 35 minutes, a $t_{max}$ of between 30 and 45 minutes, a $t_{max}$ of between 30 and 40 minutes, or a $t_{max}$ of between 30 and 35 minutes. Alternative Embodiment 13. The nasal spray formulation as recited in Embodiment 1-12, wherein the formulation, when administered to a subject, yields a $t_{max}$ of less than 40 minutes, a $t_{max}$ of less than 35 minutes, a $t_{max}$ of between 15 and 45 minutes, a $t_{max}$ of between 20 and 45 minutes, a $t_{max}$ of between 25 and 45 minutes, a $t_{max}$ of between 30 and 45 minutes, a $t_{max}$ of between 30 and 40 minutes, a $t_{max}$ of between 30 and 35 minutes, a $t_{max}$ of between 15 and 20 minutes, a $t_{max}$ of between 15 and 25 minutes, or a $t_{max}$ of between 15 and 30 minutes.

Embodiment 14. The nasal spray formulation as recited in any of Embodiments 1-13, wherein the formulation comprises less than one molar equivalents of acid to each mole of epinephrine.

Embodiment 15. The nasal spray formulation as recited in any of Embodiments 1-13, wherein the formulation comprises between about 0.5 and about 1.1 molar equivalents of acid to each mole of epinephrine.

Embodiment 16. The nasal spray formulation as recited in either of Embodiments 14 and 15, wherein the acid is hydrochloric acid. Alternative Embodiment 16, The nasal spray formulation as recited in either of Embodiments 14 and 15, wherein the acid is acetic acid, adipic acid, ammonium chloride, boric acid, citric acid, hydrochloric acid, lactic acid, phosphoric acid, propionic acid, sulfuric acid, or tartaric acid.

Embodiment 17. The nasal spray formulation as recited in any of Embodiments 1-16, wherein the formulation has a pH between about 3.0 and about 6.0. Alternative Embodiment 17. The nasal spray formulation as recited in any of Embodiments 1-16, wherein the formulation has a pH between about 2.0 and about 6.0.

Embodiment 18. The nasal spray formulation as recited in Embodiment 17, wherein the formulation has a pH between about 3.5 and about 5.0.

Embodiment 19. The nasal spray formulation as recited in Embodiment 17, wherein the formulation has a pH between about 4.0 and about 4.5.

Embodiment 20. The nasal spray formulation as recited in Embodiment 17, wherein the formulation has a pH of about 4.5.

Embodiment 21. The nasal spray formulation as recited in Embodiment 17, wherein the formulation has a pH of about 4.0.

Embodiment 22. The nasal spray formulation as recited in any of Embodiments 1-21, wherein the formulation comprises between about 5 mg/mL and about 40 mg/mL epinephrine, or a salt thereof. Alternative Embodiment 22. The nasal spray formulation as recited in any of Embodiments 1-21, wherein the formulation comprises between about 3 mg/mL and about 40 mg/mL epinephrine, or a salt thereof.

Embodiment 23. The nasal spray formulation as recited in any of Embodiments 1-22, wherein the formulation comprises between about 0.9 mg and about 2.4 mg per dose dispensed from the device of epinephrine, or a salt thereof.

Embodiment 24. The nasal spray formulation as recited in any of Embodiments 1-22, wherein the formulation comprises between about 0.5 mg and about 2.0 mg per dose dispensed from the device of epinephrine, or a salt thereof.

Embodiment 25. The nasal spray formulation as recited in any of Embodiments 1-22, wherein, the formulation comprises between about 0.75 mg and about 1.5 mg per dose dispensed from the device of epinephrine, or a salt thereof.

Embodiment 26. The nasal spray formulation as recited in any of Embodiments 1-22, wherein the formulation comprises between about 0.9 mg and about 1.15 mg per dose dispensed from the device of epinephrine, or a salt thereof.

Embodiment 27. The nasal spray formulation as recited in any of Embodiments 1-22, wherein the formulation comprises about 1.0 mg per dose dispensed from the device of epinephrine, or a salt thereof.

Embodiment 28. The nasal spray formulation as recited in any of Embodiments 1-22, wherein the formulation comprises between about 0.45 mg and about 1.15 mg per dose dispensed from the device of epinephrine, or a salt thereof.

Embodiment 29. The nasal spray formulation as recited in any of Embodiments 1-22, wherein the formulation comprises between about 1.0 mg and about 2.0 mg per dose dispensed from the device of epinephrine, or a salt thereof.

Embodiment 30. The nasal spray formulation as recited in any of Embodiments 1-29, wherein the formulation additionally comprises a stabilizing agent.

Embodiment 31. The nasal spray formulation as recited in Embodiment 30, wherein the stabilizing agent is ethylenediaminetetraacetic acid (EDTA) or a salt thereof.

Embodiment 32. The nasal spray formulation as recited in Embodiment 31, wherein the EDTA is disodium EDTA.

Embodiment 33. The nasal spray formulation as recited in Embodiment 31 or 32, wherein the EDTA is present in an amount that is from 5% to 15% of the amount of the epinephrine, both measured in mmol. Alternative Embodiment 33. The nasal spray formulation as recited in Embodiment 31 or 32, wherein the EDTA is present in an amount that is from 0.0010% (w/v) to 1% (w/v).

Embodiment 34. The nasal spray formulation as recited in Embodiment 31 or 32, wherein the mmol of EDTA is about 10% of the mmol of the epinephrine.

Embodiment 35. The nasal spray formulation as recited in any of Embodiments 1-34, wherein the formulation additionally comprises a preservative.

Embodiment 36. The nasal spray formulation as recited in Embodiment 35, wherein the preservative is benzalkonium chloride.

Embodiment 37. The nasal spray formulation as recited in any of Embodiments 1-34, wherein the formulation additionally comprises an absorption enhancer.

Embodiment 38. The nasal spray formulation as recited in Embodiment 37, wherein the absorption enhancer is an alkylsaccharide.

Embodiment 39. The nasal spray formulation as recited in Embodiment 38, wherein the absorption enhancer is dodecyl maltoside.

Embodiment 40. The nasal spray formulation as recited in Embodiment 39, wherein the formulation comprises about 0.005% (w/v) to about 2.5% (w/v) dodecyl maltoside.

Embodiment 41. The nasal spray formulation as recited in Embodiment 40, wherein the formulation comprises about 0.1% (w/v) to about 0.5% (w/v) dodecyl maltoside.

Embodiment 42. The nasal spray formulation as recited in Embodiment 41, wherein the formulation comprises about 0.25% (w/v) dodecyl maltoside. Alternative Embodiment 42. The nasal spray formulation as recited in Embodiment 41, wherein the formulation comprises about 0.25% (w/v) dodecyl maltoside and about 0.001 (w/v) to about 1% (w/v) benzalkonium chloride. Alternative Embodiment 42. The nasal spray formulation as recited in Embodiment 41, wherein the formulation comprises about 0.25% (w/v) dodecyl maltoside and about 0.001 (w/v) to about 1% (w/v) Oleic acid, or salt thereof. Alternative Embodiment 42. The nasal spray formulation as recited in Embodiment 41, wherein the formulation comprises about 0.25% (w/v) dodecyl maltoside, about 0.001 to about 1% (w/v) benzalkonium chloride and about 0.001 to about 1% (w/v) oleic acid, or salt thereof.

Embodiment 43a. In certain embodiments, the formulation comprises between about 0.75 mg and about 1.5 mg per dose dispensed from the device of epinephrine, or a salt thereof, and when administered as a nasal spray to a subject yields one or more of the following pharmacokinetic features:
both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields;
a mean $C_{max}$ that is at least 80% of the Cmax and no more than 150% of the Cmax that a 0.3 mg intramuscular injection yields;
a mean tmax of less than 45 minutes; and
IM-injection like absorption under optimal dosing conditions in the thigh.

Embodiment 43b. In certain embodiments, the formulation comprises between about 0.5 mg and about 1.15 mg per dose dispensed from the device of epinephrine, or a salt thereof, and when administered as a nasal spray to a subject yields one or more of the following pharmacokinetic features:

Both the mean $AUC_{0\text{-}20\ min}$ and $AUC_{0\text{-}t}$ is at least 80% of the $AUC_{0\text{-}20\ min}$ and $AUC_{0\text{-}t}$ that a 0.15 mg intramuscular injection yields;
A mean $C_{max}$ that is at least 80% of the Cmax and no more than 150% of the Cmax that a 0.15 mg intramuscular injection yields;
A mean tmax of less than 45 minutes
IM-injection like absorption under optimal dosing conditions in the thigh.

Embodiment 43c. In certain embodiments, the formulation comprises between about 1.0 mg and about 2.0 mg per dose dispensed from the device of epinephrine, or a salt thereof, and when administered as a nasal spray to a subject yields one or more of the following pharmacokinetic features:
both the mean $AUC_{0\text{-}20\ min}$ and $AUC_{0\text{-}t}$ are at least 80% of the $AUC_{0\text{-}20\ min}$ and $AUC_{0\text{-}t}$ that a 0.5 mg intramuscular injection yields;
a mean $C_{max}$ that is at least 80% of the Cmax and no more than 150% of the Cmax that a 0.5 mg intramuscular injection yields;
a mean tmax of less than 45 minutes; and
IM-injection like absorption under optimal dosing conditions in the thigh.

Also provided are embodiments wherein any of Embodiments 43a, 43b, and 43c comprise one or more of the limitations recited above in Embodiments 2-22 and 30-42.

Also provided herein is Embodiment 44, a nasal spray formulation comprising epinephrine, or a salt thereof, which when administered to a subject, yields one or more of the following pharmacokinetic features:
both the mean $AUC_{0\text{-}20\ min}$ and $AUC_{0\text{-}t}$ are at least 80% of the $AUC_{0\text{-}20\ min}$ and $AUC_{0\text{-}t}$ that a 0.3 mg intramuscular injection yields;
a mean $C_{max}$ that is at least 80% of the $C_{max}$ and no more than 150% of the Cmax that a 0.3 mg intramuscular injection yields;
a mean $t_{max}$ of less than 45 minutes; and
IM-injection like absorption under optimal dosing conditions in the thigh.

Also provided herein is Embodiment 45, a nasal spray formulation comprising epinephrine, or a salt thereof, which when administered to a subject, yields one or more of the following pharmacokinetic features:
both the mean $AUC_{0\text{-}20\ min}$ and $AUC_{0\text{-}t}$ are at least 80% of the $AUC_{0\text{-}20\ min}$ and $AUC_{0\text{-}t}$ that a 0.15 mg intramuscular injection yields;
a mean $C_{max}$ that is at least 80% of the $C_{max}$ and no more than 150% of the $C_{max}$ that a 0.15 mg intramuscular injection yields;
a mean $t_{max}$ of less than 45 minutes; and
IM-injection like absorption under optimal dosing conditions in the thigh, Also provided herein is Embodiment 46, a nasal spray formulation comprising epinephrine, or a salt thereof, which when administered to a subject, yields one or more of the following pharmacokinetic features:
both the mean $AUC_{0\text{-}20\ min}$ and $AUC_{0\text{-}t}$ are at least 80% of the $AUC_{0\text{-}20\ min}$ and $AUC_{0\text{-}t}$ that a 0.5 mg intramuscular injection yields;
a mean $C_{max}$ that is at least 80% of the $C_{max}$ and no more than 150% of the Cmax that a 0.5 mg intramuscular injection yields;
a mean $t_{max}$ of less than 45 minutes; and
IM-injection like absorption under optimal dosing conditions in the thigh.

Embodiment 47. The nasal spray formulation as recited in any of Embodiments 45-46, comprising between about 0.4 mg and about 2.40 mg per dose dispensed from the device of epinephrine, or a salt thereof.

Embodiment 48. The nasal spray formulation as recited in Embodiment 47, wherein the formulation is a pharmaceutical formulation.

Embodiment 49. The nasal spray formulation as recited in Embodiment 48, wherein the epinephrine or salt thereof is present in the pharmaceutical formulation in an amount efficacious for the treatment of an acute hypersensitivity reaction.

Embodiment 50. The nasal spray formulation as recited in any of Embodiments 44-49, wherein the formulation is aqueous.

Embodiment 51. The nasal spray formulation as recited in any of Embodiments 44-50, wherein the formulation has intramuscular (IM)-injection-like or subcutaneous (SQ)-like absorption.

Embodiment 52. The nasal spray formulation as recited in Embodiment 51, wherein the formulation has intramuscular (IM)-injection-like absorption.

Embodiment 53. The nasal spray formulation as recited in Embodiment 51, wherein the formulation has subcutaneous (SQ)-like absorption.

Embodiment 54. The nasal spray formulation as recited in Embodiment 1-51 where the SC pharmacokinetic profile has a $C_{max}$ of at least 100 pg/mL and $AUC_{0-240\ min}$ of 150 h*pg/mL.

Embodiment 55. The nasal spray formulation as recited in any of Embodiments 44-54, wherein the formulation comprises between about 5 mg/mL and about 40 mg/mL of epinephrine, or a salt thereof.

Embodiment 56. The nasal spray formulation as recited in any of Embodiments 44-55, wherein the formulation comprises between about 0.9 mg and about 2.4 mg per dose dispensed from the device of epinephrine, or a salt thereof.

Embodiment 57. The nasal spray formulation as recited in any of Embodiments 44-55, wherein the formulation comprises between about 0.5 mg and about 2.0 mg per dose dispensed from the device of epinephrine, or a salt thereof.

Embodiment 58. The nasal spray formulation as recited in any of Embodiments 44-55, wherein, the formulation comprises between about 0.75 mg and about 1.5 mg per dose dispensed from the device of epinephrine, or a salt thereof.

Embodiment 59. The nasal spray formulation as recited in any of Embodiments 44-55, wherein the formulation comprises between about 0.9 mg and about 1.15 mg per dose dispensed from the device of epinephrine, or a salt thereof.

Embodiment 60. The nasal spray formulation as recited in any of Embodiments 44-55, wherein the formulation comprises about 1.0 mg per dose dispensed from the device of epinephrine, or a salt thereof.

Embodiment 61. The nasal spray formulation as recited in any of Embodiments 44-55, wherein the formulation comprises between about 0.45 mg and about 1.15 mg per dose dispensed from the device of epinephrine, or a salt thereof.

Embodiment 62. The nasal spray formulation as recited in any of Embodiments 44-55, wherein the formulation comprises between about 0.5 mg and about 2.0 mg per dose dispensed from the device of epinephrine, or a salt thereof.

Embodiment 63. The nasal spray formulation as recited in any of Embodiments 44-55, wherein the formulation comprises about 0.5 mg per dose dispensed from the device of epinephrine, or a salt thereof.

Embodiment 64. The nasal spray formulation as recited in any of Embodiments 44-55, wherein the formulation comprises about 0.75 mg per dose dispensed from the device of epinephrine, or a salt thereof.

Embodiment 65. The nasal spray formulation as recited in any of Embodiments 44-55, wherein the formulation comprises about 1.0 mg per dose dispensed from the device of epinephrine, or a salt thereof.

Embodiment 66. The nasal spray formulation as recited in any of Embodiments 44-55, wherein the formulation comprises about 1.5 mg per dose dispensed from the device of epinephrine, or a salt thereof.

Embodiment 67. The nasal spray formulation as recited in any of Embodiments 44-66, wherein the formulation comprises less than one molar equivalents of acid to each mole of epinephrine.

Embodiment 68. The nasal spray formulation as recited in any of Embodiments 44-66, wherein the formulation comprises between about 0.5 and about 1.1 molar equivalents of acid to each mole of epinephrine.

Embodiment 69. The nasal spray formulation as recited in either of Embodiments 66 and 67, wherein the acid is a strong acid. Strong acids include hydrochloric acid, phosphoric acid, and sulfuric acid.

Embodiment 70. The nasal spray formulation as recited in Embodiment 69, wherein the acid is hydrochloric acid.

Embodiment 71. The nasal spray formulation as recited in any of Embodiments 44-70, wherein no base is added to the formulation during its preparation.

Embodiment 72. The nasal spray formulation as recited in any of Embodiments 44-71, wherein the formulation has a pH between about 3.0 and about 6.0. Alternative embodiment Embodiment 72. The nasal spray formulation as recited in any of Embodiments 44-71, wherein the formulation has a pH between about 2.0 and about 6.0.

Embodiment 73. The nasal spray formulation as recited in Embodiment 72, wherein the formulation has a pH between about 3.5 and about 5.0.

Embodiment 74. The nasal spray formulation as recited in Embodiment 72, wherein the formulation has a pH between about 4.0 and about 4.5.

Embodiment 75. The nasal spray formulation as recited in Embodiment 72, wherein the formulation has a pH of about 4.5.

Embodiment 76. The nasal spray formulation as recited in Embodiment 72, wherein the formulation has a pH of about 4.0.

Embodiment 77. The nasal spray formulation as recited in any of Embodiments 44-76, wherein the formulation additionally comprises a stabilizing agent.

Embodiment 78. The nasal spray formulation as recited in Embodiment 77, wherein the stabilizing agent is ethylenediaminetetraacetic acid (EDTA) or a salt thereof.

Embodiment 79. The nasal spray formulation as recited in Embodiment 78, wherein the EDTA is disodium EDTA.

Embodiment 80. The nasal spray formulation as recited in Embodiment 78, wherein the EDTA is present in an amount that is from 5% to 15% of the amount of the epinephrine, both measured in mmol. Alternative Embodiment 80. The nasal spray formulation as recited in Embodiment 78, wherein the EDTA is present in an amount that is from about 0.001% (w/v) to about 1% (w/v).

Embodiment 81. The nasal spray formulation as recited in Embodiment 79, wherein the mmol of EDTA is about 10% of the mmol of the epinephrine.

Embodiment 82. The nasal spray formulation as recited in any of Embodiments 44-81, wherein the formulation additionally comprises a preservative.

Embodiment 83. The nasal spray formulation as recited in Embodiment 82, wherein the preservative is benzalkonium chloride.

Embodiment 84. The nasal spray formulation as recited in any of Embodiments 44-83, wherein the formulation additionally comprises an absorption enhancer. In alternative Embodiment 84, The nasal spray formulation as recited in any of Embodiments 44-83, wherein the formulation additionally comprises one or more absorption enhancers.

Embodiment 85. The nasal spray formulation as recited in Embodiment 84, wherein the absorption enhancer is an alkylsaccharide. In alternative Embodiment 85, The nasal spray formulation as recited in Embodiment 84, wherein the absorption enhancer is an alkylsaccharide and/or benzalkonium chloride.

Embodiment 86. The nasal spray formulation as recited in Embodiment 85, wherein the absorption enhancer is dodecyl maltoside. In alternative Embodiment 86, The nasal spray formulation as recited in Embodiment 85, wherein the absorption enhancer is dodecyl maltoside, benzalkonium chloride, or a combination of dodecyl maltoside and benzylalkonium chloride.

Embodiment 87. The nasal spray formulation as recited in Embodiment 86, wherein the formulation comprises about 0.005% (w/v) to about 2.5% (w/v) dodecyl maltoside.

Embodiment 88. The nasal spray formulation as recited in Embodiment 87, wherein the formulation comprises about 0.1% (w/v) to about 0.5% (w/v) dodecyl maltoside.

Embodiment 89. The nasal spray formulation as recited in Embodiment 88, wherein the formulation comprises about 0.25% (w/v) dodecyl maltoside. Also provided is Embodiment 90, a method of treatment of a condition mediated by adrenergic receptors comprising the intranasal administration of the formulation as recited in any of Embodiments 1-89 above.

Embodiment 91. The method as recited in Embodiment 90, wherein the condition is chosen from a type-1 hypersensitivity reaction (systemic allergic reaction), an acute asthmatic attack, cardiac arrest, and Stokes-Adams Syndrome.

Embodiment 92. The method as recited in Embodiment 91, wherein the condition is a type-1 hypersensitivity reaction (systemic allergic reaction).

Embodiment 93. The method as recited in Embodiment 92, wherein the type-1 hypersensitivity reaction (systemic allergic reaction) is chosen from allergic asthma, allergic conjunctivitis, allergic rhinitis, anaphylaxis, angioedema, urticaria, eosinophilia, drug allergy and food allergy.

Embodiment 94. The method as recited in Embodiment 93, wherein the drug allergy is an antibiotic allergy.

Embodiment 95. Also provided herein is a method of treatment of a systemic allergic reaction and anaphylaxis comprising the intranasal administration of an unbuffered intranasal formulation of epinephrine in an amount less than about 2.0 mg.

Also provided are embodiments wherein Embodiment 95 comprises one or more of the limitations recited above in Embodiments 2-22, 25-28, 30-55, 58-61, and 63-89.

Embodiment 96. A pharmaceutical composition comprising: a) epinephrine; and b) an alkylglycoside; wherein the composition is formulated for administration into the circulatory system of a subject via the intranasal, inhalation, or pulmonary administration route. Alternative Embodiment 96. A pharmaceutical composition comprising: a) epinephrine; and b) an alkylglycoside; wherein the composition is a liquid formulated for intranasal delivery.

Embodiment 97. The pharmaceutical composition of Embodiment 96, wherein the alkylglycoside has an alkyl chain including between 8 to 20 carbons.

Embodiment 98. The pharmaceutical composition of Embodiment 97, wherein the alkylglycoside is selected from the group consisting of undecyl maltoside, dodecyl maltoside, tridecyl maltoside, tetradecyl maltoside, sucrose mono-dodecanoate, sucrose mono-tridecanoate, and sucrose mono-tetradecanoate.

Embodiment 99. The pharmaceutical composition of Embodiment 98, wherein the alkylglycoside is dodecyl-beta-D-maltoside.

Embodiment 100. The pharmaceutical composition of Embodiment 96, wherein the alkylglycoside concentration is between about 0.001% and 10.0% (w/v).

Embodiment 101. The pharmaceutical composition of Embodiment 100, wherein the alkylglycoside concentration is between about 0.05% and 0.5% (w/v).

Embodiment 102. The pharmaceutical composition of Embodiment 96, wherein the composition further comprises a membrane penetration-enhancing agent. The pharmaceutical composition of Embodiment 96, wherein the composition further comprises a membrane penetration-enhancing agent, pH modifier, buffering agents, isotonicity agent, antioxidant, chelator, preservative, or a combination thereof.

Embodiment 103. The pharmaceutical composition of Embodiment 102, wherein the membrane penetration-enhancing agent is a surfactant, a bile salt, a phospholipid, an alcohol, an enamine, a medium and/or long-chain amphipathic molecule, a small hydrophobic molecule, sodium or a salicylic acid derivative, a glycerol ester of acetoacetic acid, a cyclodextrin, a medium-chain or long chain fatty acid, a chelating agent, an amino acid or salt thereof, an enzyme or combination thereof.

Embodiment 104. The pharmaceutical composition of Embodiment 102, wherein the membrane penetration-enhancing agent is selected from the group consisting of citric acid, sodium citrate, propylene glycol, glycerin, ascorbic acid, sodium metabisulfite, ethylenediaminetetraacetic acid (EDTA) disodium, benzalkonium chloride, sodium hydroxide, and combinations thereof.

Embodiment 105. The pharmaceutical composition of Embodiment 102, wherein the membrane penetration-enhancing agent is benzalkonium chloride, EDTA, or a combination thereof.

Embodiment 106. The pharmaceutical composition of Embodiment 96, wherein the composition provides a Cmax for the epinephrine in a subject that is about 2 fold or greater as compared to administration without alkylglycoside.

Embodiment 107. The pharmaceutical composition of Embodiment 96, wherein the composition provides a Tmax for the epinephrine in a subject that is about 2 fold or less as compared to administration without alkylglycoside.

Embodiment 108. The pharmaceutical composition of Embodiment 96, wherein the composition provides a Tmax for the epinephrine of about 0.3 hours or less in a subject.

Embodiment 109. The pharmaceutical composition of Embodiment 96, wherein the composition has a pH of about 2.0 to 5.0.

Embodiment 110. A method of increasing the bioavailability of epinephrine in a subject comprising administering to a subject a composition comprising epinephrine and an alkylglycoside, thereby increasing the bioavailability of the epinephrine in the subject, wherein the composition is administered into the circulatory system of the subject via the intranasal, inhalation, or pulmonary administration route. Alternative Embodiment 110. A method of increasing the bioavailability of epinephrine in a subject comprising administering to a subject a composition comprising epinephrine and an alkylglycoside, thereby increasing the bioavailability of the epinephrine in the subject, wherein the composition is a liquid composition administered intranasally.

Embodiment 111. The method of Embodiment 110, wherein the alkylglycoside has an alkyl chain including between 8 to 20 carbons.

Embodiment 112. The method of Embodiment 111, wherein the alkylglycoside is selected from the group consisting of undecyl maltoside, dodecyl maltoside, tridecyl maltoside, tetradecyl maltoside, sucrose mono-dodecanoate, sucrose mono-tridecanoate, and sucrose mono-tetradecanoate.

Embodiment 113. The method of Embodiment 112, wherein the alkylglycoside is dodecyl-beta-D-maltoside.

Embodiment 114. The method of Embodiment 110, wherein the alkylglycoside concentration is between about 0.001% and 10.0% (w/v).

Embodiment 115. The method of Embodiment 114, wherein the alkylglycoside concentration is between about 0.05% and 0.5% (w/v).

Embodiment 116. The method of Embodiment 110, wherein the composition further comprises a membrane penetration-enhancing agent.

Embodiment 117. The method of Embodiment 116, wherein the membrane penetration-enhancing agent is a surfactant, a bile salt, a phospholipid, an alcohol, an enamine, a long-chain amphipathic molecule, a small hydrophobic molecule, sodium or a salicylic acid derivative, a glycerol ester of acetoacetic acid, a cyclodextrin, a medium-chain fatty acid, a chelating agent, an amino acid or salt thereof, an enzyme or combination thereof.

Embodiment 118. The method of Embodiment 117, wherein the membrane penetration-enhancing agent is selected from the group consisting of citric acid, sodium citrate, propylene glycol, glycerin, ascorbic acid, sodium metabisulfite, ethylenediaminetetraacetic acid (EDTA) disodium, benzalkonium chloride, sodium hydroxide, and combinations thereof.

Embodiment 119. The method of Embodiment 116, wherein the membrane penetration-enhancing agent is benzalkonium chloride, EDTA, or a combination thereof.

Embodiment 120. The method of Embodiment 110, wherein the composition provides a Cmax for the epinephrine in the subject that is about 2 fold or greater as compared to administration without alkylglycoside.

Embodiment 121. The method of Embodiment 110, wherein the composition provides a Tmax for the epinephrine in the subject that is about 2 fold or less as compared to administration without alkylglycoside.

Embodiment 122. The method of Embodiment 110, wherein the composition provides a Tmax for the epinephrine of about 0.3 hours or less in the subject.

Embodiment 123. The method of Embodiment 110, wherein the composition has a pH of about 2.0 to 6.0. Alternative Embodiment 123. The method of Embodiment 110, wherein the composition has a pH of about 2.0 to 5.0.

Definitions

As used herein, the following terms have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range of numbers between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a range. When no range, such as a margin of error or a standard deviation to a mean value given in a chart or table of data, is recited, the term "about" should be understood to mean the greater of the range which would encompass the recited value and the range which would be included by rounding up or down to that figure as well, considering significant figures, and the range which would encompass the recited value plus or minus 20%.

"Weight per volume" or "w/v" refers to the mass in grams of a dissolved solute divided by the volume in milliliters of the entire solution. Typically, weight by volume is expressed as a percentage.

The term "absorption enhancer," as used herein, refers to a functional excipient included in formulations to improve the absorption of an active agent such as a pharmacologically active drug. This term usually refers to an agent whose function is to increase absorption by enhancing nasal mucous-membrane permeation, rather than increasing solubility. As such, such agents are sometimes called permeation enhancers or penetration enhancers. In particular, absorption enhancers described herein may improve paracellular transport (i.e., passage through intercellular spaces and tight junctions), transcellular transport (i.e., passive diffusion or active transport across cellular membranes), or transcytosis (i.e., cellular vesicular uptake). Ozsoy et al., Molecules 14:3754-79, 2009.

Examples of absorption enhancers include alcohol, aprotinin, benzalkonium chloride, benzyl alcohol, capric acid, ceramides, cetylpyridinium chloride, chitosan, cyclodextrins, deoxycholic acid, decanoyl, dimethyl sulfoxide, glyceryl monooleate, glycofurol, glycofurol, glycosylated sphingosines, glycyrrhetinic acids, 2-hydroxypropyl-β-cyclodextrin, laureth-9, lauric acid, lauroyl camitine, sodium lauryl sulfate, lysophosphatidylcholine, menthol, poloxamer 407 or F68, poly-L-arginine, polyoxyethylene-9-lauryl ether, isopropyl myristate, isopropyl palmitate, lanolin, light mineral oil, linoleic acid, menthol, myristic acid, myristyl alcohol, oleic acid, or salt thereof, oleyl alcohol, palmitic acid, polysorbate 80, propylene glycol, polyoxyethylene alkyl ethers, polyoxylglycerides, pyrrolidone, quillaia saponin, salicylic acid, sodium salt, β-sitosterol β-D-glucoside, sucrose cocoate, taurocholic acid, taurodeoxycholic acid, taurodihydrofusidic acid, thymol, tricaprylin, triolein, and alkylsaccharides, and combinations thereof, including but not limited to dodecyl maltoside, dodecyl-β-D-maltoside, tetradecyl maltoside, tetradecyl-β-D-maltoside and sucrose dodecanoate. Alkylsaccharides (e.g., nonionic alkylsaccharide surfactants such as alkylglycosides and sucrose esters of fatty acids that consist of an aliphatic hydrocarbon chain coupled to a sugar moiety by a glycosidic or ester bond, respectively), cyclodextrins (cyclic oligosaccharides composed of six or more monosaccharide units with a central cavity, which form inclusion complexes with hydrophobic molecules and they have primarily been used to increase drug solubility and dissolution and to enhance low molecular weight drug absorption), chitosans (linear cationic polysaccharides produced from the deacetylation of chitin), and bile salts and their derivatives (such as sodium glycocholate, sodium taurocholate, and sodium taurodihydrofusidate) tend to be amongst the best-tolerated absorption enhancers. See, e.g., Aungst B J, *AAPS Journal* 14(1):10-8, 2011; and Maggio, ET, *Excipients and Food Chem.* 5(2): 100-12, 2014. Due to their chemical properties, certain absorption enhancers can function as preservatives and/or cationic surfactants in certain circumstances, depending on concentration in the formulation and other factors.

Described herein are compositions comprising epinephrine and at least one absorption enhancer and/or preservative and/or surfactant wherein the at least one absorption enhancer and/or preservative and/or surfactant comprises at least one alkylglycoside and/or at least one saccharide alkyl ester.

As used herein, the term "alkylsaccharide" (also referred to herein as "alkylglycoside") refers to a type of an absorption enhancer. As used herein, an alkylsaccharide refers to any sugar joined by a linkage to any hydrophobic alkyl, as is known in the art. Alkylsaccharides include, but are not limited to: alkylsaccharides, such as octyl-, nonyl-, decyl-, undecyl-, dodecyl-, tridecyl-tetradecyl-, pentadecyl-, hexadecyl-, heptadecyl-, and octadecyl-α- or β-D-maltoside, -glucoside or -sucroside; alkyl thiomaltosides, such as heptyl, octyl, dodecyl-, tridecyl-, and tetradecyl-β-D-thiomaltoside; alkyl thioglucosides, such as heptyl- or octyl 1-thio α- or β-D-glucopyranoside; alkyl thiosucroses; alkyl maltotriosides; long chain aliphatic carbonic acid amides of sucrose β-amino-alkyl ethers; derivatives of palatinose and isomaltamine linked by amide linkage to an alkyl chain; derivatives of isomaltamine linked by urea to an alkyl chain; long chain aliphatic carbonic acid ureides of sucrose p-amino-alkyl ethers; and long chain aliphatic carbonic acid amides of sucrose p-amino-alkyl ethers. The hydrophobic alkyl can be chosen of any desired size, depending on the hydrophobicity desired and the hydrophilicity of the saccharide moiety. For example, one preferred range of alkyl chains is from about 9 to about 24 carbon atoms. An even more preferred range is from about 9 to about 16 or about 14 carbon atoms. Similarly, some preferred saccharides include maltose, sucrose, and glucose linked by glycosidic linkage to an alkyl chain of 9, 10, 12, 13, 14, 16, 18, 20, 22, or 24 carbon atoms, e.g., nonyl-, decyl-, dodecyl- and tetradecyl sucroside, glucoside, and maltoside, etc. The alkyl chain of an alkylsaccharide is often linked to the saccharide via a glycosidic bond, and accordingly, alkylsaccharides are often interchangeably referred to as alkylglycosides.

Any "suitable" alkylglycoside means one that fulfills the characteristics contemplated herein, i.e., that the alkylglycoside be nontoxic and nonionic, and that it increases the absorption of a compound (e.g. epinephrine) when it is administered with the compound via the nasal delivery route.

As use herein, a "saccharide" is inclusive of monosaccharides, oligosaccharides or polysaccharides in straight chain or ring forms, or a combination thereof to form a saccharide chain. Oligosaccharides are saccharides having two or more monosaccharide residues. The saccharide can be chosen, for example, from any currently commercially available saccharide species or can be synthesized. Some examples of the many possible saccharides to use include glucose, maltose, maltotriose, maltotetraose, sucrose and trehalose. Preferable saccharides include maltose, sucrose and glucose.

In some embodiments, described herein are composition that include at least one alkylglycoside and/or saccharide alkyl ester and epinephrine, methods of administering and using the compositions via the nasal delivery route, and methods of ameliorating a disease state in a subject by administration of such compositions.

In some embodiments, described herein is a method of administering a composition having at least one alkylglycoside and/or saccharide alkyl ester admixed, mixed, or blended with epinephrine and administered or delivered to a subject, wherein the alkyl has from about 10 to 24, 10 to 20, 10 to 16, or 10 to 14 carbon atoms, wherein the at least one alkylglycoside and/or saccharide alkyl ester increases the stability and bioavailability of the therapeutic agent.

In some embodiments, alkylsaccharides contemplated have a hydrophobic alkyl group linked to a hydrophilic saccharide. The linkage between the hydrophobic alkyl group and the hydrophilic saccharide can include, among other possibilities, a glycosidic, thioglycosidic (Horton), amide (Carbohydrates as Organic Raw Materials, F. W. Lichtenthaler ed., VCH Publishers, New York, 1991), ureide (Austrian Pat. 386,414 (1988); Chem. Abstr. 110:137536p (1989); see Gruber, H. and Greber, G., "Reactive Sucrose Derivatives" in Carbohydrates as Organic Raw Materials, pp. 95-116) or ester linkage (Sugar Esters: Preparation and Application, J. C. Colbert ed., (Noyes Data Corp., New Jersey), (1974)). Further, preferred glycosides can include maltose, sucrose, and glucose linked by glycosidic linkage to an alkyl chain of about 9-16 carbon atoms, e.g., nonyl-, decyl-, dodecyl- and tetradecyl sucroside, glucoside, and maltoside. These compositions are amphipathic and non-toxic, because they degrade to an alcohol and an oligosaccharide.

The above examples are illustrative of the types of glycosides contemplated, but the list is not exhaustive. Derivatives of the above compounds which fit the criteria described herein are also contemplated when choosing an alkylsaccharide.

In some embodiments, membrane penetration-enhancing agents contemplated serve as anti-bacterial agents. An agent is an "anti-bacterial" agent or substance if the agent or its equivalent destroy bacteria, or suppress bacterial growth or reproduction.

The term "active ingredient" or "pharmaceutically active compound" is defined in the context of a "formulation" and is intended to mean a component of a pharmaceutical formulation that provides the primary pharmacological effect, as opposed to an "inactive ingredient" which would generally be recognized as providing no pharmaceutical benefit.

The term "actuation," as used herein, refers to operation of the device such that the pharmaceutical formulation is delivered therefrom.

The term "antimicrobial preservative," as used herein, refers to a pharmaceutically acceptable excipient with antimicrobial properties which is added to a pharmaceutical formulation to maintain microbiological stability. Antimicrobial preservatives include, but are not limited to, antibacterial agents, antifungal agents, antioxidants, and preservatives.

The term "AUC," as used herein, refers to the area under the drug plasma concentration-time curve. The term "$AUC_{0-t}$," as used herein, refers to the area under the drug plasma concentration-time curve from t=0 to the last measured or measurable concentration. The term "$AUC_{0-\infty}$," or equivalently, "$AUC_{0-inf}$," as used herein, refers to the area under the drug plasma concentration-time curve extrapolated to infinity (o).

As used here, the term "benzalkonium chloride" ("BZK") refers to a member of the class of quaternary ammonium compounds having the following structure:

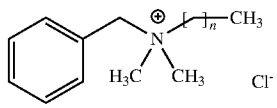

in which n is an integer. Benzalkonium chloride is a mixture of alkylbenzyl dimethylammonium chlorides, where a mixture of more than one n is used. In certain embodiments, n is 8, 10, 12, 14, 16, or 18. In other embodiments, n is 10, 12, or 14. In some embodiments, a mixture of n is 10, 12 and/or 14 predominate. In some embodiments, a mixture of n is 10, 12, 14 and/or 16 predominate. In some embodiments, benzalkonium chloride functions as a preservative (even in low amounts), an antiseptic, a disinfectant, a solubilizing and wetting agent, and/or a cationic surfactant. In some cases, benzalkonium chloride refers to a type of an absorption enhancer.

The term "bioavailability (F)," as used herein, refers to the fraction of a dose of drug that is absorbed from its site of administration and reaches, in an unchanged form, the systemic circulation. The term "absolute bioavailability" is used when the fraction of absorbed drug is related to its IV bioavailability. It may be calculated using the following formula:

$$F = \frac{AUC_{extravascular}}{AUC_{intravenous}} \times \frac{DOSE_{intravenous}}{DOSE_{extravascular}}$$

The term "relative bioavailability (Frei)" is used to compare two different extravascular routes of drug administration and it may be calculated using the following formula:

$$F_{rel} = \frac{AUC_{extravascular1}}{AUC_{extravascular2}} \times \frac{DOSE_{extravascular2}}{DOSE_{extravascular1}}$$

The term "clearance (CL)," as used herein, refers to the rate at which a drug is eliminated divided by its plasma concentration, giving a volume of plasma from which drug is completely removed per unit of time. CL is equal to the elimination rate constant ($\lambda$) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "$C_{max}$," as used herein, refers to the maximum observed plasma concentration.

The term "coefficient of variation (CV)," as used herein, refers to the ratio of the sample standard deviation to the sample mean. It is often expressed as a percentage.

The term "confidence interval," as used herein, refers to a range of values which will include the true average value of a parameter a specified percentage of the time.

The term "device," as used herein, refers to an apparatus capable of delivering a drug to patient in need thereof.

The term "delivery time," as used herein, refers to the amount of time that elapses between a determination made by a healthcare professional, or an untrained individual that an individual is in need of nasal delivery of epinephrine and completion of the delivery.

The term "disease," as used herein, is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the "dose dispensed from the device" is typically measured in the nasal spray setting by the difference in weight of a device before and after actuation to release a dose of the formulation contained therein. The volume of liquid formulation and weight in milligrams of the active moiety contained therein may be determined by standard calculations.

The term "elimination rate constant ($\lambda$)," as used herein, refers to the fractional rate of drug removal from the body. This rate is constant in first-order kinetics and is independent of drug concentration in the body. $\lambda$ is the slope of the plasma concentration-time line (on a logarithmic y scale). The term "$\lambda_z$," as used herein, refers to the terminal phase elimination rate constant, wherein the "terminal phase" of the drug plasma concentration-time curve is a straight line when plotted on a semi-logarithmic graph. The terminal phase is often called the "elimination phase" because the primary mechanism for decreasing drug concentration during the terminal phase is drug elimination from the body. The distinguishing characteristic of the terminal elimination phase is that the relative proportion of drug in the plasma and peripheral volumes of distribution remains constant. During this "terminal phase" drug returns from the rapid and slow distribution volumes to the plasma, and is permanently removed from the plasma by metabolism or renal excretion.

The term "equal," as used herein, means essentially the same as (i.e., negligibly different from) in quantity, amount, value, degree, or size. The term "equal" may, in certain embodiments, include "bioequivalent," but the terms are not coterminous.

The term "bioequivalent," as used herein, describes the relationship between a reference and a putative equivalent or alternative drug, and per 21 C.F.R. § 320.1, means that there is no significant difference in the rate and extent to which the active ingredient or active moiety in pharmaceutical equivalents or pharmaceutical alternatives becomes available at the site of drug action when administered at the same molar dose under similar conditions in an appropriately designed study. Rate and extent of absorption may be determined from, or informed by, $C_{max}$ and AUC, respectively. In certain embodiments, statistical criteria may be used, e.g., between 80% and 125% of a reference value, or 90% CI.

The term "molar equivalent," as used herein, refers to an amount of epinephrine that is equimolar to a specified amount of acid.

The term "excipient," as used herein, refers to a natural or synthetic substance formulated alongside the active ingredient of a medication. An excipient is included in a formulation for a variety of reasons such as, but not limited to, long-term stabilization, bulking up solid formulations, or to confer a therapeutic enhancement on the active ingredient in the final dosage form, such as facilitating drug absorption, reducing viscosity, or enhancing solubility.

The term "filled," as used herein, refers to an association between a device and a pharmaceutical formulation, for example, when a pharmaceutical formulation described herein comprising a therapeutically effective amount of epinephrine is present within a reservoir that forms a part of a device described herein.

The term "formulation," with or without the modifier "pharmaceutical," as used herein, refers to a composition comprising at least one physiologically active ingredient (e.g., a drug); including but not limited to, salts, solvates and hydrates of epinephrine and related compounds described herein, whereby the formulation is amenable to use for a specified, efficacious outcome in a mammal (for example, without limitation, a human).

The term "pharmaceutical formulation," as used herein, alone or in combination, refers to a formulation that is suited for use for treatment (or in certain embodiments, prevention) of a disease in a subject.

The term "hydrate," as used herein, refers to epinephrine described herein or a salt thereof that further includes a stoichiometric or non-stoichiometric amount of water bound by non-covalent intermolecular forces.

The term "in need of treatment" and the term "in need thereof" when referring to treatment are used interchangeably and refer to a judgment made by a caregiver (e.g. physician, nurse, nurse practitioner, that a patient will benefit from treatment.

As used herein, an "intramuscular (IM) injection" of epinephrine is typically administered via an IM epinephrine delivered by auto injector in the thigh, e.g., in the vestus lateralis muscle (referred to herein as "optimal dosing conditions in the thigh"). As such, when comparing pharmacokinetic parameters yielded by IM epinephrine injection to those yielded by IN epinephrine administration, the comparison should be assumed to be as if the IM injection were in the thigh, which is the optimal dosing method for epinephrine. In one embodiment, IM epinephrine injection is achieved with EpiPen® Auto-Injector (0.3 mg/0.3 mL epinephrine injection, USP, pre-filled auto-injector; Mylan Specialty L.P.).

As used herein, an "subcutaneous (SQ) injection" of epinephrine is typically administered by injection into the subcutaneous layer of the deltoid region in the upper arm. Simons et al. Epinephrine absorption in adults: Intramuscular versus subcutaneous injection. *J Allergy. Clin. Immunol.* 2001; 108:871-3.

As used herein, two embodiments are "mutually exclusive" when one is defined to be something which is different than the other. For example, an embodiment wherein the concentration of epinephrine is specified to be 5 mg/mL is mutually exclusive with an embodiment wherein the amount of epinephrine is specified to be 10 mg/mL. However, an embodiment wherein the amount of epinephrine is specified to be 5 mg/mL is not mutually exclusive with an embodiment in which less than about 10% of the pharmaceutical formulation leaves the nasal cavity via drainage into the nasopharynx or externally.

The term "pharmaceutically acceptable," as used herein, refers to a component of a formulation, often referred to as a carrier or excipient, that is compatible with the other ingredients of the formulation and not overly deleterious to the recipient thereof.

The term "pre-primed," as used herein, refers to a device, such as a nasal spray which can deliver a formulation to a patient in need thereof with the first actuation of the spray pump, i.e., without the need to prime the pump prior to dosing, such as by actuating the pump one or more times until a spray appears.

The term "prone," as used herein, refers to a patient who is lying face down.

As used herein, the term "protective packaging" refers to overwrap.

The term "solvate," as used herein, refers to epinephrine described herein or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "storage-stable," as used herein, refers to a formulation in which at least about 90% to 115% of the active ingredient remains within acceptable regulatory specifications after storage of the formulation at specified temperature and humidity for a specified time, for example, for at least 12 months at 25° C. and 60% relative humidity and about six months at about 40° C. and about 75% relative humidity.

The term "subject," as used herein, is intended to be synonymous with "patient," and refers to any mammal (preferably human) afflicted with a condition likely to benefit from treatment with a therapeutically effective amount epinephrine, e.g., a subject experiencing a type-1 hypersensitivity reaction (systemic allergic reaction) such as anaphylaxis.

The term "supine," as used herein, refers to a patient who is lying face up.

The term "nostril," as used herein, is synonymous with "naris."

The term "therapeutically effective amount" or "therapeutically effective dose," as used herein, refers to the amount or dose of active compound or pharmaceutical agent that elicits the biological or medicinal response in a tissue, system, or individual that is being sought by a researcher, healthcare provider or individual. A therapeutically effective amount may, but need not necessarily, eliminate one, more, or all symptoms of a disease, disorder, or condition being treated. A therapeutically effective amount may also prevent disease progression or the appearance of further symptoms.

The term "$t_{1/2}$" or "half-life," as used herein, refers to the amount of time required for half of a drug or other analyte of interest (for example, an adrenergic receptor agonist) to be eliminated from the body or the time required for a drug concentration to decline by half.

The term "tonicity agent," as used herein, refers to a compound which modifies the osmolality of a formulation, for example, to render it isotonic. Tonicity agents include, dextrose, lactose, sodium chloride, calcium chloride, magnesium chloride, sorbitol, sucrose, mannitol, trehalose, raffinose, polyethylene glycol, hydroxyethyl starch, glycine and the like. In some embodiments, formulations contemplated herein include one or more tonicity agents selected from dextrose, glycerin, mannitol, potassium chloride and sodium chloride. In some embodiments, formulations contemplated herein include sodium chloride as a tonicity agent.

The term "tomography," as used herein, refers to a process of imaging by sections. The images may be looked at individually, as a series of two-dimensional slices or together, as a computer-generated three-dimensional representation.

The term "$T_{max}$," as used herein, refers to the time, from administration, for a drug or other analyte to reach maximum drug plasma concentration ($C_{max}$).

Epinephrine

The term "epinephrine" as used herein refers to the compound (R)-4-(1-Hydroxy-2-(methylamino)ethyl)benzene-1,2-diol, also known as adrenaline, shown below and having the following structure, elemental makeup, molecular weight, and CAS Registry Number:

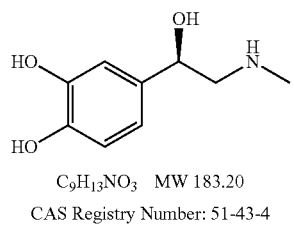

$C_9H_{13}NO_3$  MW 183.20

CAS Registry Number: 51-43-4

The term include any metabolite, salt, ester, hydrate, anhydride, solvate, isomer, isotope, enantiomer, free acid form, free base form, crystalline form, co-crystalline form, complexes, amorphous form, pro-drug (including ester pro-drug) form, racemate, polymorph, chelate, isomer, tautomer, or optically active form thereof, or mixture of any two or more of the foregoing.

Provided are drug products adapted for nasal delivery of epinephrine, including formulations and devices. Epinephrine acts by binding to a variety of adrenergic receptors. Epinephrine is a nonselective agonist of all adrenergic receptors, including the major subtypes $\alpha 1$, $\alpha 2$, $\beta 1$, $\beta 2$, and $\beta 3$. Its actions vary by tissue type and tissue expression of adrenergic receptors. For example, high levels of epinephrine causes smooth muscle relaxation in the airways but causes contraction of the smooth muscle that lines most arterioles.

Provided are formulations, devices adapted for nasal delivery of a formulation to a patient, kits comprising the foregoing, and methods of using the same in treatment, each comprising a therapeutically effective amount of epinephrine.

Epinephrine may be present in the formulations administered herein at concentrations between 1 mg/mL and 40 mg/mL, for example, at concentrations of about 5 mg/mL, about 10 mg/mL, or about 20 mg/mL.

Epinephrine may be present in the formulations administered herein at doses between 0.1 mg and 4 mg, for example, at doses of about 0.5 mg, about 1.0 mg, or about 2.0 mg. These doses may be scaled based on molecular weight of a counterion if a salt is used to prepare the formulation.

Epinephrine may optionally exist as a pharmaceutically acceptable salt including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., *Journal of Pharmaceutical Sciences*, 66:1-19 (1977). The acid addition salts may be obtained as the direct products of compound synthesis. In the alternative, the free base may be dissolved in a suitable solvent containing the appropriate acid and the salt isolated by evaporating the solvent or otherwise separating the salt and solvent. Due to the perceived insolubility of epinephrine base, finished dosage forms of epinephrine used in healthcare (solutions, aerosols, etc.) are typically salts, e.g. hydrochloride, bitartrate, or borate salts. In certain embodiments, formulations contemplated herein include a salt form of epinephrine that is epinephrine acetate, epinephrine hydrochloride, epinephrine tartrate, epinephrine bitartrate, epinephrine hydrogen tartrate or epinephrine borate.

Accordingly, provided herein are pharmaceutical formulations for intranasal administration comprising epinephrine. In certain embodiments, the formulation is an aqueous solution. In certain embodiments, the formulation comprises, per dose, between about 25 and about 250 μL of the aqueous solution. In certain embodiments, the formulation comprises, per dose, between about 50 and about 250 μL of the aqueous solution. In certain embodiments, the formulation comprises, per dose, between about 50 and about 200 μL of the aqueous solution. In certain embodiments, the formulation comprises, per dose, not more than about 140 μL. In certain embodiments, the formulation comprises, per dose, not more than about 100 μL. In certain embodiments, the formulation comprises, per dose, about 100 μL. The formulation may comprise, per dose, about 25 μL, about 50 μL, about 75 μL, about 100 μL, about 125 μL, about 150 μL, about 175 μL, about 200 μL, or about 250 μL of the aqueous solution.

The pharmaceutical formulations for intranasal administration comprising epinephrine described herein bypass potential metabolic conversion in the gastrointestinal tract and hepatic first-pass metabolism, and reach the systemic circulation in a pharmacologically active form. Epinephrine is extensively metabolized after oral administration by the catechol-O-methyltransferase in the gastrointestinal tract and by monoamine oxidase in the gastrointestinal tract and in the liver. Avoiding first pass clearance assures that more of the epinephrine that is administered will be available to treat anaphylaxis. By avoiding first pass liver clearance, the bioavailability of the epinephrine is increased.

Formulations

Also provided are pharmaceutical formulations comprising epinephrine. Certain embodiments of the present disclosure include a method of producing a formulation comprising admixing epinephrine and a pharmaceutically acceptable carrier. Pharmaceutical formulations are applied directly to the nasal cavity using the devices described herein. In the case of a spray, this may be achieved for example by means of a metering atomizing spray pump, e.g. a single, bi-dose or multiuse spray device, with or without a propellant.

Liquid preparations include solutions, suspensions and emulsions, for example, water, or water-ethanol, or water-propylene glycol solutions. Typically, the formulation is an aqueous liquid solution. Additional ingredients in liquid preparations may include preservatives, stabilizing agents, tonicity agents, absorption enhancers, pH-adjusting agents, antioxidants, buffers, sweetners/flavoring agents/task-masking agents, and optionally other ingredients. Ingredients in liquid preparations may serve different functions. The function(s) of a particular ingredient will depend on a number of factors including, but not limited to, presence or absence of other ingredients, concentration(s), and other factors.

Preservatives include: benzalkonium chloride, methylparaben, sodium benzoate, benzoic acid, phenyl ethyl alcohol, and the like, and mixtures thereof. Due to their chemical properties, certain preservatives can function as a surfactants and/or absorption enhancers in certain circumstances, depending on concentration in the formulation and other factors.

Other preservatives include: alcohol, benzalkonium chloride, benzethonium chloride, benzoic acid, benzyl alcohol, boric acid, bronopol, butylated hydroxyanisole (BHA), butylene glycol, butylparaben, calcium acetate, calcium chloride, calcium lactate, carbon dioxide, bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, magnesium trisilicate, isopropyl alcohol, lactic acid, methylparaben, monothioglycerol, parabens (methyl, ethyl and propyl), pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, propylparaben, propylparaben sodium, sodium acetate, sodium benzoate, sodium borate, sodium lactate, sodium metabisulfite, sodium propionate, sodium sulfite, sorbic acid, sulfobutyletherb-cyclodextrin, sulfur dioxide, edetic acid, thimerosal, and xylitol.

In some embodiments, preservatives include, but are not limited to, antibacterial agents, antifungal agents, and antioxidants.

Antibacterial agents include, but are not limited to, chlorocresol, diazolidinyl urea, dimethyl sulfoxide, glacial acetic acid, imidurea, iodine/edetic acid, phenylmercuric acetate, phenylmercuric borate, phenylmercuric hydroxide, potassium sorbate, sodium hydroxide, sorbic acid, thymol, antiseptics, and disinfectants.

Antifungal agents include, but are not limited to, benzoic acid, butylene glycol, butylparaben, chlorocresol, coconut oil, dimethyl sulfoxide, ethylparaben, glacial acetic acid, imidurea, methylparabens, phenylmercuric acetate, phenylmercuric borate, phenylmercuric hydroxide, potassium sorbate, propylparaben, sodium propionate, sodium thiosulfate, thymol, and vanillin.

Surfactants include but are not limited to: Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, and the like, and mixtures thereof. Due to their chemical properties, certain surfactants can function as a preservatives and/or absorption enhancers in certain circumstances, depending on concentration in the formulation and other factors.

Surfactants include but are not limited to: cationic, anionic, nonionic and zwitterionic surfactants.

Surfactants also include: anionic surfactants (e.g. carboxylates sulphonates, petroleum sulphonates, alkylbenzenesulphonates, naphthalene sulphonates, olefin sulphonates, alkyl sulphates, sulphates, sulphated natural oils and fats, sulphated esters, sulphated alkanolamides, alkylphenols, ethoxylated and sulphated), nonionic surfactants (e.g. ethoxylated aliphatic alcohol, polyoxyethylene surfactants, carboxylic esters, polyethylene glycol esters, anhydrosorbitol ester and it's ethoxylated derivatives, glycol esters of fatty acids, carboxylic amides, monoalkanolamine condensates, polyoxyethylene fatty acid amides), cationic surfactants (e.g. quaternary ammonium salts, amines with amide linkages, polyoxyethylene alkyl and alicyclic amines, 4.n,n,n',n' tetrakis substituted ethylenediamines, 2-alkyl 1-hydroxyethyl 2-imidazolines), amphoteric surfactants (amphoteric surfactants contains both an acidic and a basic hydrophilic moiety in their surface e.g., n-coco 3-aminopropionic acid/sodium salt, n-tallow 3-iminodipropionate, disodium salt, n-carboxymethyl n dimethyl n-9 octadecenyl ammonium hydroxide, n-cocoamidethyl n hydroxyethylglycine, sodium salt, etc.).

Antioxidants include, but are not limited to, tocopherol, arachidonic acid, ascorbic acid, ascorbyl palmitate, benzethonium chloride, benzethonium bromide, benzalkonium chloride, butylated hydroxyanisole (BHA), butylated hydroxytoluene (BHT), capric acid, caproic acid, carbon dioxide, cetylpyridium chloride, chelating agents, chitosan derivatives, citric acid monohydrate, dodecyl dimethyl aminopropionate, enanthic acid, erythorbic acid, ethyl oleate, fumaric acid, glycerol oleate, glyceryl monostearate, lauric acid, limonene, linolenic acid, lysine, malic acid, menthol, methionine, monothioglycerol, myristic acid, oleic acid, or salt thereof, palmitic acid, pelargonic acid, peppermint oil, phosphoric acid, polysorbates, potassium metabisulfite, propionic acid, propyl gallate, sodium ascorbate, sodium bisulfite, sodium caprate, sodium desoxycholate, sodium deoxyglycolate, sodium formaldehyde sulfoxylate, sodium glycocholate, sodium hydroxybenzoyal amino caprylate, sodium lauryl sulfate, sodium metabisulfite, sodium sulfite, sodium taurocholate, sodium thiosulfate, stearic acid, sulfur dioxide and a combination thereof.

Buffers include, but are not limited to, phosphate buffers, acetate buffers, and citrate buffers.

In some embodiments, the nasal spray formulation comprises a buffering agent. Buffering agents include, but are not limited to, adipic acid, boric acid, calcium carbonate, calcium hydroxide, calcium lactate, calcium phosphate, tribasic, citric acid monohydrate, dibasic sodium phosphate, diethanolamine, glycine, maleic acid, malic acid, methionine, monobasic sodium phosphate, monoethanolamine, monosodium glutamate, phosphoric acid, potassium citrate, sodium acetate, sodium bicarbonate, sodium borate, sodium carbonate, sodium citrate dihydrate, sodium hydroxide, sodium lactate, and triethanolamine.

Isotonicity agents include sodium chloride, calcium chloride, magnesium chloride, sorbitol, sucrose, dextrose, lactose, mannitol, trehalose, raffinose, polyethylene glycol, hydroxyethyl starch, glycerine, glycine, and the like, and mixtures thereof. In certain embodiments, the isotonicity agent is chosen from dextrose, glycerin, mannitol, potassium chloride, and sodium chloride. In certain embodiments, the isotonicity agent is sodium chloride. In certain embodiments, the formulations disclosed herein contain sodium chloride in an amount sufficient to cause the final composition to have a nasally acceptable osmolality, preferably 240-350 mOsm/kg. In certain embodiments, the formulations contain 0.3-1.9% sodium chloride.

Sweetners/flavoring agents/task-masking agents include, but are not limited to, sucrose, dextrose, lactose, sucralose, acesulfame-K, aspartame, saccharin, sodium saccharin, citric acid, aspartic acid, eucalyptol, mannitol, glycerin, xylitol, menthol, glycyrrhizic acid, cinnamon oils, oil of wintergreen, peppermint oils, clover oil, bay oil, anise oil, *eucalyptus*, vanilla, citrus oil such as lemon oil, orange oil, grape and grapefruit oil, fruit essences including apple, peach, pear, strawberry, raspberry, cherry, plum, pineapple, apricot, etc. and combinations thereof. In some embodiments, the formulations contain from about 0.0001 percent to about 1 percent of a sweetner/flavoring agent/task-masking agent, and may be present at lower or higher amounts as a factor of one or more of potency of the effect on flavor, solubility of the flavorant, effects of the flavorant on solubility or other physicochemical or pharmacokinetic properties of other formulation components, or other factors.

In certain embodiments, the pharmaceutical formulation additionally comprises an isotonicity agent. The intranasal formulation may comprise between about 0.2% (w/v) and about 1.2% (w/v) isotonicity agent, such as about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), or about 1.2% (w/v). The intranasal formulation may comprise more than about 0.1% (w/v) isotonicity agent. The intranasal formulation may comprise less than about 1.2% (w/v) isotonicity agent. In other embodiments, the intranasal formulation may comprise between about 0.2% (w/v) and about 1.9% (w/v) isotonicity agent, such as about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), or about 1.9% (w/v). The intranasal formulation may comprise less than about 1.9% (w/v) isotonicity agent.

In certain embodiments, the formulation additionally comprises an absorption enhancer. In certain embodiments, the pharmaceutical formulation comprises between about 0.005% (w/v) to about 2.5% (w/v) of the absorption enhancer. In certain embodiments, the pharmaceutical formulation comprises between about 0.05% (w/v) to about 2.5% (w/v) of the absorption enhancer. In certain embodiments, the pharmaceutical formulation comprises between about 0.1% (w/v) to about 0.5% (w/v) of the absorption enhancer. In certain embodiments, the pharmaceutical formulation comprises about 0.25% (w/v) of the absorption enhancer. In certain embodiments, the pharmaceutical formulation comprises about 0.18% (w/v) of the absorption enhancer.

In certain embodiments, the absorption enhancer is selected from benzalkonium chloride, cyclodextrins, chitosan, deoxycholic acid, an alkylsaccharide (e.g., a nonionic alkylsaccharide surfactant such as an alkylglycoside and a sucrose ester of fatty acids that consists of an aliphatic hydrocarbon chain coupled to a sugar moiety by a glycosidic or ester bond, respectively), fusidic acid derivatives, glycocholic acid, laureth-9, phosphatidylcholines, taurocholic acid, taurodihydrofusidic acid, microspheres and liposomes, and bile salts. In certain embodiments, the absorption enhancer is benzalkonium chloride. The formulation may comprise about 0.01% (w/v) to about 1% (w/v) benzalkonium chloride. In certain embodiments, the pharmaceutical formulation comprises about 0.005% (w/v) to about 0.015% (w/v) benzalkonium chloride. In certain embodiments, the pharmaceutical formulation comprises about 0.01% (w/v), about 0.02% (w/v), about 0.03% (w/v), or about 0.04% (w/v) of benzalkonium chloride. In certain embodiments, the pharmaceutical formulation comprises about 0.01% (w/v) benzalkonium chloride. In certain embodiments, the pharmaceutical formulation comprises about 0.02% (w/v) benzalkonium chloride. In certain embodiments, the pharmaceutical formulation comprises about 0.04% benzalkonium chloride.

In certain embodiments, the pharmaceutical formulation comprises benzalkonium chloride in an amount between about 0.001% (w/v) and about 1% (w/v). In certain other embodiments, the pharmaceutical formulation comprises benzalkonium chloride in an amount between about 0.001% (w/v) and about 0.5% (w/v). In certain other embodiments, the pharmaceutical formulation comprises benzalkonium chloride in an amount between about 0.001% (w/v) and about 0.2% (w/v). In some embodiments, the pharmaceutical formulation comprises 0.001% (w/v), 0.003% (w/v), 0.005% (w/v), 0.007% (w/v), 0.009% (w/v), 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.10% (w/v), 0.110% (w/v), 0.12% (w/v), 0.130% (w/v), 0.14% (w/v), 0.150% (w/v), 0.16% (w/v), 0.17% (w/v), 0.18% (w/v), 0.19% (w/v), 0.2% (w/v), 0.31% (w/v), 0.22% (w/v), 0.23% (w/v), 0.24% (w/v), 0.25% (w/v), 0.26% (w/v), 0.27% (w/v), 0.28% (w/v), 0.29% (w/v), 0.3% (w/v), 0.31% (w/v), 0.32% (w/v), 0.33% (w/v), 0.34% (w/v), 0.35% (w/v), 0.36% (w/v), 0.37% (w/v), 0.38% (w/v), 0.39% (w/v), 0.4% (w/v), 0.41% (w/v), 0.42% (w/v), 0.43% (w/v), 0.44% (w/v), 0.45% (w/v), 0.46% (w/v), 0.47% (w/v), 0.48% (w/v), 0.49% (w/v), 0.5% (w/v), 0.51% (w/v), 0.52% (w/v), 0.53% (w/v), 0.54% (w/v), 0.55% (w/v), 0.56% (w/v), 0.57% (w/v), 0.58% (w/v), 0.59% (w/v), 0.6% (w/v), 0.61% (w/v), 0.62% (w/v), 0.63% (w/v), 0.64% (w/v), 0.65% (w/v), 0.66% (w/v), 0.67% (w/v), 0.68% (w/v), 0.69% (w/v), 0.7% (w/v), 0.71% (w/v), 0.72% (w/v), 0.73% (w/v), 0.74% (w/v), 0.75% (w/v), 0.76% (w/v), 0.77% (w/v), 0.78% (w/v), 0.79% (w/v), 0.8% (w/v), 0.81% (w/v), 0.82% (w/v), 0.83% (w/v), 0.84% (w/v), 0.85% (w/v), 0.86% (w/v), 0.87% (w/v), 0.88% (w/v), 0.89% (w/v), 0.9% (w/v), 0.91% (w/v), 0.92% (w/v), 0.93% (w/v), 0.94% (w/v), 0.95% (w/v), 0.96% (w/v), 0.97% (w/v), 0.98% (w/v), 0.99% (w/v), or 1% (w/v) benzalkonium chloride.

In certain embodiments, the absorption enhancer is an alkylsaccharide. In certain embodiments, the alkylsaccharide is chosen from dodecyl maltoside, tetradecyl maltoside (TDM) and sucrose dodecanoate.

In certain embodiments, the alkylsaccharide is dodecyl maltoside (the alkylglycoside 1-O-n-dodecyl-β-D-maltopyranoside, alternately referred to as lauryl-β-D-maltopyranoside, dodecyl maltopyranoside, and DDM; $C_{24}H_{46}O_{11}$, often referred to by the trade name Intravail®). Alkylsaccharides are used in commercial food and personal care products and have been designated Generally Recognized as Safe (GRAS) substances for food applications. They are non-irritating enhancers of transmucosal absorption that are odorless, tasteless, non-toxic, non-mutagenic, and non-sensitizing in the Draize test up to a 25% concentration. Alkylsaccharides increase absorption by increasing paracellular permeability, as indicated by a decrease in transepithelial electrical resistance; they may also increase transcytosis. The effect is short-lived. Other alkylsaccharides include tetradecyl maltoside (TDM) and sucrose dodecanoate.

In certain embodiments, an intranasal formulation comprises between about 0.05% (w/v) and about 2.5% (w/v) Intravail®. In certain embodiments, an intranasal formulation comprises between about 0.1% (w/v) and about 0.5% (w/v) Intravail®. In certain embodiments, an intranasal formulation comprises between about 0.15% (w/v) and about 0.35% (w/v) Intravail®. In certain embodiments, an intranasal formulation comprises between about 0.15% (w/v) and about 0.2% (w/v) Intravail®. In certain embodiments, an intranasal formulation comprises about 0.18% (w/v) Intravail®. In certain embodiments, an intranasal formulation comprises about 0.2% (w/v) to about 0.3%

(w/v) Intravail®. In certain embodiments, an intranasal formulation comprises about 0.25% (w/v) Intravail®.

In certain embodiments, the absorption enhancer is Intravail® (dodecyl maltoside).

In certain embodiments, the absorption enhancer in the intranasal formulation is a combination of dodecyl maltoside and benzalkonium chloride. While the use of dodecyl maltoside or benzalkonium chloride as an absorption enhancer in the intranasal formulations described herein provides bioavailability of intranasal epinephrine, the combination of dodecyl maltoside and benzalkonium chloride as absorption enhancers in the intranasal formulations described herein provides pharmacokinetics that closely match pharmacokinetics obtained through intramuscular injection of epinephrine.

In certain embodiments, each dose dispensed from the device of the pharmaceutical formulation comprises between about 0.4 mg and about 2.40 mg per dose epinephrine, or a salt thereof, and between 0.1 and 0.50 mg Intravail® (dodecyl maltoside).

In certain embodiments, each dose dispensed from the device of the formulation comprises between about 0.5 mg and about 2.0 mg per dose epinephrine, or a salt thereof, and about between 0.1 and 0.50 mg Intravail® (dodecyl maltoside).

In certain embodiments, each dose dispensed from the device of the formulation comprises between about 0.75 mg and about 1.5 mg per dose epinephrine, or a salt thereof, and between 0.1 and 0.50 mg Intravail® (dodecyl maltoside).

In certain embodiments, each dose dispensed from the device of the formulation comprises between about 0.9 mg and about 1.15 mg per dose epinephrine, or a salt thereof, and about 0.25 mg Intravail® (dodecyl maltoside).

In certain embodiments, each dose dispensed from the device of the formulation comprises about 1.0 mg per dose epinephrine, or a salt thereof, and about 0.25 mg Intravail® (dodecyl maltoside).

In certain embodiments, the pharmaceutical formulation additionally comprises a chelating agent or antioxidant (stabilizing agent) to improve stability. In certain embodiments, the chelating/stabilizing agent is EDTA.

Examples of additional stabilizing agents include: acacia, agar, albumin, alginic acid, aluminum stearate, ammonium alginate, ascorbic acid, ascorbyl palmitate, bentonite, butylated hydroxytoluene (BHT), calcium alginate, calcium stearate, carboxymethylcellulose calcium, carboxymethylcellulose sodium, carrageenan, cellulose, microcrystalline, carboxymethylcellulose sodium, ceratonia, colloidal silicon dioxide, cyclodextrins, diethanolamine, edetates, ethylcellulose, ethylene glycol palmitostearate, glycerin monostearate, guar gum, hectorite, hydroxypropyl betadex, hydroxypropyl cellulose, hypromellose, inulin, invert sugar, lauric acid, lecithin, magnesium aluminum silicate, mineral oil and lanolin alcohols, monoethanolamine, pectin, pentetic acid, phospholipids, polacrilin potassium, poloxamer, polyvinyl alcohol, potassium alginate, potassium chloride, povidone, propyl gallate, propylene glycol, propylene glycol alginate, raffinose, sodium acetate, sodium alginate, sodium borate, sodium stearyl fumarate, sorbitol, stearyl alcohol, sulfobutylether b-cyclodextrin, tagatose, trehalose, triethanolamine, white wax, xanthan gum, xylitol, yellow wax, and zinc acetate.

Examples of additional chelating agents include: citric acid monohydrate, disodium edetate, edetate calcium disodium, edetic acid, fumaric acid, malic acid, maltol, pentetic acid, sodium edetate, and trisodium edetate.

In certain embodiments, the pharmaceutical formulation comprises benzalkonium chloride. In certain embodiments, the pharmaceutical formulation comprises about 0.005% (w/v) to about 1% (w/v) benzalkonium chloride.

In its capacity as a surfactant, benzalkonium chloride can affect the surface tension of droplets from a delivered nasal spray plume, producing spherical or substantially spherical particles having a narrow droplet size distribution (DSD), as well as the viscosity of a liquid formulation.

In certain embodiments, the absorption enhancer is an alkylsaccharide, for example, a nonionic alkylsaccharide surfactant such as an alkylglycoside and a sucrose ester of fatty acids that consists of an aliphatic hydrocarbon chain coupled to a sugar moiety by a glycosidic or ester bond, respectively. In certain embodiments, the absorption enhancer is an alkylmaltoside (e.g., a tetradecyl maltoside (TDM), a dodecyl maltoside (DDM), etc.). In certain embodiments, the absorption enhancer is sucrose dodecanoate. Alkylsaccharides are used in commercial food and personal care products and have been designated Generally Recognized as Safe (GRAS) substances for food applications. They are non-irritating enhancers of transmucosal absorption that are odorless, tasteless, non-toxic, non-mutagenic, and non-sensitizing in the Draize test up to a 25% concentration. Without being bound to any theory, it is believed that alkylsaccharides increase absorption by increasing paracellular permeability, as indicated by a decrease in transepithelial electrical resistance; they may also increase transcytosis. The effect may be short-lived. In its capacity as an absorption enhancer, alkylmaltosides (e.g., a tetradecyl maltoside (TDM), a dodecyl maltoside (DDM), etc.) can affect the surface tension of droplets from a delivered nasal spray plume, producing spherical or substantially spherical particles having a narrow droplet size distribution (DSD), as well as the viscosity of a liquid formulation.

In certain embodiments, the absorption enhancer is the alkylsaccharide 1-O-n-dodecyl-β-D-maltopyranoside (alternately referred to as lauryl-β-D-maltopyranoside, dodecyl maltopyranoside, dodecyl maltoside, and DDM; $C_{24}H_{46}Q_{11}$; often referred to by the trade name Intravail®). In certain embodiments, an intranasal formulation comprises about 0.01% (w/v) to about 2.5% (w/v) DDM. In certain embodiments, an intranasal formulation comprises about 0.1% (w/v) to about 0.5% (w/v) DDM. In certain embodiments, an intranasal formulation comprises about 0.15% (w/v) to about 0.35% (w/v) DDM. In certain embodiments, an intranasal formulation comprises about 0.15% (w/v) to about 0.2% (w/v) DDM. In certain embodiments, an intranasal formulation comprises about 0.18% (w/v) DDM. In certain embodiments, an intranasal formulation comprises about 0.2% (w/v) to about 0.3% (w/v) DDM. In certain embodiments, an intranasal formulation comprises about 0.25% (w/v) DDM.

In sugar chemistry, an anomer is either of a pair of cyclic stereoisomers (designated a or R) of a sugar or glycoside, differing only in configuration at the hemiacetal (or hemiketal) carbon, also called the anomeric carbon or reducing carbon. If the structure is analogous to one with the hydroxyl group on the anomeric carbon in the axial position of glucose, then the sugar is an alpha anomer. If, however, that hydroxyl is equatorial, the sugar is a beta anomer. For example, α-D-glucopyranose and β-D-glucopyranose, the two cyclic forms of glucose, are anomers. Likewise, alkylglycosides occur as anomers. For example, dodecyl β-D-maltoside and dodecyl α-D-maltoside are two cyclic forms of dodecyl maltoside. The two different anomers are two distinct chemical structures, and thus have different physical and chemical properties. In one aspect of the invention, the alkylglycoside of the present invention is a R anomer. In an exemplary aspect, the alkylglycoside is a R anomer of an alkylmaltoside, such as tetradecyl-β-D-maltoside (TDM).

In some embodiments, the alkylglycoside used is a substantially pure alkylglycoside. As used herein a "substantially pure" alkylglycoside refers to one anomeric form of the alkylglycoside (either the a or R anomeric forms) with less than about 2% of the other anomeric form, preferably less than about 1.5% of the other anomeric form, and more preferably less than about 1% of the other anomeric form. In one aspect, a substantially pure alkylgycoside contains greater than 98% of either the a or R anomer. In another aspect, a substantially pure alkylgycoside contains greater than 99% of either the a or R anomer. In another aspect, a substantially pure alkylgycoside contains greater than 99.5% of either the a or R anomer. In another aspect, a substantially pure alkylgycoside contains greater than 99.9% of either the a or R anomer.

In certain embodiments, described herein is an aqueous formulation suitable for intranasal administration comprising: epinephrine; water; and one or more ingredients selected from absorption enhancers, chelating agents, antioxidants, stabilizing agents, surfactants, isotonicity agents, and pH adjusting agents.

In certain embodiments, described herein is an aqueous formulation suitable for intranasal administration comprising: epinephrine; water; and one or more ingredients selected from alkylglycosides, chitosan, alkylcyclodextrins, benzalkonium chloride, sodium chloride, and EDTA.

In certain embodiments, described herein is an aqueous formulation suitable for intranasal administration comprising: epinephrine; water; and one or more ingredients selected from dodecyl maltoside (DDM), tetradecyl maltoside (TDM), benzalkonium chloride, sodium chloride, hydrochloric acid, and EDTA. In certain other embodiments, described herein is an aqueous formulation suitable for intranasal administration comprising: epinephrine; water; and one or more ingredients selected from dodecyl maltoside (DDM), benzalkonium chloride, sodium chloride, and EDTA.

In certain embodiments, described herein is an aqueous formulation suitable for intranasal administration comprising: epinephrine; water; dodecyl maltoside (DDM); and one or more ingredients selected from benzalkonium chloride, sodium chloride, pH adjusting agents, and EDTA.

In certain embodiments, described herein is an aqueous formulation suitable for intranasal administration comprising: epinephrine; water; benzalkonium chloride; and one or more ingredients selected from dodecyl maltoside (DDM), sodium chloride, pH adjusting agents, and EDTA.

In certain embodiments, described herein is an aqueous formulation suitable for intranasal administration comprising: epinephrine; water; dodecyl maltoside (DDM) or benzalkonium chloride or a combination of dodecyl maltoside (DDM) and benzalkonium chloride; and one or more additional ingredients selected from sodium chloride, pH adjusting agents, and EDTA.

pH adjusting agents include acids described herein (e.g. hydrochloric acid, citric acid), buffers (e.g. phosphate, acetate, and citrate buffers), and bases (e.g. sodium hydroxide, sodium citrate, sodium bicarbonate, sodium carbonate).

In certain embodiments, described herein is an aqueous formulation suitable for intranasal administration comprising: about 0.5% (w/v) to about 2.5% (w/v) epinephrine; water; and one or more ingredients selected from: about 0.05% (w/v) to about 2.5% (w/v) dodecyl maltoside (DDM); about 0.005% (w/v) to about 1% (w/v) benzalkonium chloride; about 0.2% (w/v) to about 1.2% (w/v) sodium chloride, optional hydrochloric acid or sodium hydroxide in a sufficient amount to adjust the pH to a final pH of about 4.0 to about 5.0; and about 0.05% (w/v) to about 2.0% (w/v) EDTA.

In certain embodiments, described herein is an aqueous formulation suitable for intranasal administration comprising: i) about 0.5% (w/v) to about 2.5% (w/v) epinephrine; ii) water; iii) about 0.05% (w/v) to about 2.5% (w/v) dodecyl maltoside (DDM) or about 0.005% (w/v) to about 1% (w/v) benzalkonium chloride, or a combination of about 0.05% (w/v) to about 2.5% (w/v) dodecyl maltoside (DDM) and about 0.005% (w/v) to about 1% (w/v) benzalkonium chloride; and iv) one or more ingredients selected from a) about 0.2% (w/v) to about 1.2% (w/v) sodium chloride; b) optional hydrochloric acid or sodium hydroxide in an amount sufficient to adjust the pH to a final pH of about 4.0 to about 5.0; and c) about 0.05% (w/v) to about 2.0% (w/v) EDTA.

In certain embodiments, described herein is an aqueous formulation suitable for intranasal administration comprising: i) about 0.9% (w/v) to about 2.0% (w/v) epinephrine; ii) water; iii) about 0.05% (w/v) to about 2.5% (w/v) dodecyl maltoside (DDM), or about 0.005% (w/v) to about 1% (w/v) benzalkonium chloride, or a combination of about 0.05% (w/v) to about 2.5% (w/v) dodecyl maltoside (DDM) and about 0.005% (w/v) to about 1% (w/v) benzalkonium chloride; and iv) one or more ingredients selected from a) about 0.2% (w/v) to about 1.2% (w/v) sodium chloride; b) optional hydrochloric acid or sodium hydroxide hydrochloric acid in an amount sufficient to adjust the pH to a final pH of about 4.0 to about 5.0; and c) about 0.05% (w/v) to about 2.0% (w/v) EDTA.

In certain embodiments, described herein is an aqueous formulation suitable for intranasal administration comprising: about 0.5% (w/v) to about 2.5% (w/v) epinephrine; water; about 0.05% (w/v) to about 2.5% (w/v) dodecyl maltoside (DDM); about 0.005% (w/v) to about 1% (w/v) benzalkonium chloride; about 0.2% (w/v) to about 1.2% (w/v) sodium chloride, hydrochloric acid in a sufficient amount to adjust the pH to a final pH of about 4.0 to about 5.0; and about 0.05% (w/v) to about 2.0% (w/v) EDTA.

In certain embodiments, described herein is an aqueous formulation suitable for intranasal administration comprising: epinephrine; water; one or more absorption enhancement agents; an isotonicity agent; a stabilizing agent; a preservative; and optional pH adjustment agents to adjust pH to pH 3 to 6. In certain embodiments, described herein is an aqueous formulation suitable for intranasal administration comprising: epinephrine; water; one or more absorption enhancement agents (e.g. dodecyl maltoside; benzalkonium chloride; or a combination of dodecyl maltoside and benzalkonium chloride); an isotonicity agent (e.g. sodium chloride); a stabilizing agent (e.g. EDTA or disodium EDTA); a preservative (e.g. benzalkonium chloride); and optional pH adjustment agents to adjust pH to pH 3 to 6. In certain embodiments, described herein is an aqueous formulation suitable for intranasal administration comprising: epinephrine; water; one or more absorption enhancement agents (e.g. dodecyl maltoside; benzalkonium chloride; or a combination of dodecyl maltoside and benzalkonium chloride); an isotonicity agent (e.g. sodium chloride); a stabilizing agent (e.g. EDTA or disodium EDTA); a preservative (e.g. benzalkonium chloride); an antioxidant; a buffering agent; and optional pH adjustment agents to adjust pH to pH 3 to 6.

In certain embodiments, described herein is an aqueous formulation suitable for intranasal administration comprising: epinephrine; water; dodecyl maltoside or benzalkonium chloride or a combination of dodecyl maltoside and benzalkonium chloride; sodium chloride; EDTA or disodium EDTA; and optional pH adjustment agents to adjust pH to pH 3 to 6.

In certain embodiments, described herein is an aqueous formulation suitable for intranasal administration comprising: about 0.5% (w/v) to about 2.5% (w/v) epinephrine; water; about 0.05% (w/v) to about 2.5% (w/v) dodecyl maltoside or about 0.005% (w/v) to about 1% (w/v) benzalkonium chloride or a combination of about 0.05% (w/v) to about 2.5% (w/v) dodecyl maltoside and about 0.005% (w/v) to about 1% (w/v) benzalkonium chloride; about 0.2% (w/v) to about 1.2% (w/v) sodium chloride; about 0.05% (w/v) to about 2.0% (w/v) EDTA or disodium EDTA; and optional pH adjustment agents to adjust pH to pH 3 to 6.

In some embodiments, a 100 µL sample of the aqueous formulation suitable for intranasal administration comprises less than about 2.5 mg of epinephrine. In some embodiments, a 100 µL sample of the aqueous formulation suitable for intranasal administration comprises about 0.5 mg to about 2.5 mg of epinephrine. In some embodiments, a 100 µL sample of the aqueous formulation suitable for intranasal administration comprises about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, or about 2.5 mg of epinephrine.

Nasal Drug Delivery Devices and Kits

Also provided are nasal drug delivery devices comprising a formulation described herein. In certain embodiments, the device is pre-primed. In certain embodiments, the device can be primed before use. In certain embodiments, the device can be actuated with one hand.

Nasal delivery is considered an attractive, safe, and easy-to-administer route for needle-free, systemic drug delivery, especially when rapid absorption and effect are desired. In addition, nasal delivery may help address issues related to poor bioavailability, slow absorption, drug degradation, and adverse events (AEs) in the gastrointestinal tract and avoids the first-pass metabolism in the liver.

Liquid nasal formulations are mainly aqueous solutions, but suspensions, emulsions, liposomes, and microspheres can also be delivered. Other liquid formulations can comprise liposomes, microspheres, mixed aqueous-organic formulations, non-aqueous formulations, dry powder and retentive formulations (gels). In traditional spray pump systems, antimicrobial preservatives are typically required to maintain microbiological stability in liquid formulations. Metered spray pumps have dominated the nasal drug delivery market since they were introduced. The pumps typically deliver 100 µL (25-250 µL) per spray, and they offer high reproducibility of the emitted dose and plume geometry in in vitro tests.

Examples of standard metered spray pumps include those offered by Aptar Pharma, Inc., such as the multi-dose "classic technology platform" nasal spray devices, and by BD Medical-Pharmaceutical Systems, such as the Accuspray™ system. Such devices comprise a reservoir which holds multiple doses of the nasal spray formulation (e.g., 50, 100, 150, 200, 60, or 120 doses), a closure (e.g., screw, crimp, or snap-on), and an actuator which delivers anywhere from 45 to 1000 µL (e.g. 50, 100, 140, 150, or 200 µL) of fluid per actuation to comprise a single dose. The actuator may be configured to count doses, deliver gel formulations, deliver in an upside-down configuration, etc.

In traditional multi-use spray pump systems, antimicrobial preservatives are typically required to maintain microbiological stability in liquid formulations. However, preservative-free systems are also available, e.g. the Advanced Preservative Free (APF) system from Aptar, which is vented, contains a filter membrane for air flow which prevents contamination, has a metal-free fluid path for oxidizing formulations, and can be used in any orientation. Additional nasal spray devices from Aptar and others are optimized with dispenser tips that prevent clogging (useful for high-viscosity and high-volatile formulations), actuators that do not need re-priming after long periods of disuse, etc. Additional nasal spray devices are propellant driven. Yet additional nasal spray devices include dry powder inhalers.

The particle size and plume geometry can vary within certain limits and depend on the properties of the pump, the formulation, the orifice of the actuator, and the force applied. The droplet size distribution of a nasal spray is a critical parameter, since it significantly influences the in vivo deposition of the drug in the nasal cavity. The droplet size is influenced by the actuation parameters of the device and the formulation. The prevalent median droplet size should be between about 30 and about 100 m. If the droplets are too large (> about 120 µm), deposition takes place mainly in the anterior parts of the nose, and if the droplets are too small (< about 10 µm), they can possibly be inhaled and reach the lungs and oral cavity, which should be avoided because of safety reasons. In its capacity as a surfactant, benzalkonium chloride and alkylmaltosides (e.g., a tetradecyl maltoside (TDM), a dodecyl maltoside (DDM), etc.) can affect the surface tension of droplets from a delivered nasal spray plume, producing spherical or substantially spherical particles having a narrow droplet size distribution (DSD), as well as the viscosity of a liquid formulation.

Plume geometry, droplet size and DSD of the delivered plume subsequent to spraying may be measured under specified experimental and instrumental conditions by appropriate and validated and/or calibrated analytical procedures known in the art. These include photography, laser diffraction, and impaction systems (cascade impaction, NGI). Plume geometry, droplet size and DSD can affect pharmacokinetic outcomes such as $C_{max}$, $T_{max}$, and dose proportionality.

Droplet size distribution can be controlled in terms of ranges for the D10, D50, D90, span [(D90−D10)/D50], and percentage of droplets less than 10 mm. In certain embodiments, the formulation will have a narrow DSD. In certain embodiments, the formulation will have a D(v,50) of 30-70 μm and a D(v,90)<100 μm.

In certain embodiments, the percent of droplets less than 10 μm will be less than 10%. In certain embodiments, the percent of droplets less than 10 μm will be less than 5%. In certain embodiments, the percent of droplets less than 10 μm will be less than 2%. In certain embodiments, the percent of droplets less than 10 μm will be less than 1%.

In certain embodiments, the formulation when dispensed by actuation from the device will produce a uniform circular plume with an ovality ratio close to 1. Ovality ratio is calculated as the quotient of the maximum diameter ($D_{max}$) and the minimum diameter ($D_{min}$) of a spray pattern taken orthogonal to the direction of spray flow (e.g., from the "top"). In certain embodiments, the ovality ratio is less than ±2.0. In certain embodiments, the ovality ratio is less than ±1.5. In certain embodiments, the ovality ratio is less than ±1.3. In certain embodiments, the ovality ratio is less than ±1.2. In certain embodiments, the ovality ratio is less than ±1.1.

The details and mechanical principles of particle generation for different types of nasal aerosol devices has been described. See, Vidgren and Kublik, *Adv. Drug Deliv. Rev.* 29:157-77, 1998. Traditional spray pumps replace the emitted liquid with air, and preservatives are therefore required to prevent contamination. However, driven by the studies suggesting possible negative effects of preservatives, pump manufacturers have developed different spray systems that avoid the need for preservatives. These systems use a collapsible bag, a movable piston, or a compressed gas to compensate for the emitted liquid volume (on the World Wide Web at aptar.com and on the World Wide Web at rexam.com). The solutions with a collapsible bag and a movable piston compensating for the emitted liquid volume offer the additional advantage that they can be emitted upside down, without the risk of sucking air into the dip tube and compromising the subsequent spray. This may be useful for some products where the patients are bedridden and where a head-down application is recommended. Another method used for avoiding preservatives is that the air that replaces the emitted liquid is filtered through an aseptic air filter. In addition, some systems have a ball valve at the tip to prevent contamination of the liquid inside the applicator tip. More recently, pumps have been designed with side-actuation. The pump was designed with a shorter tip to avoid contact with the sensitive mucosal surfaces. New designs to reduce the need for priming and re-priming, and pumps incorporating pressure point features to improve the dose reproducibility and dose counters and lock-out mechanisms for enhanced dose control and safety are available (on the World Wide Web at rexam.com and on the World Wide Web at aptar.com).

Traditional, simple single, bi-dose and multi-use metered-dose spray pumps require priming and some degree of overfill to maintain dose conformity for the labeled number of doses. They are well suited for drugs to be administered daily over a prolonged duration, but due to the priming procedure and limited control of dosing, unless a specialty device is selected, they are less suited for drugs with a narrow therapeutic window of time in which to use the device, particularly if they are not used often. For expensive drugs and drugs intended for single administration or sporadic use and where tight control of the dose and formulation is of importance, single-dose (UDS) or bi-dose spray (BDS) devices are preferred (on the World Wide Web at aptar.com). A simple variant of a single-dose spray device (MAD™) is offered by LMA (LMA, Salt Lake City, UT, USA; on the World Wide Web at lmana.com). A nosepiece with a spray tip is fitted to a standard syringe. The liquid drug to be delivered is first drawn into the syringe and then the spray tip is fitted onto the syringe. This device has been used in academic studies to deliver, for example, a topical steroid in patients with chronic rhinosinusitis and in a vaccine study. A pre-filled device based on the same principle for one or two doses (Accuspray™, Becton Dickinson Technologies, Research Triangle Park, NC, USA; on the World Wide Web at bdpharma.com) is used to deliver the influenza vaccine FluMist™ (on the World Wide Web at flumist.com), approved for both adults and children in the US market. A similar device for two doses was marketed by a Swiss company for delivery of another influenza vaccine a decade ago.

Pre-primed single- and bi-dose devices are also available, and consist of a reservoir, a piston, and a swirl chamber (see, e.g., the UDS UnitDose™ and BDS BiDose™ devices from Aptar, formerly Pfeiffer). The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like Imitrex® (on the World Wide Web at gsk.com) and Zomig® (on the World Wide Web at az.com; Pfeiffer/Aptar single-dose device), the marketed influenza vaccine Flu-Mist (on the World Wide Web at flumist.com; Becton Dickinson single-dose spray device), and the intranasal formulation of naloxone for opioid overdose rescue, Narcan Nasal® (on the World Wide Web at narcan.com; Adapt Pharma) are delivered with this type of device.

In certain embodiments, the 90% confidence interval for dose delivered per actuation is ± about 2%. In certain embodiments, the 95% confidence interval for dose delivered per actuation is ± about 2.5%.

Historically, intranasal administration of drugs in large volume, such as from syringes adapted with mucosal atomizer devices (MADs), has encountered difficulty due to the tendency of some of the formulation to drip back out of the nostril or down the nasopharynx. Accordingly, in certain embodiments, upon nasal delivery of said pharmaceutical formulation to said patient, less than about 20% of said pharmaceutical formulation leaves the nasal cavity via drainage into the nasopharynx or externally. In certain embodiments, upon nasal delivery of said pharmaceutical formulation to said patient, less than about 10% of said pharmaceutical formulation leaves the nasal cavity via drainage into the nasopharynx or externally. In certain embodiments, upon nasal delivery of said pharmaceutical formulation to said patient, less than about 5% of said pharmaceutical formulation leaves the nasal cavity via drainage into the nasopharynx or externally.

Current container closure system designs for inhalation spray drug products include both pre-metered and device-metered presentations using mechanical or power assistance and/or energy from patient inspiration for production of the spray plume. Pre-metered presentations contain previously measured doses or a dose fraction in some type of units (e.g., single or multiple blisters or other cavities) that are subsequently inserted into the device during manufacture or by the patient before use. Typical device-metered units have a reservoir containing formulation sufficient for multiple doses that are delivered as metered sprays by the device itself when activated by the patient.

With aseptic techniques, the use of preservatives may not be required in pre-primed devices, but overfill is required resulting in a waste fraction similar to the metered-dose, multi-dose sprays. To emit 100 µL, a volume of 125 µL is filled in the device (Pfeiffer/Aptar single-dose device) used for the intranasal migraine medications Imitrex™ (sumatriptan) and Zomig™ (zolmitriptan) and about half of that for a bi-dose design. Sterile drug products may be produced using aseptic processing or terminal sterilization. Terminal sterilization usually involves filling and sealing product containers under high-quality environmental conditions. Products are filled and sealed in this type of environment to minimize the microbial and particulate content of the in-process product and to help ensure that the subsequent sterilization process is successful. In most cases, the product, container, and closure have low bioburden, but they are not sterile. The product in its final container is then subjected to a sterilization process such as heat, irradiation, or chemical (gas). In an aseptic process, the drug product, container, and closure are first subjected to sterilization methods separately, as appropriate, and then brought together. Because there is no process to sterilize the product in its final container, it is critical that containers be filled and sealed in an efficient quality environment. Aseptic processing involves more variables than terminal sterilization. Before aseptic assembly into a final product, the individual parts of the final product generally can be subjected to various sterilization processes. For example, glass containers are subjected to dry heat; rubber closures are subjected to moist heat; and liquid dosage forms are subjected to filtration. Each of these manufacturing processes requires validation and control.

Devices recited herein may employ any of the pharmaceutical formulations, and are useful in the methods disclosed herein.

Accordingly, provided herein are devices adapted for nasal delivery of a pharmaceutical formulation to a patient, comprising a reservoir with a therapeutically effective amount of epinephrine.

In certain embodiments, epinephrine is the only pharmaceutically active compound in the pharmaceutical formulation.

In certain embodiments, the volume of the pharmaceutical formulation in the reservoir is not more than about 140 µL.

In certain embodiments, the volume of the pharmaceutical formulation in the reservoir is above about 125 µL and less than 140 µL.

In certain embodiments, about 100 µL of the pharmaceutical formulation in the reservoir is delivered to the patient in one actuation.

In some embodiments, about 100 µL of the pharmaceutical formulation in the reservoir is delivered to the patient in one actuation and comprises less than about 2.5 mg of epinephrine. In some embodiments, about 100 µL of the pharmaceutical formulation in the reservoir is delivered to the patient in one actuation and comprises about 0.5 mg to about 2.5 mg of epinephrine. In some embodiments, about 100 µL of the pharmaceutical formulation in the reservoir is delivered to the patient in one actuation and comprises about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, or about 2.5 mg of epinephrine.

In certain embodiments, the pharmaceutical formulation further comprises one or more excipients selected from water, EDTA, and sodium chloride. In certain embodiments, the pharmaceutical formulation further comprises benzalkonium chloride.

In some embodiments, about 100 µL of the aqueous pharmaceutical formulation in the reservoir is delivered to the patient in one actuation and comprises epinephrine, dodeclymaltoside or benzalkonium chloride or a combination of dodeclymaltoside and benzalkonium chloride, EDTA, and NaCl.

In certain embodiments, the pharmaceutical formulation is substantially free of antimicrobial preservatives.

In certain embodiments, the pharmaceutical formulation further comprises a compound which acts as a preservative, absorption enhancer and/or a cationic surfactant; an isotonicity agent; a stabilizing agent; and an amount of acid or base sufficient to achieve a pH of about 3.5 to about 6.0. The use of absorption enhancers, such as alkylsaccharides, cyclodextrins, and chitosans may increase the rate at which epinephrine is absorbed. In general, absorption enhancers provide improved pharmacokinetic outcomes such as increased $C_{max}$, reduced $T_{max}$, and dose proportionality compared to both intramuscular formulations and intranasal formulations that do not contain an absorption enhancer. Without being bound to any theory, such absorption enhancers typically operate by affecting two primary mechanisms for nasal absorption: paracellular transport via opening of tight junctions between cells, and transcellular transport or transcytosis through cells via vesicle carriers.

Some absorption enhancing excipients can alter the paracellular and/or transcellular pathways, others can extend residence time in the nasal cavity or prevent metabolic changes. Without an absorption enhancer, the molecular-weight limit for nasal absorption is about 1 kDa, while administration of drugs in conjunction with absorption enhancers can enable the absorption of molecules from 1-30 kDa. Intranasal administration of most absorption enhancers, however, can cause nasal mucosa damage. Maggio, *J. Excipients and Food Chem.* 5(2):100-12, 2014. Examples of absorption enhancers include aprotinin, benzalkonium chloride, benzyl alcohol, capric acid, ceramides, cetylpyridinium chloride, chitosan, cyclodextrins, deoxycholic acid, decanoyl carnitine, EDTA, glycocholic acid, glycodeoxycholic acid, glycofurol, glycosylated sphingosines, glycyrrhetinic acids, 2-hydroxypropyl-β-cyclodextrin, laureth-9, lauric acid, lauroyl carnitine, lauryl sulfate, lysophosphatidylcholine, menthol, poloxamer 407, poloxamer F68, poly-L-arginine, polyoxyethylene-9-lauryl ether, polysorbate 80, propylene glycol, quillaia saponin, salicylic acid, β-sitosterol-β-D-glucoside, sucrose cocoate, taurocholic acid, taurodeoxycholic acid, taurodihydrofusidic acid, and alkylsaccharides, such as dodecyl maltoside, tetradecyl maltoside and sucrose dodecanoate.

Epinephrine may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. The acid addition salts may be obtained as the direct products of compound synthesis. In the alternative, the free base may be dissolved in a suitable solvent containing the appropriate acid and the salt isolated by evaporating the solvent or otherwise separating the salt and solvent. The salt may form solvates with standard low molecular weight solvents using methods known to the skilled artisan.

In certain embodiments, the device is filled with the pharmaceutical formulation using sterile filling.

In certain embodiments, the pharmaceutical formulation is chemically storage-stable for about twelve months at about 25° C. and about 60% relative humidity and about six months at about 40° C. and about 75% relative humidity.

In some embodiments, intranasal epinephrine is delivered as an aqueous solution, aqueous suspension, aqueous emulsion, non-aqueous solution, non-aqueous suspensions, non-aqueous emulsion, a solution with halogenated hydrocarbon propellant(s), or as a dry powder. In some embodiments, aqueous formulations are sprayed into the nostril. In some embodiments, aqueous formulations are aerosolized by liquid nebulizers employing either hydraulic or ultrasonic atomization. Propellant-based systems may use suitable pressurized metered-dose inhalers (pMDIs). Dry powders may use dry powder inhaler devices (DPIs), which are capable of dispersing the drug substance effectively.

Propellants typically used include chlorofluorocarbons, hydrochlorofluorocarbons, hydrofluorocarbons, hydrocarbons, and compressed gases.

In some embodiments, intranasal epinephrine is delivered as a nasal aerosol produced by a nasal pressurized metered-dose inhalers (pMDIs). In some embodiments, the pMDI is a hydrofluoroalkane (HFA)-based pMDI for nasal use. Like spray pumps, nasal pMDIs produce a localized deposition on the anterior non-ciliated epithelium of the nasal vestibule and in the anterior parts of the narrow nasal valve, but due to quick evaporation of the spray delivered with a pMDI, noticeable "drip-out" may be less of an issue.

In some embodiments, epinephrine is delivered with a nebulizer. Nebulizers use compressed gasses (air, oxygen, and nitrogen) or ultrasonic or mechanical power to break up medical solutions and suspensions into small aerosol droplets that can be directly inhaled into the nose. The smaller particles and slow speed of the nebulized aerosol increase penetration to the target sites in the middle and superior meatuses and the paranasal sinuses.

In some embodiments, epinephrine is delivered with a pulsating aerosol generated via a perforated vibrating membrane. In some embodiments, the pulsation membrane nebulizer is VibrENT (PARI Pharma GmbH). In some embodiments, epinephrine is delivered with a pulsating aerosol in combination with breathing techniques In some embodiments, epinephrine is delivered with Bi-Directional™ delivery technology (e.g. Bi-Directional™ Exhalation Delivery Systems (EDS); OptiNose).

In some embodiments, epinephrine is delivered with an atomizer. In some embodiments, the atomizer is a handheld battery-driven atomizer intended for nasal drug delivery. In some embodiments, the atomizer atomizes liquids by producing a vortical flow on the droplets as they exit the device. Such devices include the ViaNase™ atomizer (by Kurve Technology Inc., Lynnwood, WA, USA). In some embodiments, the atomizer is is a nasal atomizer driven by highly pressurized nitrogen gas.

In some embodiments, intranasal epinephrine is delivered with a nasal powder device. In some embodiments, the nasal powder device is a nasal powder inhaler, nasal powder sprayer, or nasal powder insufflator. Powder sprayers typically have a compressible compartment to provide a pressure that when released creates a plume of powder particles fairly similar to that of a liquid spray. Breath-actuated inhalers require the user to use his or her own breath to inhale the powder into the nostril from a blister or capsule. Nasal insufflator devices consist of a mouthpiece and a nosepiece that are fluidly connected. Delivery occurs when the subject exhales into the mouthpiece to close the velum, and the airflow carries the powder particles into the nose through the device nosepiece.

In some embodiments, the nasal powder inhaler is a blister based powder inhaler. Typically, the blister is pierced before use and the device nosepiece placed into one nostril. The subject closes the other nostril with the finger and inhales the powder into the nose. Representative devises include BiDose™/Prohaler™, and Twin-lizer™.

Representative nasal powder sprayers include, but are not limited to, UnidoseDP™, Fit-lizer™, Monopowder™, Solu-Vent™)

In some embodiments, the nasal powder sprayer is a capsule-based, single-dose powder devices. In one such embodiment, the capsule-based, single-dose powder device consists of a chamber that cuts off the top and bottom of the capsule when inserted. A plastic chamber is compressed by hand, compressed air passes through a one-way valve and the capsule during actuation, and the powder is emitted.

In some embodiments, the nasal powder sprayer consists of an air-filled compartment that is compressed until a pin ruptures a membrane to release pressure that emits a plume of powder.

In some embodiments, the nasal powder sprayer consists of a plunger that when pressed creates a positive pressure that ruptures a membrane to expel the powder.

In some embodiments, the nasal powder insufflator requires the subject to blow into one end of the tube while the other end is inserted into the vestibule of the nostril.

In some embodiments, intranasal epinephrine is delivered with a breath-powered Bi-Directional™ delivery device. A breathpowered Bi-Directional™ nasal delivery device utilizes the exhaled breath to deliver the drug into the nose. Breath-powered Bi-Directional™ devices consist of a mouthpiece and a sealing nosepiece with an optimized frusto-conical shape and comfortable surface that mechanically expands the first part of the nasal valve. The user slides a sealing nosepiece into one nostril until it forms a seal with the flexible soft tissue of the nostril opening, at which point, it mechanically expands the narrow slit-shaped part of the nasal triangular valve. The user then exhales through an attached mouthpiece. When exhaling into the mouthpiece against the resistance of the device, the soft palate (or velum) is automatically elevated by the positive oropharyngeal pressure, isolating the nasal cavity from the rest of the respiratory system. Owing to the sealing nosepiece, the dynamic pressure that is transferred from the mouth through the device to the nose further expands the slit-like nasal passages. This "breath-powered" mechanism enables release of liquid or powder particles into an air stream that enters one nostril, passes entirely around the nasal septum, and exits through the opposite nostril. Actuation of drug release in devices employing this approach use manual triggering or mechanisms automatically triggered by flow and/or pressure.

Single-Dose Devices

In certain embodiments, the device is a single-dose device, wherein the pharmaceutical formulation is present in one reservoir, and wherein the therapeutically effective amount of the epinephrine is delivered essentially by one actuation of the device.

Also provided herein is a single-use, pre-primed device adapted for nasal delivery of a pharmaceutical formulation to a patient by one actuation of the device into one nostril of the patient, having a single reservoir comprising about 100 μL of a pharmaceutical formulation as disclosed herein.

In certain embodiments, the device is actuatable with one hand.

In certain embodiments, the delivery time is less than about 30 seconds. In certain embodiments, the delivery time is less than about 25 seconds. In certain embodiments, the delivery time is less than about 20 seconds. In certain embodiments, the delivery time is less than about 15 seconds.

In certain embodiments, the 90% confidence interval for dose delivered per actuation is ± about 2%. In certain embodiments, the 95% confidence interval for dose delivered per actuation is ± about 2.5%.

In certain embodiments, upon nasal delivery of the formulation to the patient, less than about 20%, less than about 15%, less than about 10%, or less than about 5%, of the formulation leaves the nasal cavity via drainage into the nasopharynx or externally, as provided above.

In certain embodiments, said formulation is chemically storage-stable for about twelve months at about 25° C. and about 60% relative humidity and/or about six months at about 40° C. and about 75% relative humidity.

Bi-Dose Devices

In certain embodiments, said device is a bi-dose device, wherein a first volume of said formulation is present in a first reservoir and a second volume of said formulation is present in a second reservoir, and wherein said therapeutically effective amount is delivered essentially by a first actuation of said device into a first nostril of said patient and a second actuation of said device into a second nostril of said patient.

In certain embodiments, said first volume and said second volume combined is equal to not more than about 380 μL.

In certain embodiments, about 100 μL of said first volume of said formulation is delivered by said first actuation.

In certain embodiments, about 100 μL of said second volume of said formulation is delivered by said second actuation.

In certain embodiments, said bi-dose device is actuatable with one hand.

In certain embodiments, the delivery time is less than about 30 seconds. In certain embodiments, the delivery time is less than about 25 seconds. In certain embodiments, the delivery time is less than about 20 seconds. In certain embodiments, the delivery time is less than about 15 seconds.

In certain embodiments, the 90% confidence interval for dose delivered per actuation is ± about 2%. In certain embodiments, the 95% confidence interval for dose delivered per actuation is ± about 2.5%.

In certain embodiments, upon nasal delivery of the formulation to the patient, less than about 20%, less than about 15%, less than about 10%, or less than about 5%, of the formulation leaves the nasal cavity via drainage into the nasopharynx or externally.

Also provided are embodiments wherein any embodiment above may be combined with any one or more of these embodiments, provided the combination is not mutually exclusive.

Indications

Also provided are formulations and devices for use in treating conditions mediated by adrenergic receptors, and/or one or more symptoms thereof, and methods of treatment of such conditions comprising administering the formulations and using the devices disclosed herein.

In certain embodiments, the condition is (1) treatment of acute hypersensitivity, such as a type-1 hypersensitivity reaction (for example such as an anaphylactoid reaction (systemic allergic reaction) to foods, drugs, animal serums, insect bites and stings, and other allergens, see below), (2) treatment of acute asthmatic attacks to relieve bronchospasm not controlled by inhalation or subcutaneous administration of other solutions of the drug, (3) treatment and prophylaxis of cardiac arrest and/or attacks of transitory atrioventricular (A-V) heart block with syncopal seizures (Stokes-Adams Syndrome), (4) to increase mean arterial blood pressure in adult patients with hypotension associated with septic shock, (5) for induction and maintenance of mydriasis during intraocular surgery.

In certain embodiments, the type-1 hypersensitivity reaction (systemic allergic reaction) is chosen from allergic asthma, allergic conjunctivitis, allergic rhinitis (hay fever), anaphylaxis, angioedema, urticaria (hives), eosinophilia, antibiotic allergy (e.g. to penicillin or cephalosporin), and food allergy (e.g. to peanuts or shellfish).

In certain embodiments, the type-1 hypersensitivity reaction (systemic allergic reaction) is anaphylaxis.

Symptoms of anaphylaxis include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, and intercostal retractions.

In certain embodiments, the symptom of the type-1 hypersensitivity reaction (systemic allergic reaction) is chosen from generalized hives (urticatria), itching (pruritus), flushing, swelling (angioedema) of the afflicted tissues, a burning sensation of the skin (common in those with angioedema), swelling of the tongue or throat, respiratory symptoms such as shortness of breath, wheezes, or stridor shortness of breath, coronary artery spasm, myocardial infarction, dysrhythmia, or cardiac arrest (those with underlying coronary disease are at greater risk of cardiac effects), tachycardia, bradycardia, and a Bezold-Jarisch reflex.

In certain embodiments, the type-1 hypersensitivity reaction (systemic allergic reaction) is caused by stinging insects (e.g., order Hymenoptera, which include bees, wasps, hornets, yellow jackets and fire ants), biting insects (e.g., triatoma, mosquitoes), allergen immunotherapy, foods, drugs, diagnostic testing substances (e.g. radiocontrast media) and other allergens, as well as idiopathic anaphylaxis or exercise-induced anaphylaxis.

In certain embodiments, the cardiac arrest is out-of-hospital cardiac arrest.

Also provided are embodiments wherein any embodiment above may be combined with any one or more of these embodiments, provided the combination is not mutually exclusive.

EXAMPLES

The following examples are provided for illustrative purposes only and not to limit the scope of the claims provided herein.

Example 1. Epinephrine Formulations for Clinical Use

A representative procedure for the preparation of formulations for clinical use is described. The Formulation Excipient Solution (FES) can be made in advance (up to 7 days) and stored at room temperature. The epinephrine stock solution (ESS) should be made fresh within 72 hours of dosing, protected from light and excessive oxidation and stored at 2-8° C. until 2 hours before use. A mixture of equal volumes of sterile filtered FES and ESS will result in a solution of epinephrine, dodecylmaltoside (DDM), EDTA, benzalkonium chloride (BZK) in saline for use in the clinical protocols below.

A 200 mL batch of Formulation Excipient Solution (FES) is prepared by weighing 0.80 g (0.75-0.85 g) of EDTA into a 200 mL volumetric flask and dissolving in ~150 mL of Sterile Saline; weighing 1.00 g (0.95-1.05 g) of Intravail® DDM, quantitatively transferring to the EDTA solution, and mixing until dissolved (solution should be clear and colorless); if necessary, using gentle heating (40-60° C.) aid solution, then cooling to room temperature once dissolved; adding the desired amount of a BZK solution (or adding BZK as a solid) and adding to the mixing Intravail®/EDTA mixture; adding the appropriate amount of 1 N HCl to attain a pH of 4 (e.g. approximately 20 mL), and diluting QS to volume with Sterile Saline, and stirring until the mixture is uniform. The pH of the FES solution may be measured and recorded.

Epinephrine Stock Solution (ESS) 10 mg/mL should be freshly prepared, protected from light (e.g. with foil, the use of brown colored lights, etc.), and use within 72 hours of dosing. To formulate a 100 mL batch of final 10 mg/mL product: ensure 100 mL volumetric flask is wrapped in foil prior to adding FES Solution; add 50 mL of FES Solution to each of two foil wrapped 100 mL flasks (50 mL per flask); weigh and add 1.0 g (0.95-1.05 g) of epinephrine (E4250 Sigma Aldrich) into each of the two 100 mL flasks; mix each until uniform; measure the pH of each flask and record.

Final Dosing Formulations (FDF) are prepared by filling appropriate sprayers capable of delivering 100 μL per spray with appropriate amounts of ESS (e.g. about 5.0 mL of ESS for Aptar multi-dose spray devices or about 125 μL of ESS for uni-dose spray devices).

Representative epinephrine formulations for clinical use are presented in Table 2, Table 3, and Table 4.

TABLE 2

Representative Epinephrine Formulations for Clinical Use.

| Ingredients | Quantity per mL | | | | | |
|---|---|---|---|---|---|---|
| (-)-Epinephrine USP (mg) | 3 | 5 | 10 | 10 | 10 | 20 |
| DDM (mg) | 2.5 | 2.5 | 2.5 | 2.5 | 2.5 | 2.5 |
| Disodium EDTA USP (mg) | 2.0 | 2.0 | 2.0 | 2.0 | 2.0 | 2.0 |
| BZK USP (mg) | 0.1 | 0.2 | 0.2 | 0.4 | 0.6 | 0.2 |
| Sodium chloride USP (mg) | 8.23 | 8.23 | 8.23 | 8.23 | 8.23 | 8.23 |
| 1N HCl (mL) | 0.051 | 0.051 | 0.051 | 0.051 | 0.051 | 0.051 |
| 0.1N HCl and/or 0.1 NaOH | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 |
| Purified water, Millipore, Type I | QS to 1 mL | QS to 1 mL | QS to 1 mL | QS to 1 mL | QS to 1 mL | QS to 1 mL |

TABLE 3

Representative Epinephrine Formulations for Clinical Use.

| Ingredients | Quantity per mL | | | | | | |
|---|---|---|---|---|---|---|---|
| (-)-Epinephrine USP (mg) | 3 | 5 | 6.5 | 10 | 13 | 15 | 20 |
| DDM (mg) | 2.5 | 2.5 | 2.5 | 2.5 | 2.5 | 2.5 | 2.5 |
| Disodium EDTA USP (mg) | 2.0 | 2.0 | 2.0 | 2.0 | 2.0 | 2.0 | 2.0 |
| BZK USP (mg) | 0.4 | 0.4 | 0.4 | 0.4 | 0.4 | 0.4 | 0.4 |
| Sodium chloride USP (mg) | 8.23 | 8.23 | 8.23 | 8.23 | 8.23 | 8.23 | 8.23 |
| 1N HCl (mL) | 0.051 | 0.051 | 0.051 | 0.051 | 0.051 | 0.051 | 0.051 |
| 0.1N HCl and/or 0.1 NaOH | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 |
| Purified water, Millipore, Type I | QS to 1 mL | QS to 1 mL | QS to 1 mL | QS to 1 mL | QS to 1 mL | QS to 1 mL | QS to 1 mL |

TABLE 4

Representative Epinephrine Formulations for Clinical Use.

| Ingredients | Quantity per mL | | | | | | | |
|---|---|---|---|---|---|---|---|---|
| (-)-Epinephrine USP (mg) | 10 | 10 | 10 | 10 | 10 | 10 | 10 | 10 |
| Dodecylmaltoside (DDM) (mg) | 2.5 | 2.5 | 2.5 | 2.5 | 2.5 | 2.5 | 2.5 | 2.5 |
| Disodium EDTA USP (mg) | 2.0 | 2.0 | 2.0 | 2.0 | 2.0 | 2.0 | 2.0 | 2.0 |
| Benzalkonium Chloride USP (mg) | 0.4 | 0.4 | 0.4 | 0.4 | 0.4 | 0.4 | 0.4 | 0.4 |
| Sodium chloride USP (mg) | 8.23 | 8.23 | 8.23 | 8.23 | 8.23 | 8.23 | 8.23 | 8.23 |
| Butylated hydroxyanisole (BHA) (mg) | — | 0.1 | 0.1 | — | — | — | — | — |
| Citric acid monohydrate (mg) | — | — | 0.42 | — | 4.2 | — | 4.2 | — |
| Isoascorbic Acid (mg) | — | — | — | 0.1 | 0.1 | — | — | — |
| D-α-Tocopherol polyethylene glycol 1000 succinate (mg) | — | — | — | — | — | 5.0 | 5.0 | — |
| Sodium metabisulfite (mg) | — | — | — | — | — | — | — | 0.05 |
| 1N HCl 0.1N HCl | 0.051 mL Adjust to pH 3.8-4.2 | 0.051 mL Adjust to pH 3.8-4.2 | 0.051 mL Adjust to pH 3.8-4.2 | 0.051 mL Adjust to pH 3.8-4.2 | 0.051 mL Adjust to pH 3.8-4.2 | 0.051 mL Adjust to pH 3.8-4.2 | 0.051 mL Adjust to pH 3.8-4.2 | 0.051 mL Adjust to pH 3.8-4.2 |

TABLE 4-continued

Representative Epinephrine Formulations for Clinical Use.

| Ingredients | Quantity per mL | | | | | | | |
|---|---|---|---|---|---|---|---|---|
| 0.1 NaOH | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 | Adjust to pH 3.8-4.2 |
| Purified water, Millipore, Type I | QS to 1 mL | QS to 1 mL | QS to 1 mL | QS to 1 mL | QS to 1 mL | QS to 1 mL | QS to 1 mL | QS to 1 mL |

Example 2: Clinical Protocols

The following clinical protocols were carried out, or may be carried out, in healthy human volunteers to assess the safety, optimal dosing, and pharmacokinetics of intranasal epinephrine.

Example 2A: First Clinical Study

Objective. The primary objective of this study was to assess the comparative bioavailability of epinephrine after intranasal administration and intramuscular administration as intramuscular epinephrine delivered by auto injector in healthy volunteers under fasted conditions. A secondary objective was to evaluate the safety and tolerability of intranasal (IN) epinephrine in healthy volunteers.

Study Design. A Phase 1, open-label, randomized, single-dose, two-treatment, crossover study was carried out that consisted of a screening period, baseline period, and an open-label treatment period. In the screening period, subjects underwent screening within 21 days prior to entering into the open-label treatment phase of the study. In the baseline period, within 24 hours of dosing, initial assessments were taken; in some cases, screening and baseline visits could be combined if all assessments are done within 24 hours of dosing.

In the Open-Label Treatment Period, twelve (12) eligible subjects were randomized after an overnight fast to receive single 0.3 mg doses of intranasal epinephrine and intramuscular epinephrine delivered by auto injector. Blood samples were collected for 360 minutes after dosing. Treatments were separated by a minimum 24 hours wash out period. Safety assessments were performed on each study day and subjects released after discharge assessments on Day 1. Subjects were followed for 6 hours after the administration of the last dose of study drug.

Plasma samples from all subjects that completed two periods of the study were analyzed. Blood samples for the measurement of plasma concentrations of epinephrine, norepinephrine and dihydroxyphenylglycol (DHPG) (metabolite) were collected before (0, pre-dose) and at 2, 4, 6, 8, 10, 12.5, 15, 20, 25, 45, 60, 90, 120, 150, 180, 240 and 360 minutes after dosing. Actual blood collection times can vary as follows: 1) ±1 minutes for the 2 to 20 minute samples, 2) ±2 minutes for the 25 to 90 minute samples, and 3) ±5 minutes for the 120 to 360 minute samples. Actual sampling times were recorded.

Study Drugs and Administration. Each 100 μL IN dose of intranasal epinephrine formulation contained, in addition to 0.3 mg epinephrine, 0.25% (w/v) dodecylmaltoside (0.25 mg), 0.04% (w/v) benzalkonium chloride (BZK) (0.04 mg), ethylenediaminetetraacetic acid (EDTA) in 10 mM pH 4.0 acetate buffer. The intramuscular epinephrine delivered by auto injector delivered 0.3 mg epinephrine by intramuscular injection.

Subjects were fasted prior to administration of either IN or IM epinephrine. Each 100 μL spray was administered to the left nostril via a commercially-available multiple dose nasal spray device marketed by Aptar Pharma. Priming of the device (activation 5 times) was done in a hood or priming box within 30 minutes prior to dosing the subject.

Participants. The study included healthy male adult volunteers (up to 12) between the ages of 18 and 55 years, inclusive, who gave written, informed consent. Other inclusion criteria included: body weight more than 50 kg; mass index between 18 and 28 kg/(height in m)$^2$ (BMI), inclusive; no medical history of hypertension and cardiovascular disease; blood pressure and heart rate within normal range at screening and baseline; no clinically significant abnormal findings in medical history, on physical examination, electrocardiogram (QTcF<450 msec), or clinical laboratory results during screening; and agreement to remain confined in house until study end and willing to comply with all required study procedures.

Exclusion criteria included: history of clinically significant gastrointestinal, renal, hepatic, neurologic, hematologic, endocrine, oncologic, respiratory, immunologic, psychiatric, or cardiovascular disease, severe seasonal or non-seasonal allergies, nasal polyps, no nasal piercings, or any nasal passage abnormality that could interfere with nasal spray administration, or any other condition which, in the opinion of the Principal Investigator, would jeopardize the safety of the subject or impact the validity of the study results; smoked within 6 months prior to screening; significant traumatic injury, major surgery or open biopsy within 30 days prior to study screening; history of allergic or adverse responses to epinephrine or any comparable or similar product; an abnormal diet (such as one that severely restricts specific basic food groups [e.g., ketogenic diet], limits calories [e.g., fast], and/or requires the use of daily supplements as a substitute for the foods typically eaten at mealtimes), during the four (4) weeks preceding the study; donation of blood or plasma within 30 days of the first dose of study drug; participation in a clinical trial within 30 days prior to the first dose of study drug (non-interventional trial acceptable); inadequate or difficult venous access that could jeopardize the quality or timing of the PK samples; positive blood screen for HIV, Hepatitis B surface antigen (HbSAg), or Hepatitis C, or a positive urine screen for alcohol (saliva test may be utilized at baseline), drugs of abuse, or cotinine.

Additionally, during the study, subjects were not permitted: to take OTC products, including vitamins and supplements, for the seven (7) days preceding the study; to use any prescription medication within 14 days prior to the first dose of study drug or during the study unless approved by the Principal Investigator and medical monitor; to use oral and/or nasal decongestants within 14 days prior to the first dose of study drug or during the study; to smoke or use tobacco products for six (6) months prior to the first dose of Study Drug and for the duration of the study; or to engage in strenuous exercise during the confinement period of the study.

Safety. Adverse events were collected and reviewed to evaluate the safety and tolerability of intranasal (IN) epinephrine. Other safety measures included vital sign measurement. Objective evaluations of nasal irritation were assessed after each administration of study drug using a 6-point (0→5) score. The scoring was done by a trained observer based on an assessment of the nasal mucosa prior to dosing (baseline) and at 30 (±5 min) minutes, and 1 (±10 min), 2 (±15 min), 4 (±30 min), and 6 (±30 min) hours post dose. Irritation was assessed by evaluating the degree of mucosal inflammation and bleeding. The subjects were required to report any incident of bleeding or inflammation in-between the actual evaluation time points.

An unconstrained visual analog scale (VAS) that consists of a 10 cm (100 mm) horizontal straight line was used to assess acute pain following each administration of the intranasal intranasal (IN) epinephrine drug product. The ends of the scale were defined as extreme limits of pain sensation: 0=no pain, 10=extreme pain. The subjects were asked to mark a point on the scale which best describes their intensity of pain and discomfort just prior to dosing (baseline) and at 15 (±2 min) and 30 (±5 min) minutes, and 1 (±10 min) hour post dose. The location of the marking at each time point was measured and noted as the reported score.

Pharmacokinetic Analysis. Pharmacokinetic parameters for epinephrine, norepinephrine and DHPG will be calculated using non-compartmental analysis were calculated: maximum plasma concentration ($C_{max}$), time to $C_{max}$ ($t_{max}$), area under the curve to the final time with a concentration equal to or greater than the lower limit of quantitation [$AUC_{(0-t)}$] and to infinity [$AUC_{(inf)}$], elimination rate constant ($\lambda z$) and half-life ($t_{1/2}$), and, for epinephrine only, clearance (CL/F) and volume of distribution (Vz/F) uncorrected for bioavailability (F).

Non-GCP pharmacokinetic analysis was performed using WinNonlin version 7.0. The lower limit of bioanalytical quantification was 20 pg/mL. Plasma concentration designated as BLQ were given a value of 20 pg/mL. The pharmacokinetic parameters $C_{max}$, $AUC_{(0-t)}$, and $AUC_{(inf)}$ for epinephrine, norepinephrine and DHPG were compared among treatments using an analysis of variance (ANOVA) model with treatment, period, sequence, and subject within sequence as the classification variables using the natural logarithms of the data. Baseline corrected $C_{max}$ was calculated from the uncorrected $C_{max}$–PreDose concentration. Baseline corrected $AUC_{0-t}$ was calculated from the uncorrected $AUC_{0-t}$–PreDose concentration x $t_{last}$. Confidence intervals (90%) were constructed for the geometric mean ratios, intranasal-to-intramuscular epinephrine of the three parameters using the log-transformed data and the two one-sided t-tests procedure. The point estimates and confidence limits will be exponentiated back to the original scale. Comparability between intranasal (IN) epinephrine and intramuscular epinephrine was assessed from the geometric mean ratios and 90% confidence intervals for the three parameters.

Results. Mean plasma concentration of epinephrine from IN administration remained significantly below that of epinephrine from intramuscular epinephrine delivered by auto injector throughout the study, as shown in FIG. 3. Intranasal administration of epinephrine using the above intranasal epinephrine formulation resulted in significantly lower exposure ($C_{max}$ and $AUC_{0-t}$) of the parent compound epinephrine compared to intramuscular epinephrine delivered by auto injector, as shown below in Table 5. There were no related adverse events reported. The pH was between 3 and 4.

TABLE 5

Intramuscular and Intranasal Administraton of Epinephrine.

| | Intramuscular 0.3 mg | | | Intranasal 0.3 mg | | |
|---|---|---|---|---|---|---|
| | $C_{max}$ (pg/mL) | $AUC_{0-t}$ (hr*pg/mL) | $t_{max}$ (min) | $C_{max}$ (pg/mL) | $AUC_{0-t}$ (hr*pg/mL) | $t_{max}$ (min) |
| Mean | 333 | 19878 | 18 | 83 | 8932 | 53 |
| SD | 196 | 6051 | | 53 | 6385 | |
| Min | 71 | 7493 | 6 | 19 | 767 | 2 |
| Median | 311 | 19606 | 20 | 83 | 7771 | 23 |
| Max | 729 | 30381 | 45 | 222 | 23011 | 240 |
| CV % | 59 | 30 | | 64 | 71 | |
| Geometric Mean | 280 | 18854 | | 69 | 6619 | |
| CV % Geometric Mean | 72 | 38 | | 73 | 117 | |

Example 2B: Second Clinical Study

Objective. The primary objectives of this study were to determine the optimal dose of a formulation of intranasal epinephrine (IN-Epi) to be used in a study of, and in that study to assess, the comparative bioavailability of epinephrine after intranasal administration and intramuscular administration by injection (EpiPen®) injection in healthy volunteers under fasted conditions. A secondary objective was to evaluate the safety and tolerability of the formulation of intranasal epinephrine in healthy volunteers.

Study Design. A Phase 1, dose escalation followed by a 12 subject open-label, randomized, single-dose, two-treatment, two-period, crossover studies was conducted as follows.

A dose escalation in three subjects was conducted to determine the optimal dose of epinephrine. In the Screening Period, subjects underwent screening within 28 days prior to entering into the study. Three (3) subjects were subsequently enrolled and received IN-Epi doses of 0.5 mg, 1.0 mg and 2.0 mg epinephrine by IN administration (formulated at pH 5.5 to 6.0) after an overnight fast. Blood samples were collected for 360 minutes after dosing. Treatments were separated by a minimum 24 hours wash out period.

Thereafter, comparative bioavailabilty of the intranasal formulation to intramuscular injection was assessed in twelve subjects in an open-label, randomized, single-dose, two-treatment, two-period, crossover study that consisted of a screening period, baseline period, and an open-label treatment period. In the Screening Period, subjects underwent screening within 28 days prior to entering into the study. In the Open-Label Treatment Period, twelve (12) eligible subjects were randomized to 1.0 mg of IN-Epi or a 0.3 mg dose of epinephrine injection by IM administration (EpiPen®) after an overnight fast to receive single doses. Blood samples are collected for 360 minutes after dosing. Treatments are separated by a minimum 24 hours wash out period.

Safety assessments were performed at each of the study day and subjects could be released after discharge assessment. Subjects were followed for 6 hours after the administration of the last dose of study drug.

The study was carried out in part as disclosed above. For all parts of the study, the following procedures were performed as follows.

Study Drugs and Administration. Each 100 μL IN dose of epinephrine formulation contained, in addition to 0.5 mg, 1.0 mg, or 2.0 mg (5 mg/mL, 10 mg/mL, or 20 mg/mL) of IN-Epi, 0.25% (w/v) dodecylmaltoside (0.25 mg), 0.04% (w/v) benzalkonium chloride (BZK) (0.04 mg), and Ethylenediaminetetraacetic acid (EDTA) in 0.9% (w/v) saline, at pH 4.5 (3.5 to 5.0). The commercially available EpiPen® delivers 0.3 mg epinephrine by intramuscular injection.

Subjects were fasted prior to administration of either IN or IM epinephrine. Each 100 μL spray was administered to the left nostril via a commercially-available multiple dose nasal spray device marketed by Aptar Pharma. Priming of the device (activation 5 times) was done in a hood or priming box within 30 minutes prior to dosing the subject.

Participants. A total of fifteen (15) males were enrolled in the study. Plasma samples from all subjects that complete the study were analyzed. Blood samples for the measurement of plasma concentrations of epinephrine were collected before (0, pre-dose) and at 2, 4, 6, 8, 10, 12.5, 15, 20, 25, 45, 60, 90, 120, 150, 180, 240 and 360 minutes after dosing. Actual blood collection times could vary as follows: 1) ±1 minutes for the 2 to 20 minute samples, 2) ±2 minutes for the 25 to 90 minute samples, and 3) ±5 minutes for the 120 to 360 minute samples.

Inclusion criteria. Participants: were male, between ages 18 and 30, inclusive; gave written informed consent; had body weight more than 50 kg and mass index between 18 and 28 kg/m$^2$, inclusive; had no family/medical history of hypertension and cardiovascular disease within the past 10 years; have blood pressure within normal range (i.e. <140/90 mmHg) at screening; had no clinically significant abnormal findings in the medical history, on physical examination, electrocardiogram (QTcF<450 msec), or clinical laboratory results during screening; and agreed to remain confined in house during appropriate study times and willing to comply with all required study procedures.

Exclusion Criteria. Exclusion criteria included history of clinically significant gastrointestinal, renal, hepatic, neurologic, hematologic, endocrine, oncologic, pulmonary, immunologic, psychiatric, or cardiovascular disease, severe seasonal or non seasonal allergies, nasal polyps, or any nasal passage abnormality that could interfere with nasal spray administration, or any other condition which, in the opinion of the Principal Investigator, would jeopardize the safety of the subject or impact the validity of the study results; had smoked within 6 months prior to screening; significant traumatic injury, major surgery or open biopsy within 30 days prior to study screening; history of allergic or adverse responses to epinephrine or any comparable or similar product; had been on an abnormal diet (such as one that severely restricts specific basic food groups [e.g., ketogenic diet], limits calories [e.g., fast], and/or required the use of daily supplements as a substitute for the foods typically eaten at mealtimes), during the four (4) weeks preceding the study; donated blood or plasma within 30 days of the first dose of study drug; participation in a clinical trial within 30 days prior to the first dose of study drug; inadequate or difficult venous access that may jeopardize the quality or timing of the PK samples; positive blood screen for HIV, Hepatitis B surface antigen (HbSAg), or Hepatitis C, or a positive urine screen for alcohol, drugs of abuse, or cotinine.

Additionally, during the study, subjects were not permitted: to take OTC products, including vitamins and supplements, for the seven (7) days preceding the study; to use any prescription medication within 14 days prior to the first dose of study drug or during the study unless approved by the Principal Investigator and medical monitor; to use oral and/or nasal decongestants within 14 days prior to the first dose of study drug or during the study; to smoke or use tobacco products for six (6) months prior to the first dose of Study Drug and for the duration of the study; or to engage in strenuous exercise during the confinement period of the study.

Safety. Adverse events were collected and were or will be reviewed to evaluate the safety and tolerability of IN-Epi. Other safety measures will include vital sign measurements.

Objective evaluations of nasal irritation were assessed after each administration of study drug using a 6-point (0→5) score. The scoring was done by a medically trained observer based on an assessment of the nasal mucosa prior to dosing (baseline) and at 30 (±5 min) minutes, and 1 (±10 min), 2 (±15 min), 4 (±30 min), and 6 (±30 min) hours post dose. Irritation was assessed by evaluating the degree of mucosal inflammation and bleeding. Subjects were also required to report any incident of bleeding or inflammation in-between the actual evaluation time points.

An unconstrained visual analog scale (VAS) that consists of a 10 cm (100 mm) horizontal straight line was used to assess acute pain following each administration of the IN-Epi drug product. The ends of the scale were defined as extreme limits of pain sensation: 0=no pain, 10=extreme pain. Subjects were asked to mark a point on the scale which best describes their intensity of pain and discomfort just prior to dosing (baseline) and at 15 (±2 min) and 30 (±5 min) minutes, and 1 (±10 min) hour post dose. The location of the marking at each time point was measured and noted as the reported score.

Pharmacokinetic Analysis. Pharmacokinetic parameters for epinephrine were calculated using non-compartmental analysis: maximum plasma concentration ($C_{max}$), time to $C_{max}$ ($t_{max}$), area under the curve to the final time with a concentration equal to or greater than the lower limit of quantitation [$AUC_{(0-t)}$] and to infinity [$AUC_{(inf)}$], elimination rate constant (λz) and half-life ($t_{1/2}$), and, for epinephrine only, clearance (CL/F) and volume of distribution (Vz/F) uncorrected for bioavailability (F).

Pharmacokinetic parameters $C_{max}$, $AUC_{(0-t)}$, and $AUC_{(inf)}$ for epinephrine were compared among treatments using an analysis of variance (ANOVA) model with treatment, period, sequence, and subject within sequence as the classification variables using the natural logarithms of the data. Confidence intervals (90%) were constructed for the geometric mean ratios, IN-Epi-to-EpiPen®, of the three parameters using the log-transformed data and the two one-sided t-tests procedure. The point estimates and confidence limits were exponentiated back to the original scale. Comparability between IN and IM epinephrine were assessed from the geometric mean ratios and 90% confidence intervals for the three parameters.

Results. Results for the dose escalation portion of the study are given below in Table 6 and in FIGS. 4, 5, 6, and 7. Intranasal formulations of epinephrine formulated as disclosed above at doses of 0.5, 1.0, and 2.0 mg in saline at pH 4.0 (3.5-5.0 acceptable) were administered to three subjects. Table 6 below gives the mean pharmacokinetic parameters for the three doses.

TABLE 6

Mean pharmacokinetic parameters for three doses of intranasal epinephrine.

| | 0.5 mg | | | 1.0 mg | | | 2.0 mg | | |
|---|---|---|---|---|---|---|---|---|---|
| | $t_{max}$ (min) | $C_{max}$ (pg/mL) | $AUC_{0-t}$ (min* pg/mL) | $t_{max}$ (min) | $C_{max}$ (pg/mL) | $AUC_{0-t}$ (min* pg/mL) | $t_{max}$ (min) | $C_{max}$ (pg/mL) | $AUC_{0-t}$ (min* pg/mL) |
| Mean | 28.3 | 234 | 24000 | 12.7 | 586 | 43900 | 12.5 | 2470 | 166000 |
| SD | 27.4 | 22.4 | 5090 | 6.43 | 369 | 18400 | 2.5 | 1370 | 80800 |
| CV % | 96.8 | 9.55 | 21.2 | 50.8 | 63 | 41.8 | 20 | 55.4 | 48.7 |
| Geo Mean | 21.1 | 234 | 23600 | 11.7 | 468 | 41100 | 12.3 | 2230 | 154000 |

As can be seen, $T_{max}$ was lower, and $C_{max}$ and AUC higher, for all doses of intranasal epinephrine than in the previous study. These trends were more marked with increasing dose. In particular, the 1.0 and 2.0 mg formulations each exhibited a $T_{max}$ that was lower than intramuscular epinephrine delivered by auto injector as used in the previous study, and a $C_{max}$ that was higher. AUC for all intranasal formulations was higher than for intramuscular epinephrine delivered by auto injector for all doses.

FIGS. 4 and 5 show the mean time-vs-concentration curves for the 0.5, 1.0, and 2.0 mg intranasal formulations of epinephrine. FIGS. 6 and 7 duplicate the data in FIGS. 4 and 5, but overlay it on the epinephrine auto injector data from Study 2A to illustrate the pharmacokinetic differences between, for example, the 1.0 and 2.0 mg intranasal doses of epinephrine and intramuscular epinephrine auto injector. These figures also provide a relevant contrast to FIG. 3, where intranasal epinephrine was formulated in acetate buffer at pH 3-4.

The results from the dose escalation portion of the study show, in contrast to previous studies, that epinephrine can be formulated to achieve significant bioavailability. At certain doses, the pharmacokinetics of intranasal epinephrine so formulated appears superior to intramuscular epinephrine delivered by auto injector, achieving a rapid, IM-injection-like rate of absorption in the first 20 minutes.

Results for the portion of the study comparing bioavailability of IN to IM injection are given below in Tables 7-9c and in FIGS. 8 and 9. Intranasal epinephrine formulated as disclosed above at a dose of 1.0 mg in saline at approximately pH 4.0 was administered to twelve subjects; a further twelve were administered intramuscular epinephrine delivered by auto injector (0.3 mg) in the thigh. Table 7 below shows mean PK parameters for IN and IM epinephrine formulated as disclosed above.

TABLE 7

Mean PK parameters for IN and IM epinephrine.

| | Intranasal 1.0 mg | | | IM Injection Thigh 0.3 mg | | |
|---|---|---|---|---|---|---|
| | $C_{max}$ (pg/mL) | $AUC_{0-t}$ (min*pg/mL) | $t_{max}$ (min) | $C_{max}$ (pg/mL) | $AUC_{0-t}$ (min*pg/mL) | $t_{max}$ (min) |
| N | 12 | 12 | 12 | 12 | 12 | 12 |
| Min | 182 | 28102 | 6 | 64 | 16318 | 20 |
| Max | 484 | 70450 | 150 | 560 | 66792 | 61 |
| Geo Mean | 305 | 44221 | 25 | 236 | 45294 | 25 |
| CV % | 30 | 28 | 161 | 64 | 48 | 183 |
| Geo Mean | | | | | | |

FIGS. 8 and 9 also demonstrate that the plasma time vs. concentration curve for 1.0 mg IN epinephrine is very similar to that for 0.3 mg. IM epinephrine (EpiPen®) administered in the thigh.

Table 8 below shows Cm and partial AUC data comparing the IM and IN routes. Ratio of intranasal as a percent of reference for AUCs are given. The data below demonstrate that 1.0 mg intranasal epinephrine can be formulated to be highly similar to or better than a 0.3 mg intramuscular injection of epinephrine. T

TABLE 8

Comparison of Key Pharmacokinetic Parameters between Intranasal and Intramuscular Administration—Ratio Defined as Intranasal/Intramuscular with 90% Confidence Interval.

| | | 90% Confidence Interval | |
|---|---|---|---|
| Dependent | Ratio % Ref | Lower | Upper |
| $C_{max}$ | 129 | 90 | 185 |
| $AUC_{0-t}$ | 98 | 78 | 122 |
| $AUC_{0-2}^{1/2}$ | 85 | 60 | 120 |
| $AUC_{0-5}$ | 74 | 50 | 109 |
| $AUC_{0-7}^{1/2}$ | 73 | 46 | 116 |
| $AUC_{0-10}$ | 79 | 48 | 130 |
| $AUC_{0-15}$ | 93 | 57 | 150 |
| $AUC_{0-20}$ | 102 | 64 | 163 |

Tables 9a-9c below show comparisons of 9a) the median $t_{max}$, 9b) the distribution of $t_{max}$ values, and 9c) the percent of subjects with $t_{max}$ satisfying the stated condition between intranasal and intramuscular epinephrine.

TABLE 9a

Distribution of tmax Values Resulting After Intranasal and Intramuscular Administration.

| | $t_{max}$ (minutes) | |
|---|---|---|
| Percentile | Intranasal | Intramuscular |
| 25% | 9 | 6 |
| Median (50%) | 20 | 35 |
| 75% | 79 | 60 |

TABLE 9b $t_{max}$ Values Listed in Ascending Order After Intranasal and Intramuscular Administration.

| Intranasal | Intramuscular |
|---|---|
| $t_{max}$ (minutes) | |
| 6 | 4 |
| 8 | 6 |
| 8 | 6 |
| 9 | 6 |
| 10 | 6 |
| 20 | 25 |

TABLE 9b-continued $t_{max}$ Values Listed in Ascending Order After Intranasal and Intramuscular Administration.

| Intranasal | Intramuscular |
|---|---|
| 20 | 25 |
| 20 | 35 |
| 20 | 45 |
| 20 | 60 |
| 45 | 60 |
| 79 | 60 |

TABLE 9c

Percent of Subjects with $t_{max}$ Satisfying Stated Condition After Intranasal and Intramuscular Administration.

| | Percent of Subjects | | Number of Subjects | |
|---|---|---|---|---|
| $t_{max}$ Condition (Min.) | Intranasal | Intramuscular | Intranasal | Intramuscular |
| Less than 40 min. | 83% | 67% | 10 | 8 |
| Less than 35 min. | 83% | 58% | 10 | 7 |
| Between 30 and 45 min. | 8% | 17% | 1 | 2 |
| Between 30 and 40 min. | 0% | 8% | 0 | 1 |
| Between 30 and 35 min. | 0% | 8% | 0 | 1 |

IN-Epi appeared to be safe and well-tolerated, and demonstrated PK parameters equivalent to and in some aspects (e.g. Cmax) are better than epinephrine auto injector.

Additionally, throughout the study, no significant PK differences were observed between 1.0 mg IN epinephrine and the 0.3 mg. IM epinephrine.

Other Embodiments

Also provided are embodiments wherein any embodiment above can be combined with any one or more of these embodiments, provided the combination is not mutually exclusive. Also provided herein are uses in the treatment of indications or one or more symptoms thereof as disclosed herein, and uses in the manufacture of medicaments for the treatment of indications or one or more symptoms thereof as disclosed herein, equivalent in scope to any embodiment disclosed above, or any combination thereof that is not mutually exclusive. The methods and uses may employ any of the devices disclosed herein, or any combination thereof that is not mutually exclusive, or any of the pharmaceutical formulations disclosed herein, or any combination thereof that is not mutually exclusive.

Although the present invention has been described with reference to specific details of certain embodiments thereof in the above examples, it will be understood that modifications and variations are encompassed within the spirit and scope of the invention.

What is claimed is:

1. A method of treating a type-1 hypersensitivity reaction in a human comprising intranasally administering to the human with the type-1 hypersensitivity reaction a nasal spray pharmaceutical formulation comprising between about 1 mg/mL and about 40 mg/mL of epinephrine, or a salt thereof, in a volume between about 25 µL and about 250 µL per dose; wherein epinephrine, or a salt thereof, is the only pharmaceutically active ingredient in the nasal spray pharmaceutical formulation;
wherein the type-1 hypersensitivity reaction comprises allergic asthma, allergic conjunctivitis, allergic rhinitis, anaphylaxis, angioedema, urticaria, eosinophilia, or combinations thereof;
wherein the intranasal administration of the nasal spray pharmaceutical formulation to the human with the type-1 hypersensitivity reaction provides plasma epinephrine concentrations in the human that are efficacious for the elimination of one, more than one, or all of the symptoms of the type-1 hypersensitivity reaction in the human; or
wherein the intranasal administration of the nasal spray pharmaceutical formulation to the human with the type-1 hypersensitivity reaction provides plasma epinephrine concentrations in the human that are efficacious for the prevention of the further progression of one, more than one, or all of the symptoms of the type-1 hypersensitivity reaction in the human.

2. The method of claim 1, wherein each dose of the pharmaceutical formulation comprises between about 5 mg/mL and about 40 mg/mL of epinephrine, or a salt thereof.

3. The method of claim 1, wherein each dose of the pharmaceutical formulation comprises about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine, or a salt thereof.

4. The method of claim 1, wherein each dose of the pharmaceutical formulation comprises about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine, or a salt thereof.

5. The method of claim 1, wherein each dose of the pharmaceutical formulation comprises about 10 mg/mL of epinephrine, or a salt thereof, in a volume between about 50 µL and about 200 µL.

6. The method of claim 1, wherein each dose of the pharmaceutical formulation comprises about 20 mg/mL of epinephrine, or a salt thereof, in a volume between about 50 µL and about 200 µL.

7. The method of claim 1, wherein the pharmaceutical formulation further comprises one or more other agents as excipients selected from the group consisting of absorption enhancement agents, isotonicity agents, stabilizing agents, antioxidants, preservatives, and pH adjustment agents to adjust the pH to a final pH between about 3.0 and about 5.0; and water.

8. The method of claim 1, wherein the pharmaceutical formulation further comprises one or more other agents as excipients selected from the group consisting of absorption enhancement agents, isotonicity agents, stabilizing agents, antioxidants, preservatives, and pH adjustment agents to adjust the pH to a final pH between about 3.0 and about 5.0; and water;

the absorption enhancement agents are selected from the group consisting of alkyl glycosides, fatty acids, bile salts, cyclodextrins, phospholipids, and alcohols;

the isotonicity agents are selected from the group consisting of dextrose, glycerin, mannitol, potassium chloride, and sodium chloride;

the stabilizing agent is ethylenediaminetetraacetic acid (EDTA) or disodium salt thereof;

the antioxidants are selected from the group consisting of alpha tocopherol, D-α-tocopherol polyethylene glycol 1000 succinate, ascorbic acid, isoascorbic acid, butylated hydroxyanisole, citric acid monohydrate, potassium metabisulfite, sodium bisulfite, sodium metabisulfite, and sodium sulfite;

the preservative is benzalkonium chloride; and the pH adjustment agents are selected from the group consisting of adipic acid, ammonium chloride, citric acid, acetic acid, hydrochloric acid, lactic acid, phosphoric acid, propionic acid, sulfuric acid, tartaric acid, sodium hydroxide, sodium citrate, sodium bicarbonate, and sodium carbonate.

9. The method of claim 1, wherein the salt of epinephrine is selected from the group consisting of epinephrine acetate, epinephrine hydrochloride, epinephrine tartrate, epinephrine bitartrate, epinephrine hydrogen tartrate, and epinephrine borate.

10. The method of claim 1, wherein each intranasally delivered dose of the pharmaceutical formulation comprises about 10 mg/mL or about 20 mg/mL of epinephrine, or a salt thereof, in a volume between about 50 µL and about 200 µL; dodecyl maltoside, sodium chloride, sodium metabisulfite, ethylenediaminetetraacetic acid (EDTA) or disodium salt thereof, and benzalkonium chloride as excipients; hydrochloric acid, sodium hydroxide, or both, as excipients in amounts to adjust the pH to a final pH between about 3.0 and about 5.0; and water.

11. The method of claim 1, wherein each intranasally delivered dose of the pharmaceutical formulation comprises about 20 mg/mL of epinephrine, or a salt thereof, in a volume of about 50 µL, about 75 µL, about 100 µL, about 125 µL, about 150 µL, about 175 µL, about 200 µL, or about 250 µL; dodecyl maltoside, sodium chloride, sodium metabisulfite, ethylenediaminetetraacetic acid (EDTA) or disodium salt thereof, and benzalkonium chloride as excipients; hydrochloric acid, sodium hydroxide, or both, as excipients in amounts to adjust the pH to a final pH between about 3.0 and about 5.0; and water.

12. The method of claim 1, wherein each intranasally delivered dose of the pharmaceutical formulation comprises about 10 mg/mL or about 20 mg/mL of epinephrine, or a salt thereof, in a volume of about 100 µL; dodecyl maltoside, sodium chloride, sodium metabisulfite, ethylenediaminetetraacetic acid (EDTA) or disodium salt thereof, and benzalkonium chloride as excipients; hydrochloric acid, sodium hydroxide, or both, as excipients in amounts to adjust the pH to a final pH between about 3.0 and about 5.0; and water.

13. The method of claim 1, wherein each intranasally delivered dose of the pharmaceutical formulation comprises about 20 mg/mL of epinephrine, or a salt thereof, in a volume of about 100 µL; dodecyl maltoside, sodium chloride, sodium metabisulfite, ethylenediaminetetraacetic acid (EDTA) or disodium salt thereof, and benzalkonium chloride as excipients; hydrochloric acid, sodium hydroxide, or both, as excipients in amounts to adjust the pH to a final pH between about 3.0 and about 5.0; and water.

14. A method of treating a type-1 hypersensitivity reaction in a human comprising intranasally administering the human with the type-1 hypersensitivity reaction a nasal spray pharmaceutical formulation comprising in each dose about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine, or a salt thereof, in a volume between about 50 µL and about 250 µL; wherein epinephrine, or a salt thereof, is the only pharmaceutically active ingredient in the nasal spray pharmaceutical formulation; an absorption enhancement agent as an excipient that is dodecyl maltoside; an isotonicity agent as an excipient that is sodium chloride; a stabilizing agent as an excipient that is ethylenediaminetetraacetic acid (EDTA) or disodium salt thereof; a preservative as an excipient that is benzalkonium chloride; an optional antioxidant as an excipient that is sodium metabisulfite; hydrochloric acid, sodium hydroxide, or both, as excipients in sufficient amounts to adjust the pH to a final pH between about 3.0 and about 5.0; and water;

wherein the type-1 hypersensitivity reaction comprises allergic asthma, allergic conjunctivitis, allergic rhinitis, anaphylaxis, angioedema, urticaria, eosinophilia, or combinations thereof;

wherein the intranasal administration of the nasal spray pharmaceutical formulation to the human with the type-1 hypersensitivity reaction provides plasma epinephrine concentrations in the human that are efficacious for the elimination of one, more than one, or all of the symptoms of the type-1 hypersensitivity reaction in the human; or wherein the intranasal administration of the nasal spray pharmaceutical formulation to the human with the type-1 hypersensitivity reaction provides plasma epinephrine concentrations in the human that are efficacious for the prevention of the further progression of one, more than one, or all of the symptoms of the type-1 hypersensitivity reaction in the human.

15. The method of claim 14, wherein the type-1 hypersensitivity reaction comprises anaphylaxis; and the symptoms of anaphylaxis are selected from the group consisting of hives, generalized itching, nasal congestion, wheezing, difficulty breathing, cough, cyanosis, lightheadedness, dizziness, confusion, slurred speech, rapid pulse, palpitations, nausea or vomiting, abdominal pain or cramping, skin redness or skin inflammation, nasal flaring, and intercostal retractions.

16. The method of claim 14, wherein the type-1 hypersensitivity reaction comprises urticaria, or the symptoms of the type-1 hypersensitivity reaction comprise pruritis, flushing, or a burning sensation of the skin.

17. The method of claim 14, wherein each intranasally delivered dose of the pharmaceutical formulation comprises about 10 mg/mL of epinephrine, or a salt thereof, in a volume of about 50 µL, about 75 µL, about 100 µL, about 125 µL, about 150 µL, about 175 µL, about 200 µL, or about 250 µL.

18. The method of claim 14, wherein each intranasally delivered dose of the pharmaceutical formulation comprises about 10 mg/mL of epinephrine, or a salt thereof, in a volume of about 100 µL.

19. The method of claim 14, wherein each intranasally delivered dose of the pharmaceutical formulation comprises about 20 mg/mL of epinephrine, or a salt thereof, in a volume of about 50 μL, about 75 μL, about 100 μL, about 125 μL, about 150 μL, about 175 μL, about 200 μL, or about 250 μL.

20. The method of claim 14, wherein each intranasally delivered dose of the pharmaceutical formulation comprises about 20 mg/mL of epinephrine, or a salt thereof, in a volume of about 100 μL.

21. A method of treating a type-1 hypersensitivity reaction in a human comprising intranasally administering to the human with the type-1 hypersensitivity reaction a pharmaceutical formulation comprising in each dose between about 1 mg/mL and about 40 mg/mL of epinephrine as the only active moiety in the pharmaceutical formulation in a volume between about 25 μL and about 250 μL; wherein the intranasal administration of the pharmaceutical formulation to the human with the type-1 hypersensitivity reaction provides plasma epinephrine concentrations in the human that are efficacious for the elimination of one, more than one, or all of the symptoms of the type-1 hypersensitivity reaction in the human; or wherein the intranasal administration of the pharmaceutical formulation to the human with the type-1 hypersensitivity reaction provides plasma epinephrine concentrations in the human that are efficacious for the prevention of the further progression of one, more than one, or all of the symptoms of the type-1 hypersensitivity reaction in the human.

22. The method of claim 21, wherein each dose of the pharmaceutical formulation comprises about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL of epinephrine as the only active moiety in the pharmaceutical formulation; and wherein the volume of each dose is between about 50 μL and about 250 μL.

23. The method of claim 21, wherein each dose of the pharmaceutical formulation comprises about 5 mg/mL, about 10 mg/mL, about 15 mg/mL, or about 20 mg/mL of epinephrine as the only active moiety in the pharmaceutical formulation; and wherein the volume of each dose is between about 50 μL and about 250 μL.

24. The method of claim 21, wherein the pharmaceutical formulation further comprises one or more other agents as excipients selected from the group consisting of absorption enhancement agents, isotonicity agents, stabilizing agents, antioxidants, preservatives, and pH adjustment agents to adjust the pH to a final pH between about 3.0 and about 5.0; and water.

25. A method of treating a type-1 hypersensitivity reaction in a human comprising intranasally administering to the human with the type-1 hypersensitivity reaction a pharmaceutical formulation comprising in each dose between 0.1 mg and 4 mg of epinephrine as the only active moiety in the pharmaceutical formulation; wherein the intranasal administration of the pharmaceutical formulation to the human with the type-1 hypersensitivity reaction provides plasma epinephrine concentrations in the human that are efficacious for the elimination of one, more than one, or all of the symptoms of the type-1 hypersensitivity reaction in the human; or wherein the intranasal administration of the pharmaceutical formulation to the human with the type-1 hypersensitivity reaction provides plasma epinephrine concentrations in the human that are efficacious for the prevention of the further progression of one, more than one, or all of the symptoms of the type-1 hypersensitivity reaction in the human.

26. The method of claim 25, wherein each dose of the pharmaceutical formulation comprises about 0.5 mg, about 1.0 mg, or about 2.0 mg of epinephrine as the only active moiety in the pharmaceutical formulation, and wherein the volume of each dose of the pharmaceutical formulation is between about 50 μL and about 250 μL.

27. The method of claim 25, wherein the pharmaceutical formulation further comprises one or more other agents as excipients selected from the group consisting of absorption enhancement agents, isotonicity agents, stabilizing agents, antioxidants, preservatives, and pH adjustment agents; and water; wherein the volume of each dose of the pharmaceutical formulation is between about 50 μL and about 250 μL.

28. The method of claim 27, wherein:
the absorption enhancement agents are selected from the group consisting of alkyl glycosides, fatty acids, bile salts, cyclodextrins, phospholipids, and alcohols;
the isotonicity agents are selected from the group consisting of dextrose, glycerin, mannitol, potassium chloride, and sodium chloride;
the stabilizing agent is ethylenediaminetetraacetic acid (EDTA) or disodium salt thereof;
the antioxidants are selected from the group consisting of alpha tocopherol, D-α-tocopherol polyethylene glycol 1000 succinate, ascorbic acid, isoascorbic acid, butylated hydroxyanisole, citric acid monohydrate, potassium metabisulfite, sodium bisulfite, sodium metabisulfite, and sodium sulfite;
the preservative is benzalkonium chloride; and
the pH adjustment agents are selected from the group consisting of adipic acid, ammonium chloride, citric acid, acetic acid, hydrochloric acid, lactic acid, phosphoric acid, propionic acid, sulfuric acid, tartaric acid, sodium hydroxide, sodium citrate, sodium bicarbonate, and sodium carbonate.

29. The method of claim 25, wherein the type-1 hypersensitivity reaction comprises anaphylaxis; and the symptoms of the type-1 hypersensitivity reaction are selected from the group consisting of hives, generalized itching, nasal congestion, wheezing, difficulty breathing, cough, cyanosis, lightheadedness, dizziness, confusion, slurred speech, rapid pulse, palpitations, nausea or vomiting, abdominal pain or cramping, skin redness or skin inflammation, nasal flaring, and intercostal retractions.

30. The method of claim 25, wherein the type-1 hypersensitivity reaction comprises urticaria, and the symptoms of the type-1 hypersensitivity reaction comprise pruritis, flushing, or burning sensation of the skin.

31. A method for the treatment of anaphylaxis in a human comprising intranasally administering to the human with anaphylaxis a single dose of an aqueous pharmaceutical formulation comprising about 1.0 mg to about 2.0 mg of epinephrine as the only pharmaceutically active ingredient in the aqueous pharmaceutical formulation in a volume between about 50 μL and about 250 μL;
wherein the intranasal administration of the single dose to the human with anaphylaxis provides plasma epinephrine concentrations in the human that are efficacious for the elimination of one, more than one, or all of the symptoms of anaphylaxis in the human.

32. The method of claim 31, wherein the aqueous pharmaceutical formulation further comprises one or more excipients selected from the group consisting of absorption enhancement agents, isotonicity agents, stabilizing agents, antioxidants, preservatives, and pH adjustment agents to adjust the pH to a final pH between about 3.0 and about 5.0; and wherein the single dose comprises about 1.0 mg or about 2.0 mg of epinephrine and is intranasally administered with a single-dose nasal spray device.

33. A method for the treatment of anaphylaxis in a human comprising intranasally administering to the human with anaphylaxis a single dose of an aqueous pharmaceutical formulation comprising about 2.0 mg of epinephrine as the only pharmaceutically active ingredient in a volume of about 100 µL;
wherein the single dose is administered with one actuation of a single-dose nasal spray device into one nostril of the human;
wherein the intranasal administration of the single dose to the human with anaphylaxis provides plasma epinephrine concentrations in the human that are efficacious for the elimination of one, more than one, or all of the symptoms of anaphylaxis in the human.

34. A method for the treatment of anaphylaxis in a human comprising intranasally administering to the human with anaphylaxis a single dose of an aqueous pharmaceutical formulation comprising:
about 1.0 mg to about 2.0 mg of epinephrine as the only pharmaceutically active ingredient in the aqueous pharmaceutical formulation in a volume between about 50 µL and about 250 µL;
wherein the single dose is administered with one actuation of a single-dose nasal spray device into one nostril of the human;
wherein the intranasal administration of the single dose to the human with anaphylaxis provides plasma epinephrine concentrations in the human that are efficacious for the elimination of one, more than one, or all of the symptoms of anaphylaxis in the human with a time to maximum epinephrine plasma concentrations (Tmax) of less than 45 minutes.

35. The method of claim 34, wherein the single dose comprises about 1.0 mg or about 2.0 mg of epinephrine in a volume of about 100 µL and the intranasal administration of the single dose to the human with anaphylaxis provides plasma epinephrine concentrations with a Tmax of less than 35 minutes.

36. A method for the treatment of anaphylaxis in a human comprising intranasally administering to the human with anaphylaxis a single dose of an aqueous pharmaceutical formulation comprising:
about 1.0 mg to about 2.0 mg of epinephrine as the only pharmaceutically active ingredient in the aqueous pharmaceutical formulation in a volume between about 50 µL and about 250 µL, water, one or more absorption enhancement agents as excipients, and one or more additional excipients selected from the group consisting of isotonicity agents, stabilizing agents, antioxidants, preservatives, and pH adjustment agents to adjust the pH to a final pH between about 3.0 and about 5.0;
wherein the intranasal administration of the single dose to the human with anaphylaxis provides plasma epinephrine concentrations in the human that are efficacious for the elimination of one, more than one, or all of the symptoms of anaphylaxis in the human with a time to maximum epinephrine plasma concentrations (Tmax) of less than 45 minutes.

37. A method for the treatment of anaphylaxis in a human comprising intranasally administering to the human with anaphylaxis a single dose of an aqueous pharmaceutical formulation comprising:
about 2.0 mg of epinephrine as the only pharmaceutically active ingredient in the aqueous pharmaceutical formulation in a volume between about 50 µL and about 250 µL, water, one or more absorption enhancement agents as excipients, and one or more additional excipients selected from the group consisting of isotonicity agents, stabilizing agents, antioxidants, preservatives, and pH adjustment agents to adjust the pH to a final pH between about 3.0 and about 5.0;
wherein the single dose is administered with one actuation of a single-dose nasal spray device into one nostril of the human;
wherein the intranasal administration of the single dose to the human with anaphylaxis provides plasma epinephrine concentrations in the human that are efficacious for the elimination of one, more than one, or all of the symptoms of anaphylaxis in the human with a time to maximum epinephrine plasma concentrations (Tmax) of less than 45 minutes.

38. The method of claim 37, wherein the intranasal administration of the single dose of the aqueous pharmaceutical formulation provides plasma epinephrine concentrations with a Tmax of less than 35 minutes.

39. The method of claim 37, wherein the absorption enhancement agents are selected from the group consisting of alkyl glycosides, fatty acids, bile salts, cyclodextrins, phospholipids, and alcohols.

40. The method of claim 37, wherein the absorption enhancement agents are selected from the group consisting of dodecyl maltoside, polysorbate 20, polysorbate 80, oleic acid, sodium lauryl sulfate, sodium glycocholate, sodium taurocholate, and sodium taurodihydrofusidate.

41. A method for the emergency treatment of a type-1 hypersensitivity reaction in a human comprising intranasally administering to the human with the type-1 hypersensitivity reaction a single dose of an aqueous pharmaceutical formulation comprising about 2.0 mg of epinephrine as the only pharmaceutically active ingredient in the aqueous pharmaceutical formulation in a volume of about 100 µL, water, and additional excipients comprising dodecyl maltoside, benzalkonium chloride, sodium chloride, disodium salt of ethylenediaminetetraacetic acid (EDTA), sodium metabisulfite, and hydrochloric acid or sodium hydroxide to adjust the pH to a final pH between about 3.0 and about 5.0;
wherein the type-1 hypersensitivity reaction comprises anaphylaxis;
wherein the single dose is administered with one actuation of a single-dose nasal spray device into one nostril of the human;
wherein the intranasal administration of the single dose to the human with the type-1 hypersensitivity reaction provides plasma epinephrine concentrations in the human that are efficacious for the elimination of one, more than one, or all of the symptoms of anaphylaxis in the human with a time to maximum epinephrine plasma concentrations (Tmax) of less than 45 minutes.

42. The method of claim 41, wherein the type-1 hypersensitivity reaction is caused by stinging insects, biting insects, allergen immunotherapy, foods, drugs, diagnostic testing substances, or other allergens.

43. The method of claim 41, wherein the symptoms of the type-1 hypersensitivity reaction are selected from the group consisting of urticaria, generalized itching, nasal congestion, wheezing, difficulty breathing, cough, cyanosis, lightheadedness, dizziness, confusion, slurred speech, rapid pulse, palpitations, nausea or vomiting, abdominal pain or cramping, skin redness or inflammation, nasal flaring, and intercostal retractions.

44. A nasal spray pharmaceutical formulation consisting of about 2.0 mg of epinephrine in a volume of about 100 µL, dodecyl maltoside, benzalkonium chloride, sodium chloride, disodium salt of ethylenediaminetetraacetic acid (EDTA), sodium A metabisulfite, hydrochloric acid or sodium hydroxide to adjust the pH to a final pH between about 3.0 and about 5.0; and water.

* * * * *

UNITED STATES PATENT AND TRADEMARK OFFICE
CERTIFICATE OF CORRECTION

PATENT NO. : 11,918,655 B2
APPLICATION NO. : 18/206881
DATED : March 5, 2024
INVENTOR(S) : Richard Lowenthal et al.

Page 1 of 1

It is certified that error appears in the above-identified patent and that said Letters Patent is hereby corrected as shown below:

In the Claims

Column 70, Line 55, Claim 16, delete: "urticaria, or the symptoms" and replace with: --urticaria, and the symptoms--

Column 75, Line 10, Claim 44: delete: "sodium A metabisulfite" and replace with: --sodium metabisulfite--

Signed and Sealed this
Tenth Day of September, 2024

Katherine Kelly Vidal
*Director of the United States Patent and Trademark Office*